United States Patent
Lattuada et al.

(10) Patent No.: US 9,409,951 B2
(45) Date of Patent: *Aug. 9, 2016

(54) INTEGRIN TARGETED SYNTHETIC LIGANDS FOR DIAGNOSTIC AND THERAPEUTIC APPLICATIONS

(71) Applicant: BRACCO IMAGING S.P.A., Milan (IT)

(72) Inventors: Luciano Lattuada, Colleretto Giacosa (IT); Pierfrancesco Morosini, Villanova del Sillaro (IT); Fulvio Uggeri, Colleretto Giacosa (IT); Silvio Aime, Carignano (IT); Enzo Terreno, Bibiana (IT); Daniela Delli Castelli, Bibiana (IT); Carlo Scolastico, Lerici (IT); Leonardo Manzoni, Milan (IT); Daniela Arosio, Milan (IT)

(73) Assignee: BRACCO IMAGING S.P.A., Milan (IT)

( * ) Notice: Subject to any disclaimer, the term of this patent is extended or adjusted under 35 U.S.C. 154(b) by 337 days.

This patent is subject to a terminal disclaimer.

(21) Appl. No.: 14/153,706

(22) Filed: Jan. 13, 2014

(65) Prior Publication Data

US 2014/0178302 A1    Jun. 26, 2014

Related U.S. Application Data

(63) Continuation of application No. 11/885,353, filed as application No. PCT/IB2006/000455 on Mar. 3, 2006, now Pat. No. 8,636,977.

(30) Foreign Application Priority Data

Mar. 3, 2005 (IT) .............................. MI2005A0328

(51) Int. Cl.
| | |
|---|---|
| *C07K 7/64* | (2006.01) |
| *C07K 5/078* | (2006.01) |
| *C07D 401/06* | (2006.01) |
| *C07D 471/04* | (2006.01) |

(52) U.S. Cl.
CPC ................ *C07K 7/64* (2013.01); *C07D 401/06* (2013.01); *C07D 471/04* (2013.01); *C07K 5/06139* (2013.01)

(58) Field of Classification Search
None
See application file for complete search history.

(56) References Cited

U.S. PATENT DOCUMENTS

| | | | |
|---|---|---|---|
| 5,268,486 A | 12/1993 | Waggoner et al. | |
| 6,083,485 A | 7/2000 | Licha et al. | |
| 6,261,537 B1 | 7/2001 | Klaveness et al. | |
| 7,371,364 B2 | 5/2008 | Li et al. | |
| 7,655,217 B2 | 2/2010 | Licha et al. | |
| 7,897,142 B2 | 3/2011 | Cuthbertson et al. | |
| 8,636,977 B2 | 1/2014 | Lattuada et al. | |
| 2008/0317668 A1 | 12/2008 | Lattuada et al. | |

FOREIGN PATENT DOCUMENTS

| | | |
|---|---|---|
| EP | 1181940 A2 | 2/2002 |
| EP | 0 927 045 B1 | 12/2005 |
| WO | 98/01795 A2 | 3/1998 |
| WO | 2004/011487 A2 | 2/2004 |
| WO | 2005/007654 | 1/2005 |
| WO | 2005/042531 | 5/2005 |
| WO | 2006/092722 | 9/2006 |
| WO | 2008/102233 A1 | 8/2008 |
| WO | 2010/046900 A2 | 4/2010 |
| WO | 2010/076334 A2 | 7/2010 |
| WO | 2012/062777 A1 | 5/2012 |

OTHER PUBLICATIONS

Artale et al. "Synthesis of substituted conformationally constrained 6,5- and 7,5-fused bicyclic lactams as dipeptide mimics" *Tetrahedron* 59:6241-6250 (Aug. 2003).
Belvisi et al. "Targeting integrins: Insights into structure and activity of cyclic RGD pentapeptide mimics containing azabicycloalkane amino acids" *Bioorganic Med. Chem.* 14:169-180 (Jan. 2006).
Belvisi et al. "Potent integrin antagnists from a small library of RGD-including cyclic pseudopeptides" *Organic Lett.* 3:1001-1004 (Apr. 2001).
Belvisi et al. "Cyclic RGD peptides containing azabicycloalkane reverse-turn mimics" *Helv. Chim. Acta* 85:4353-4368 (Dec. 2002).
Breeman et al. "Optimising conditions for radiolabelling of DOTA-peptides with $^{90}$Y, $^{111}$In and $^{177}$Lu at high specific activities" *Eur. J. Nucl. Med. Mol.* 30:917-920 (Jun. 2003).
Brugieres et al. "Randomised double blind trial of the safety and efficacy of two gadolinium complexes (Gd-DTPA and Gd-DOTA)" *Neuroradiology* 36:27-30 (1994).
Chen et al. "Pegylated Arg-Gly-Asp peptide: $^{64}$Cu labeling and PET imaging of brain tumor $\alpha_v\beta_3$-integrin expression" *J. Nucl. Med.* 45:1776-1783 (Oct. 2004).
Chen et al. "MicroPET and autoradiographic imaging of breast cancer $\alpha_v$-integrin expression using $^{18}$F- and $^{64}$Cu-labeled RGD peptide" *Bioconjug. Chem.* 15:41-49 (Jan.-Feb. 2004).
Colombo et al. "Conformationally constrained dipeptides: Synthesis of bicyclic lactams by stereoselective radical cyclizations" *Gazzetta Chim. Ital.* 126:543-554 (Jan. 1996).
Feng & Lubell "Synthesis of enantiopure 7-[3-azidopropyl]indolizidin-2-one amino acid. A constrained mimic of the peptide backbone geometry and heteroatomic side-chain functionality of the Ala-Lys dipeptide" *J. Org. Chem.* 66:1181-1185 (Jan. 2001).
Haubner et al. "Stereoisomeric peptide libraries and peptidomimetics for designing selective inhibitors of the $\alpha_v\beta_3$ integrin for a new cancer therapy" *Angew. Chem. Int. Ed.* 36:1375-1389 (Aug. 1997).

(Continued)

*Primary Examiner* — Michael G Hartley
*Assistant Examiner* — Jennifer Lamberski
(74) *Attorney, Agent, or Firm* — Vivicar Law, PLLC

(57) ABSTRACT

The present invention relates to a novel class of diagnostically or therapeutically effective compounds comprising novel aza-bicycloalkane based cyclic peptides, acting as a targeting moiety towards integrin receptors.

20 Claims, 25 Drawing Sheets

(56) References Cited

OTHER PUBLICATIONS

Manzoni et al. "The first example of ring-closing olefin metathesis of dehydroamino acids: An application to the synthesis of azabicyclo[X.Y.0]alkanes" *Tetrahedron Lett.* 45:2623-2625 (Mar. 2004).

Marchi-Artzner et al. "Selective adhesion of endothelial cells to artificial membranes with a synthetic RGD-lipopeptide" *Chem. Eur. J.* 7:1095-1101 (Mar. 2001).

Müller et al. "Pharmacophore refinement of GPIIb/IIIa antagonists based on comparative studies of an antiadhesive cyclic and acyclic RDG peptides" *J. Computer-Aided Mol. Design* 8:709-730 (Dec. 1994).

Polyak & Lubell "Mimicry of peptide backbone geometry and heteroatomic side-chain functionality: Synthesis of enantiopure indolizidin-2-one amino acids possessing alcohol, acid, and azide functional groups" *J. Org. Chem.* 66:1171-1180 (Feb. 2001).

Schmitt & Tampe "ATP-lipids protein anchor and energy source in two dimensions" *J. Am. Chem. Soc.* 118:5532-5543 (1996).

Int'l Search Report for PCT/IB2006/000455, all pages, dated Oct. 6, 2006.

Written Opinion and Answer for PCT/IB2006/000455, all pages, dated Oct. 6, 2006.

Int'l Prel. Report on Patentability for PCT/IB2006/000455, all pages, dated Apr. 10, 2007.

Scheme 1

Reagents and conditions: i) $H_2$, Pd/C; ii) Cbz-Cl, TEA, DCM (78%); iii) MsCl, TEA, DCM; iv) $NaN_3$, DMF, 80°C (76% over two steps); v) $Me_3P$, $H_2O$, DCM (99%).

Reagents and conditions: i) $H_2$, Pd/C; ii) Cbz-Cl, TEA, DCM (80%); iii) MsCl, TEA, DCM; iv) $NaN_3$, DMF, 80°C (85% over two steps); v) $Me_3P$, $H_2O$, DCM (98%).

Scheme 2

Reagents and conditions: i) H₂, Pd/C; ii) Cbz-Cl, TEA, DCM (75%); iii) MsCl, TEA, DCM; iv) NaN₃, DMF, 80°C (80% over two steps); v) Me₃P, H₂O, DCM (98%).

Reagents and conditions: i) H₂, Pd/C; ii) Cbz-Cl, TEA, DCM (60%); iii) MsCl, TEA, DCM; iv) NaN₃, DMF, 80°C (90% over two steps); v) Me₃P, H₂O, DCM (99%).

Scheme 3

Reagents and conditions: i) TFA, DCM; ii) NH$_2$Arg(Pmc)GlyOMe, DIC, HOBt; iii) H$_2$, Pd/C; iv) CbzNHAsp(tBu)OH, DIC, HOBt; v) BnOH, Ti(OiPr)$_4$; vi) H$_2$, Pd/C; vii) HATU, HOAt, DIPEA.

Scheme 4

Synthesis of 6,5-*cis*.

Reagents and conditions: i) MsCl, TEA, DCM; ii) NaN$_3$, DMF, 80°C (62% over two steps); iii) H$_2$, Pd-C 10%, MeOH; iv) R$_6$COOH, HBTU, DIPEA, DCM; v) TFA Synthesis of 7,5-*cis*.

Reagents and conditions: i) MsCl, TEA, DCM; ii) NaN$_3$, DMF, 80°C, (60% over two steps); iii) H$_2$, Pd-C 10%, MeOH; iv) R$_6$COOH, HBTU, DIPEA, DCM; v) TFA Scheme 5

Synthesis of 6,5-*trans*.

Reagents and conditions: i) MsCl, TEA, DCM; ii) NaN$_3$, DMF, 80°C (60% over two steps); iii) H$_2$, Pd-C 10%, MeOH; iv) R$_6$COOH, HBTU, DIPEA, DCM; v) TFA Synthesis of 7,5-*trans*.

Reagents and conditions: i) MsCl, TEA, DCM; ii) NaN$_3$, DMF, 80°C (75% over two steps); iii) H$_2$, Pd-C 10%, MeOH; iv) R$_6$COOH, HBTU, DIPEA, DCM; v) TFA Scheme A Preparation of the starting products n = 1 or 2

Reagents and conditions: HClO$_4$, AcOtBu, 0°C; ii. Amberlyst A-21, ClCOCOOMe, -20°C; iii. LiBH$_4$, THF, 0°C; iv. (COCl)$_2$, DMSO, TEA, CH$_2$Cl$_2$, -60°C; v. Bn-NH-OH·HCl, NaHCO$_3$, EtOH/H$_2$O, 80°C; vi.

Linkers 1  2  3

4  5  6

7  8

WO 04/065407

9  10

11  12  13

Synth. Commun. 2001, 31, 1307; Org. Prep. Proced. Int. 1996, 28, 49; J. Am. Chem. Soc. 2002, 124, Tetrahedron Lett. 2001, 42, 7443;

14

$X = CH_2CH_2, CH_2OCH_2, (CH_2OCH_2)_3,$

15

US 5,514,810;

16

17

18    X = CH$_2$CH$_2$, CH$_2$OCH$_2$, (CH$_2$OCH$_2$)$_3$

*Tetrahedron Lett.* 2005, 46, 1463

19

20

21

22

23

24

25

26

Chelators

1
*Bioconj. Chem* (1999), *10*, 137

2
WO 01/46207

3
*Bioconj. Chem* (1999), *10*, 137

4

5

*Bioorg. Chemm. Lett.* (2000), *10*, 2133

6
WO 04/065407

7
WO 05/062828

8
WO 05/062828

9
WO 2006/002873

10
WO 2006/002873

11
WO 2006/002873

12
WO 2006/002873

13
WO 2006/002873

14
WO 2006/002873

Radionuclide chelants

22

23

*Bioconjugate Chem.* 1999, *10*, 489

24
*Bioconjugate Chem.* 1999, *10*, 470

25
*Bioconjugate Chem.* 1990, *1*, 132

27
*Bioconjugate Chem.* 1999, *10*, 254

27
*Eur. J. Nucl. Med.* 1994, *21*, 437

28
*Inorg. Chem.* 1997, *36*, 5799

INTEGRIN TARGETED SYNTHETIC LIGANDS FOR DIAGNOSTIC AND THERAPEUTIC APPLICATIONS

CROSS-REFERENCE TO RELATED APPLICATIONS

This application is a continuation of application Ser. No. 11/885,353, filed Nov. 23, 2007, allowed; which is the national stage of Application No. PCT/IB2006/000455, filed Mar. 3, 2006; which claims priority benefit of Italian Application No. MI2005A000328, filed Mar. 3, 2005; the entire contents of which are incorporated by reference.

TECHNICAL FIELD

The present invention is in the technical field of the targeted diagnostic imaging and relates to novel cyclic peptidomimetic compounds having an azabicycloalkane structure conjugated to a biologically active molecule.

In particular, the invention relates to a novel class of diagnostically or therapeutically effective compounds comprising novel aza-bicycloalkane based cyclic peptides, acting as a targeting moiety towards integrin receptors.

The invention further relates to novel pharmaceutical compositions comprising them and uses thereof in targeted imaging or therapy of solid tumors and in general, of the pathological conditions associated with angiogenesis.

BACKGROUND OF THE INVENTION

A great number of physiological processes involve biologically active peptides, through their interactions with receptors and enzymes. However, peptides are not to be considered ideal drugs, given their poor metabolic stability, rapid excretion and low selectivity for specific receptors. A valid alternative involves the design of peptide analogues which are capable of mimicking the action of the natural peptide at the receptor level (peptidomimetic) [(a) Kahn, M. (Editor). Peptide Secondary Structure Mimetics. *Tetrahedron Symposia-in-Print* No. 50 1993, 49, 3433-3689. (b) Gante, J. *Angew. Chem., Int. Ed. Engl.* 1994, 33, 1699-1720. (c) Olson, G. L.; Bolin, D. R.; Bonner, M. P.; Bös, M.; Cook, C. M.; Fry, D. C.; Graves, B. J.; Hatada, M.; Hill, D. E.; Kahn, M.; Madison, V. S.; Rusiecki, V. K.; Sarabu, R.; Sepinwall, J.; Vincent, G. P.; Voss, M. E. *J. Med. Chem.* 1993, 36, 3039-3049. (d) Kitagawa, O.; Velde, D. V.; Dutta, D.; Morton, M.; Takusagawa, F.; Aubé, J. *J. Am. Chem. Soc.* 1995, 117, 5169-5178. (e) Giannis, A.; Kolter, T. *Angew. Chem.; Int. Ed. Engl.* 1993, 32, 1244. (f) Aube, J. *Tetrahedron Symposia-in-Print* No. 50, 2000, 56, 9725-9842].

During our research into peptide secondary structure mimetics, certain 6,5- and 7,5-azabicycloalkane aminoacids have been synthesised [(a) Colombo, L.; Di Giacomo, M.; Scolastico, C.; Manzoni, L.; Belvisi, L.; Molteni, V. *Tetrahedron Lett.* 1995, 36, 625; (b) Colombo, L.; Di Giacomo, M.; Belvisi, L.; Manzoni, L.; Scolastico, C. *Gazz. Chim. It.* 1996, 126, 543; (c) Colombo, L.; Di Giacomo, M.; Brusotti, G.; Sardone, N.; Angiolini, M.; Belvisi, L.; Maffioli, S.; Manzoni, L.; Scolastico, C. *Tetrahedron* 1998, 54, 5325-5336; (d) Angiolini, M.; Araneo, S.; Belvisi, L.; Cesarotti, E.; Checchia, A.; Crippa, L.; Manzoni, L.; Scolastico, C. *Eur. J. Org. Chem.* 2000, 2571-2581; (e) Manzoni, L.; Colombo, M.; May, E.; Scolastico, C. *Tetrahedron* 2001, 57, 249; (f) Belvisi, L.; Colombo, L.; Colombo, M.; Di Giacomo, M.; Manzoni, L.; Vodopivec, B.; Scolastico, C. *Tetrahedron* 2001, 57, 6463; (g) EP 1 077 218; (h) Colombo, L.; Di Giacomo, M.; Vinci, V.; Colombo, M.; Manzoni, L.; Scolastico, C. *Tetrahedron,* 2003, 59, 4501-4513; (i) Manzoni, L.; Colombo, M.; Scolastico, C. *Tetrahedron Lett.* 2004, 45, 2623-2625; (l) Belvisi, L.; Colombo, L.; Manzoni, L.; Potenza, D.; Scolastico, C. *Synlett,* 2004, 1449-1471.

These structures may be considered as conformationally constrained analogues of the Ala-Pro and Phe-Pro dipeptide units. [(a) Belvisi, L.; Bernardi, A.; Manzoni, L.; Potenza, D.; Scolastico, C. *Eur. J. Org. Chem.* 2000, 2563-2569; (b) Gennari, C.; Mielgo, A.; Potenza, D.; Scolastico, C.; Piarulli, U.; Manzoni, L. *Eur. J. Org. Chem.* 1999, 379]. The functionalisation of such molecules with heteroalkyl substituents is an aim of great interest, since the side chains may increase the affinity of the peptide for the receptor by interacting with the hydrophobic or hydrophilic sites of the receptor itself. A further advantage of such systems is the possibility of binding to different pharmacophoric groups and hence the possibility of creating a library, with the member components of which having different biological properties and activities. During our research into peptide secondary structure mimetics, certain 6,5- and 7,5-azabicycloalkane aminoacids have been synthesised which have been functionalised with heteroalkyl appendages [(a) Artale, E.; Banfi, G.; Belvisi, L.; Colombo, L.; Colombo, M.; Manzoni, L.; Scolastico, C. *Tetrahedron,* 2003, 59, 6241-6250; (b) Bracci, A.; Manzoni, L.; Scolastico, C. *Synthesis* 2003, 2363-2367; (c) Bravin, F. M.; Busnelli, G.; Colombo, M.; Gatti, F.; Manzoni, L.; Scolastico, C. *Synthesis,* 2004, 353; (d) Manzoni, L.; Belvisi, L.; Colombo, M.; Di Carlo, E.; Formi, A.; Scolastico, C. *Tetrahedron Lett.* 2004, 45, 6311-6315].

Furthermore, analogously to what occurs for non-substituted conformationally constrained dipeptide mimetics [Belvisi, L.; Bernardi, A.; Checchia, A.; Manzoni, L.; Potenza, D.; Scolastico, C.; Castorina, M.; Cupelli, A.; Giannini, G.; Carminati, P.; Pisano, C. *Org. Lett.* 2001, 3, 1001, C. Scolastico, L. Manzoni, G. Giannini. Brit. UK Pat. Appl. 2004. GB 2395480] such heteroalkyl substituted lactams may be incorporated into cyclic pseudo-peptides containing RGD sequence.

Such molecules may be selectively targeted to those tissues over-expressing certain receptors (e.g. epithelial cells involved in vascular growth), so as to be able to be used to inhibit angiogenesis and selectively control the release of any drugs optionally bound to the substituent groups on the lactam ring [Arap, W.; Pasqualini, R.; Ruoslahti, E. *Science,* 1998, 279, 377]. Thus, from a first point of view, the low number of "scaffolds" reported in the literature necessitates the design and synthesis of novel conformationally constrained dipeptide mimetics, functionalised with hetero-substituted side chains for interaction with various receptors.

Moreover, and from another relevant point of view, today is well known that the cell adhesion molecule $\alpha_v\beta_3$ is an important player in the process of tumor angiogenesis and metastasis. With the term angiogenesis is identified a formation process of new blood vessels that occurs not only during embryonic development and normal tissue growth and repair, but is also associated with the female reproductive cycle, establishment and maintenance of pregnancy, and repair of wounds and fractures. In addition to angiogenesis that occurs in the normal individual, angiogenic events are involved in a number of pathological processes, notably tumor growth and metastasis, and other conditions in which blood vessel proliferation is increased, such as diabetic retinopathy, psoriasis and arthropathies. Angiogenesis is so important in the transition of a tumor from hyperplastic to neoplastic growth, that inhibition of angiogenesis has become an active cancer therapy research field. Tumor angiogenesis differs significantly from physiological angiogenesis. The differences include aberrant vascular structure, altered endothelial cell-pericyte interactions, abnormal blood flow, increased permeability and delayed maturation. Molecules regulating angiogenesis include growth factor receptors, tyrosine kinase receptors, G protein-coupled receptors for angiogenesis modulating proteins, and integrins [Bergers G., L. E. Benjamin, *Nat. Rev. Cancer*, 2003, 3:401-410; Ferrara N., *Nat. Rev. Cancer*, 2002, 2:795-803, Nyberg, P., L. Xie, R. Kalluri, *Cancer Res.*, 2005, 65:3967-3979]. Increasing amounts of evidences now imply that integrin signaling plays a key role in tumor angiogenesis and metastasis [Brooks, P. C., R. A. Clark, D. A. Cheresh, 1994, *Science*, 264:569-571, Kumar, C. C., 2003, *Curr. Drug Targets*, 4:123-131]. The $\alpha_v\beta_3$ integrin, in particular, is significantly up-regulated on endothelium during angiogenesis but not on quiescent endothelium [Hood, J. D. and D. A. Cheresh, 2002, *Nat. Rev. Cancer*, 2:91-1000, Xiong, J. P., T. Stehle, R. Zhang, A. Joachimiak, et al., 2002, *Science*, 296:151-155, Jin, H. and J. Varner, 2004, *Br. J. Cancer*, 90:561-565]. Research has shown that tumor expression of integrin $\alpha_v\beta_3$ correlates well with tumor in several malignancy such as melanoma, glioma, ovarian cancer, and breast cancer. Thus, the ability to quantitatively image integrin $\alpha_v\beta_3$ expression in vivo in a non-invasive manner may shed new light into the mechanism of angiogenesis and antiangiogenic treatment efficacy based on integrin antagonism. Tumor integrin expression imaging will also aid in lesion detection, to more appropriately select patient for anti-integrin treatment, in new anti-integrin drug development/validation, as well as in treatment monitoring and optimization.

Kessler and coworkers have provided new cyclic RGD based pentapeptides including the optimized c(RGDfV) system [see, for instance, US2002/0198142 and EP 0632053, U.S. Pat. No. 6,001,961] wherein the said pentapeptides are proposed for use, as such, as integrin-inhibitor drugs in the control of diseases, in particular disorders of the circulation, thrombosis, cardiac infarction, arteriosclerosis, inflammations, and angiogenesis. Cited references, however, do not suggest the use of claimed peptides or of suitable derivatives thereof for the diagnostic imaging or radiotherapy of angiogenesis and angiogenic disorders.

EP1068244 discloses pharmaceuticals useful for the diagnosis and treatment of cancer comprising peptides or peptidomimetics targeted to receptors up-regulated during angiogenesis and chelators.

Diagnostic or therapeutic agents including the RGD sequence and, particularly, the above c(RGDfV) cyclic peptides targeted to integrin receptors are also known: [Janssen, M. L., W. J. Oyen, I. Dijkgraaf, et al. 2002, *Cancer Res.* 62:6146-6151; Haubner, R. H., H. J. Wester, et al. *Cancer Res.* 61:1781-1785; Haubner, R. H., H. J. Wester, et al. 2003, *Q. J. Nucl. Med.* 47:189-199; Haubner, R. H., H. J. Wester, 2004, *Curr. Pharm. Des.* 10:1439-1455; Wang, W., S. Ke, et al. 2004, *Mol. Imaging* 3:343-351; Sunkuku, K., K. Shi, et al., 2005, *Mol. Imaging*, 4:75-87, Sipkins D. A., D. A. Cheresh, et. al., Nat. Med. 4:623-626].

The said prior art agents, however, generally suffer of drawbacks deriving from poor diffusion or transport, limited availability, and/or lack of specificity all resulting in a modest tumor-to-background ratio, and very low contrast observed in angiogenic regions.

Thus still remains a need for diagnostic and therapeutic agents that, when administered in vivo to a mammal, may combine high specificity and acceptable pharmacokinetic properties.

SUMMARY OF THE INVENTION

The present invention relates to novel therapeutic or diagnostic agents comprising cyclic peptide derivatives able to selectively bind to integrin receptors.

In particular, the cyclic peptide derivatives of the invention comprise an aza-bicycloalkane structure, acting as conformationally constrained mimetic of the omoSer-Pro dipeptide, that is further conjugated to a biologically active molecule. The said peptide derivatives are able to selectively bind to integrin receptors thus they act, according to the present invention, as targeting moiety able to bring and successfully bound an active moiety linked thereto to this particular class of receptors.

This class of diagnostic or therapeutic agents may find application for the diagnosis, prevention and treatment of pathological conditions associated with angiogenesis.

As detailed in the following paragraphs, the present invention relates to a novel class of compounds; to a manufacturing process for their preparation; to these same compounds for use as therapeutic or diagnostic agents; to the use of these latter in the preparation of pharmaceutical compositions for treatment, prevention and imaging of angiogenesis and of pathological conditions associated thereto.

According to a still different embodiment of the invention, also provided is a method for the treatment and prevention of angiogenesis and of related disorders, as well as a method for imaging angiogenesis both in vitro and in vivo, the said methods comprising the administration and use of the compounds of the invention.

BRIEF DESCRIPTION OF THE DRAWINGS

FIG. 1 discloses, schematized in Scheme 1, the synthetic process for the preparation of compounds of general formulae (Ia) 6,5-trans- and (Ib) 6,5-cis-fused, wherein n=1;

FIG. 2 discloses, schematized in Scheme 2, the synthetic process for the preparation of compounds of general formulae (Ia) 7,5-trans and (Ib) 7,5-cis fused, wherein n=2;

FIG. 3 discloses, schematized in Scheme 3, the cyclization process.

FIGS. 4-5 disclose, schematized in Scheme 4 and 5 the preparation of the biologically active derivatives of the invention;

Figure 4:
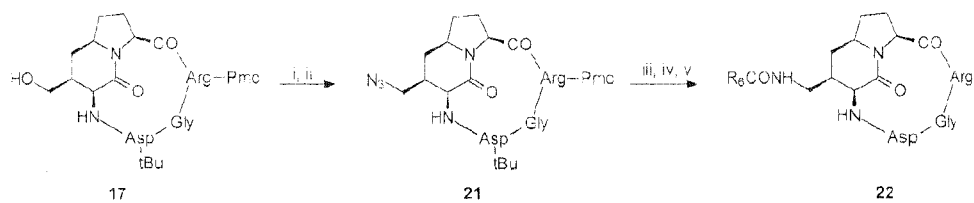
Figure 4:
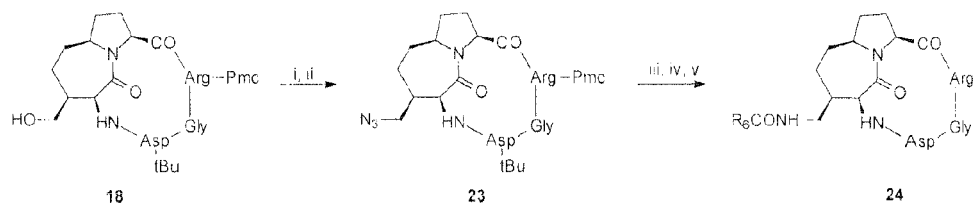
Figure 5:
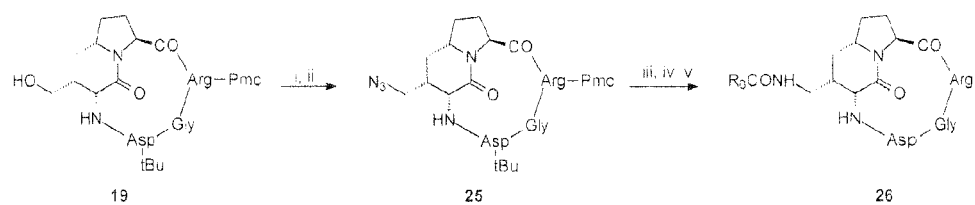
Figure 5:
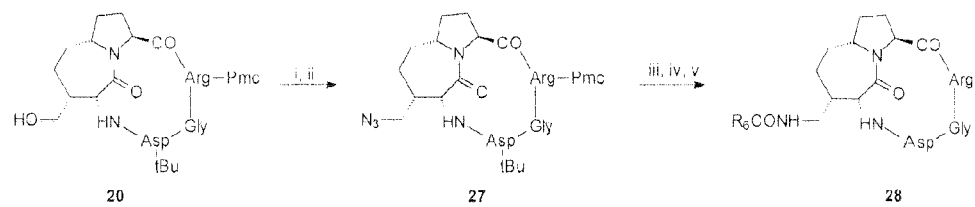

(IIa) and (IIb) and of a biologically active derivative thereof; in particular in FIG. 4, scheme 4, is reported the preparation of derivative 6,5- and 7,5-cis and in FIG. 5, scheme 5, is reported the preparation of the 6,5- and 7,5-trans derivative.

Figure 6:
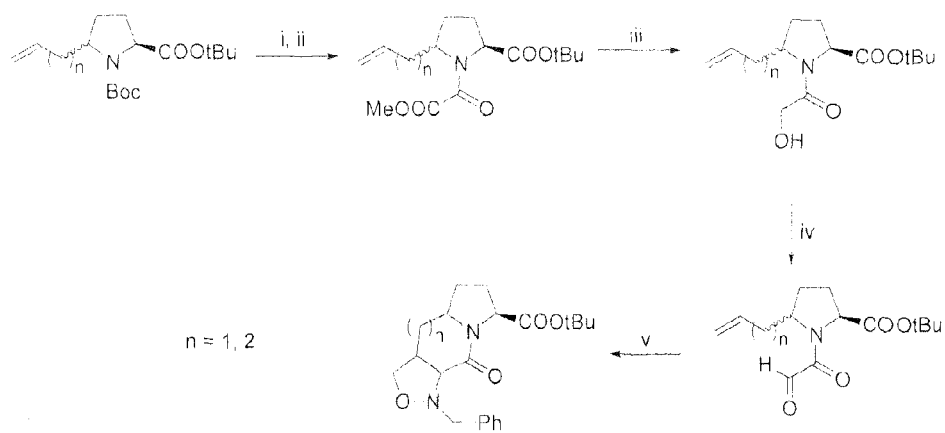

FIG. 6-Scheme A—discloses the preparation of the starting products.

Figure 7A:
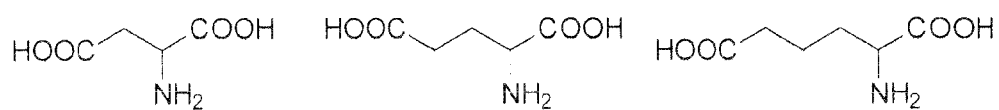
Figure 7A:
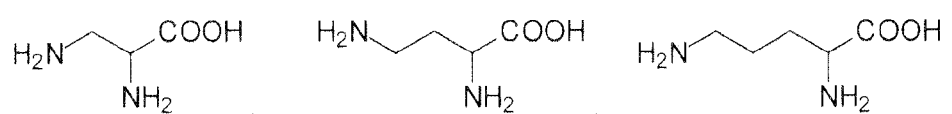
Figure 7A:
Figure 7A:
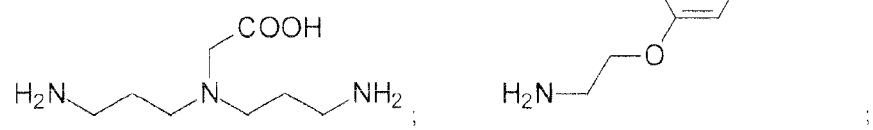
Figure 7B:
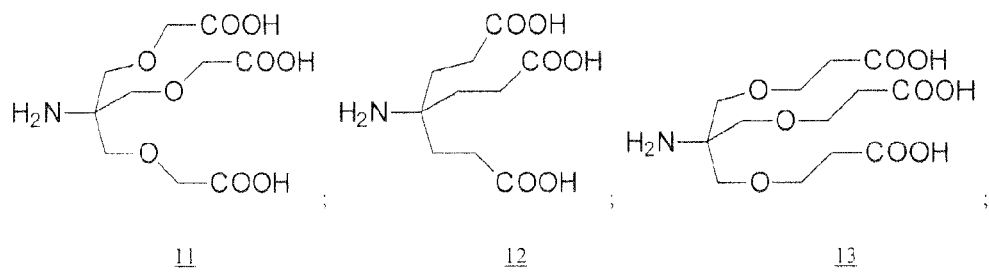
Figure 7B:
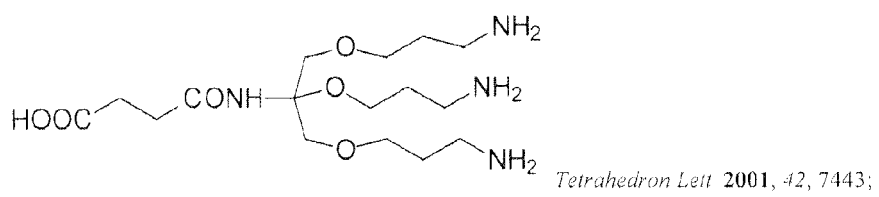
Figure 7B:
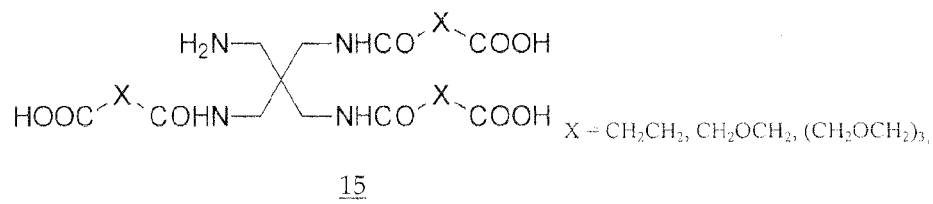
Figure 7B:
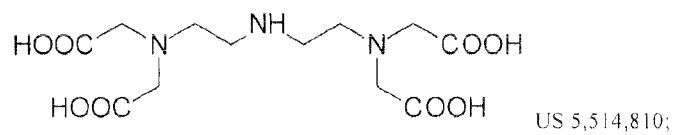
Figure 7B:
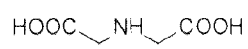
Figure 7C:
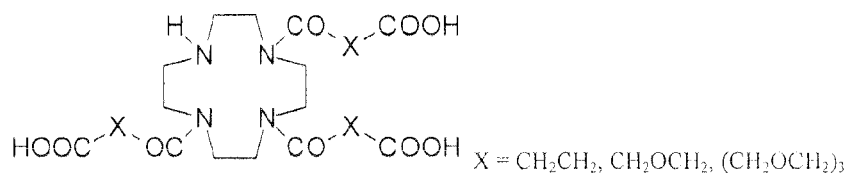
Figure 7C:
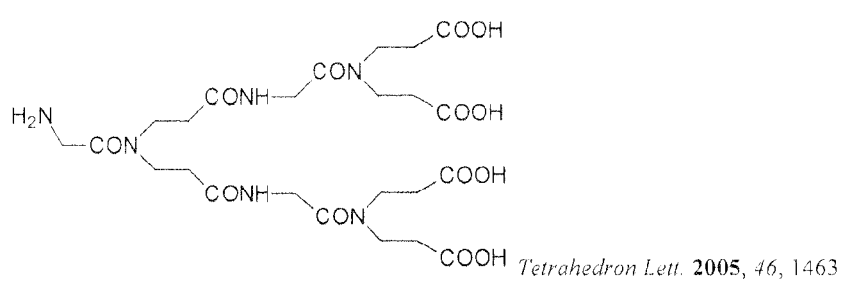
Figure 7C:
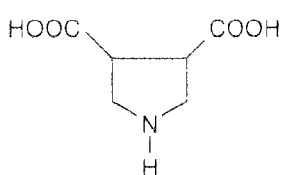
Figure 7C:
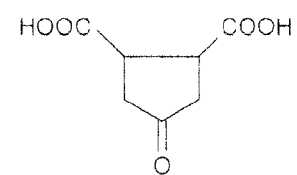
Figure 7C:
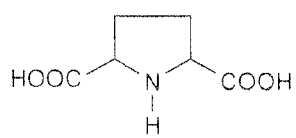
Figure 7C:
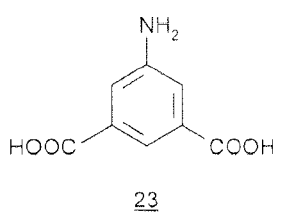
Figure 7C:
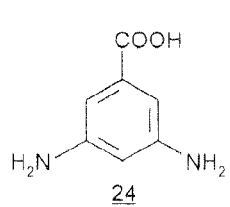
Figure 7C:
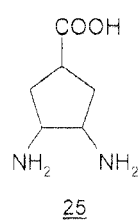
Figure 7C:
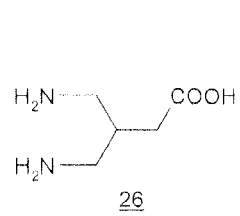

FIGS. 7A, 7B, and 7C illustrate examples of anchoring systems employed for preparing multimeric constructs of the invention.

Figure 8A:
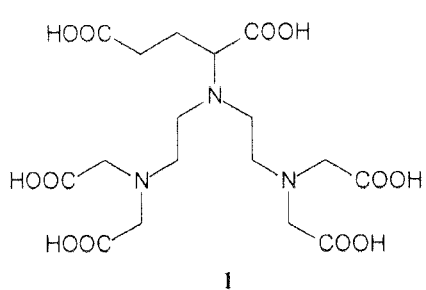
Figure 8A:
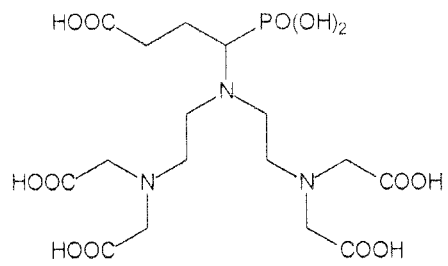
Figure 8A:
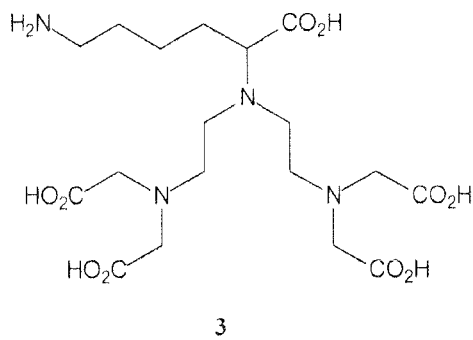
Figure 8A:
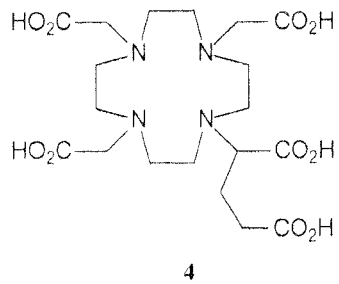
Figure 8A:
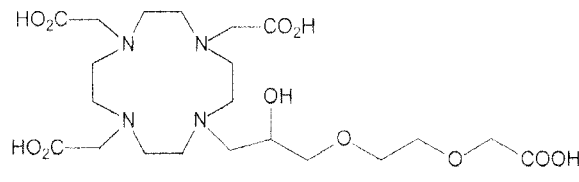
Figure 8B:
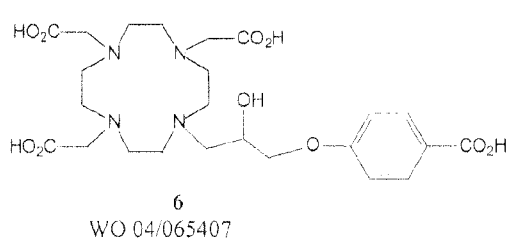
Figure 8B:
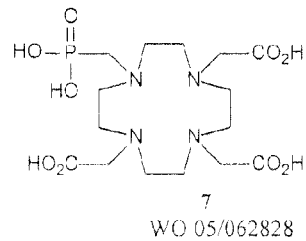
Figure 8B:
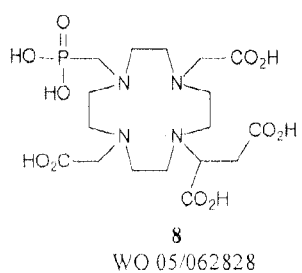
Figure 8B:
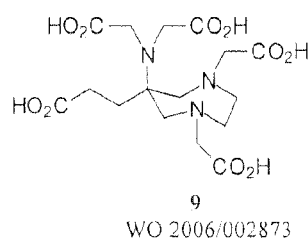
Figure 8B:
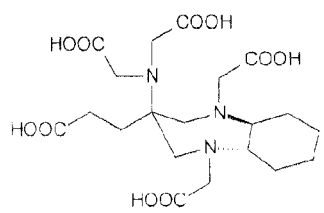
Figure 8B:
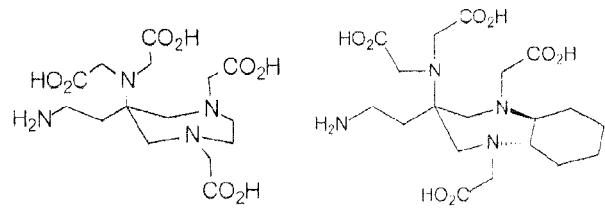
Figure 8B:
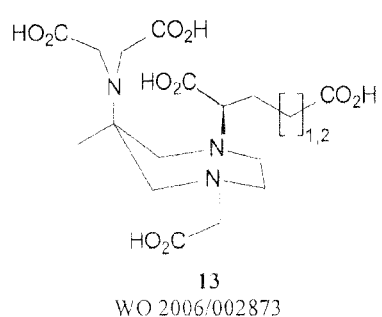
Figure 8B:
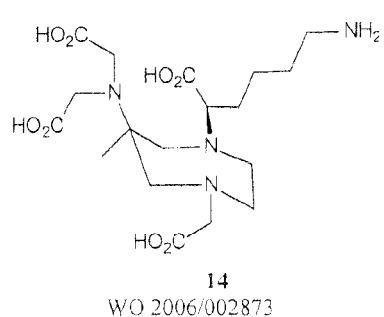
Figure 8C:
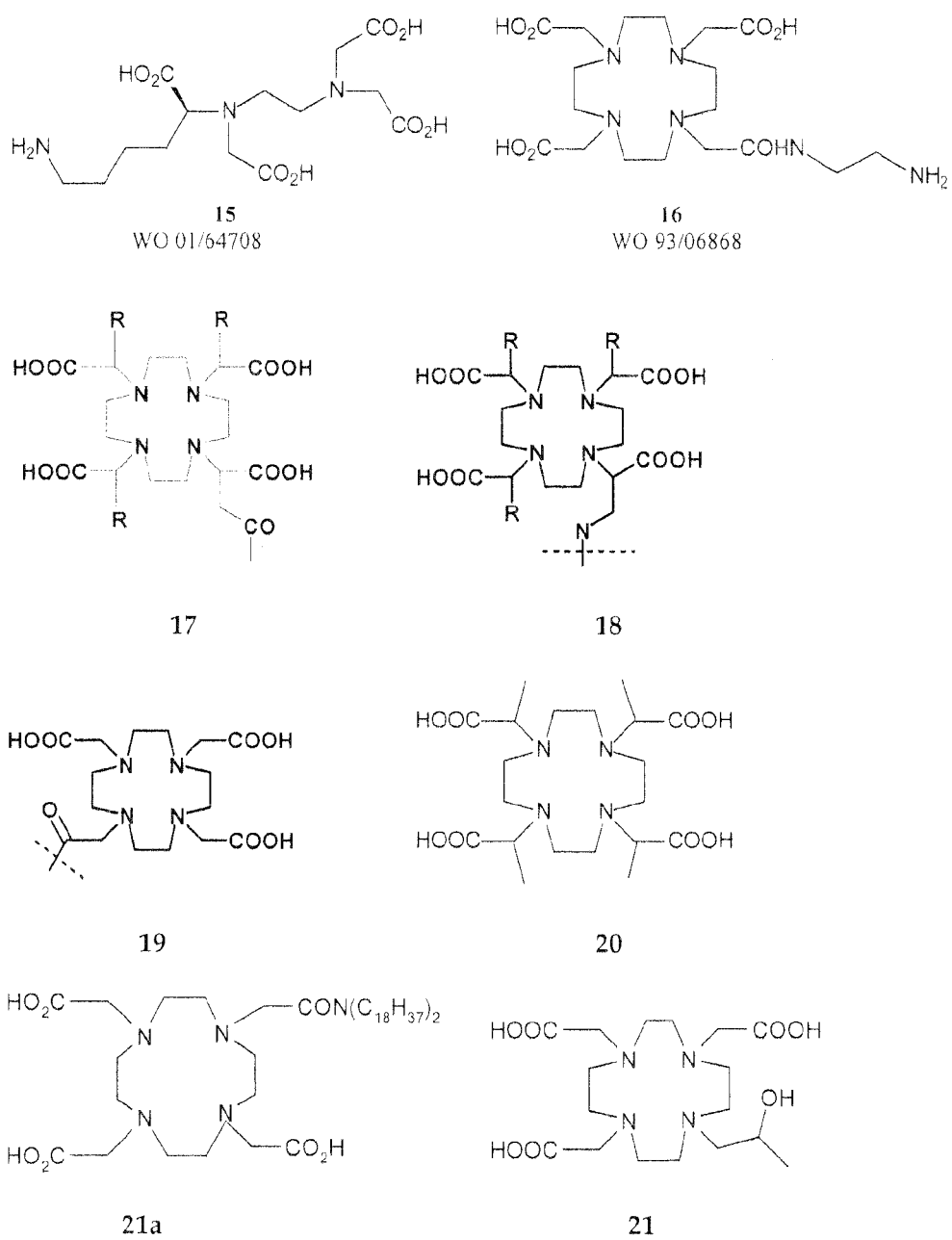

FIGS. 8A, 8B, and 8C illustrate examples of preferred chelators for either $^{111}$In and lanthanides such as paramagnetic $Gd^{3+}$ or radioactive lanthanides such as, for example, $^{77}$Lu, $^{90}$Y, $^{153}$Sm, and $^{166}$Ho.

Figure 9A:
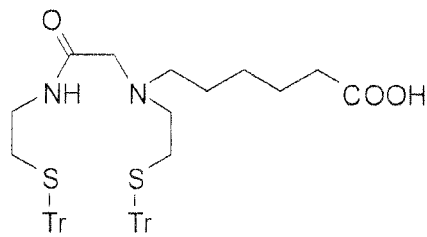
Figure 9A:
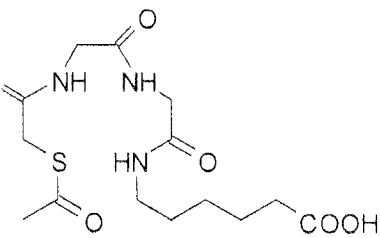
Figure 9A:
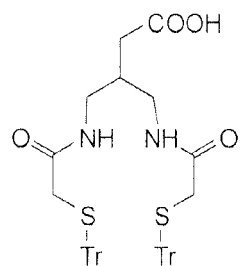
Figure 9A:
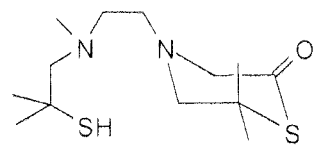
Figure 9A:
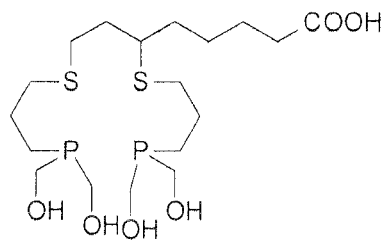
Figure 9A:
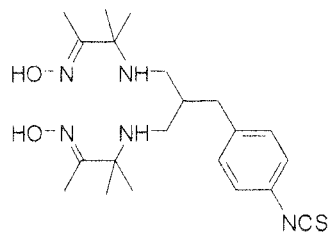
Figure 9A:
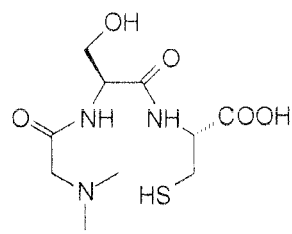
Figure 9B:
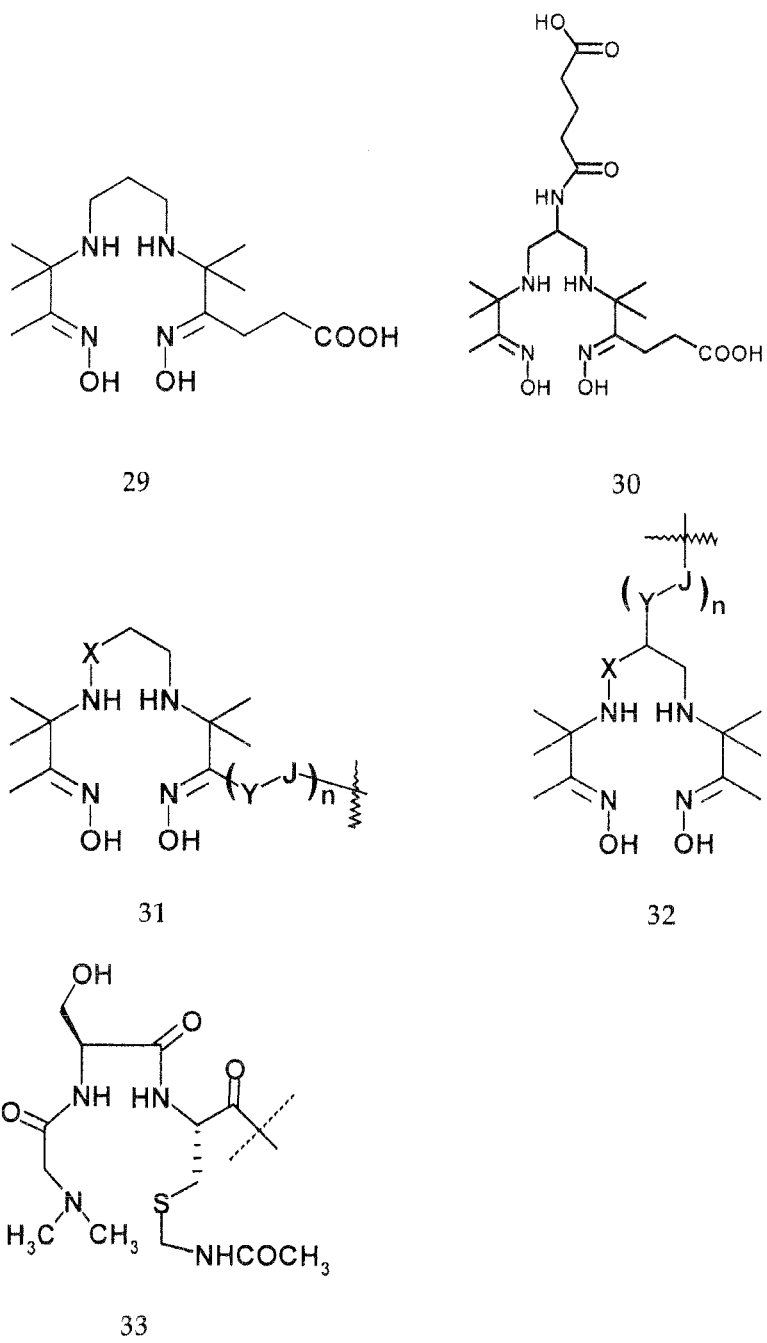

FIGS. 9A and 9B illustrate examples of preferred chelators of radioactive metal ion such as $^{90m}$Tc, $^{186}$Re, and $^{188}$Re.

Figure 10:
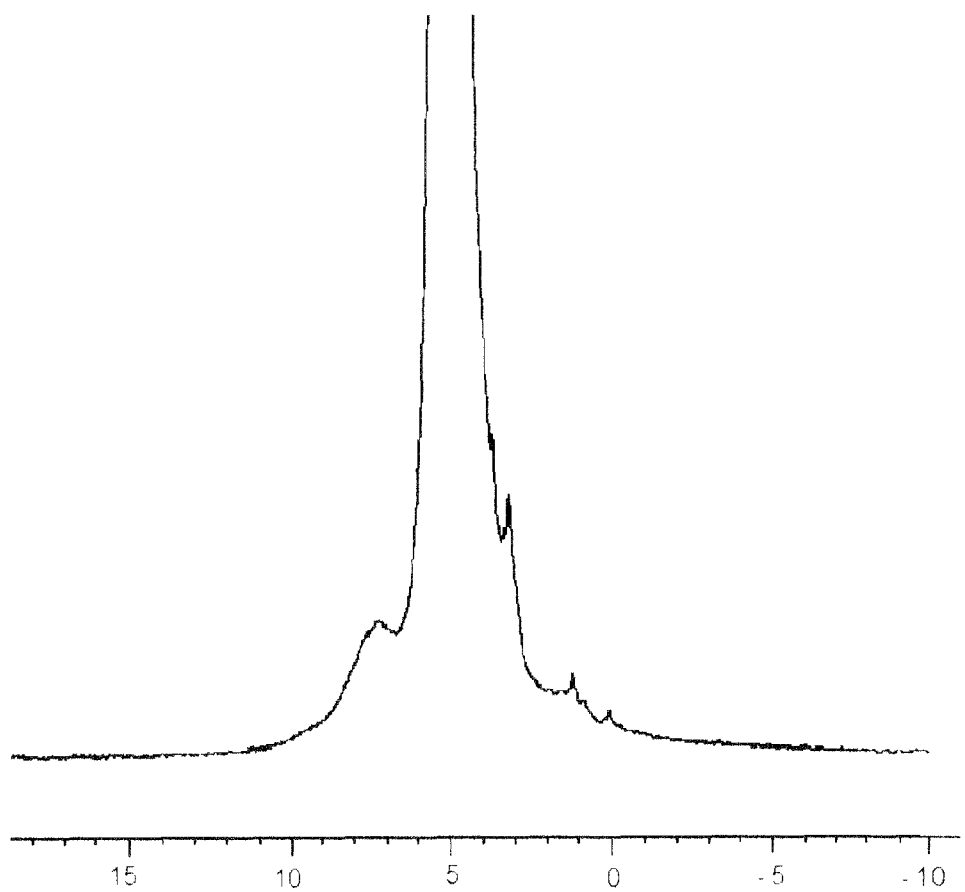

FIG. 10 reports the $^1$H-NMR spectrum (14.1 T, 298 K) of the preparation of the of biotinylated LIPOCEST agent of Example 1. The chemical shift difference between intraliposomal and bulk water was 3 ppm.

Figure 11:
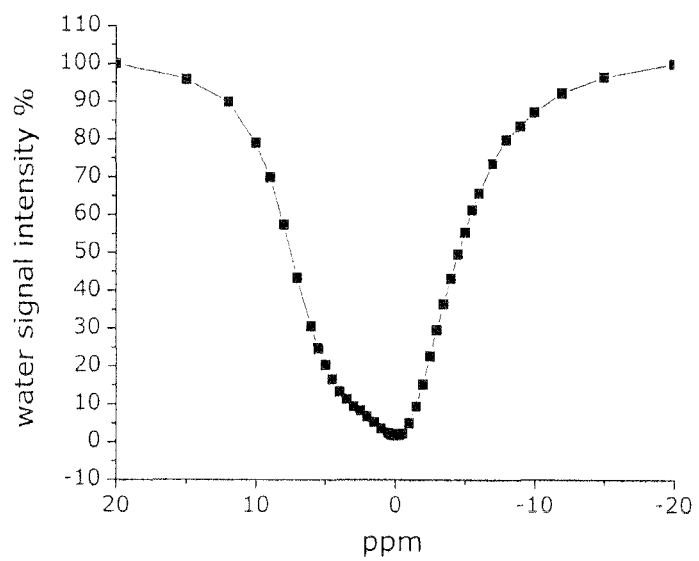

FIG. 11 reports the normalised Z-spectrum of the of the preparation of the LIPOCEST compound of Example 1 (7 T, irrad. pulse: rectangular, irrad. power 6 mT, irrad. time 2 s, 312 K).

Figure 12:
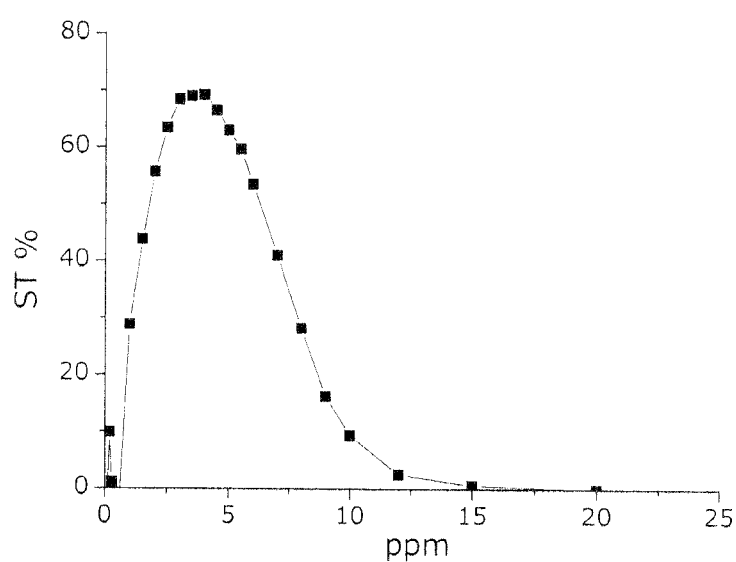

FIG. 12 reports the corresponding ST-spectrum of the preparation of the LIPOCEST compound of Example 1. A Saturation Transfer (ST) % of ca. 70% was observed at 3 ppm from bulk water.

Figure 13:
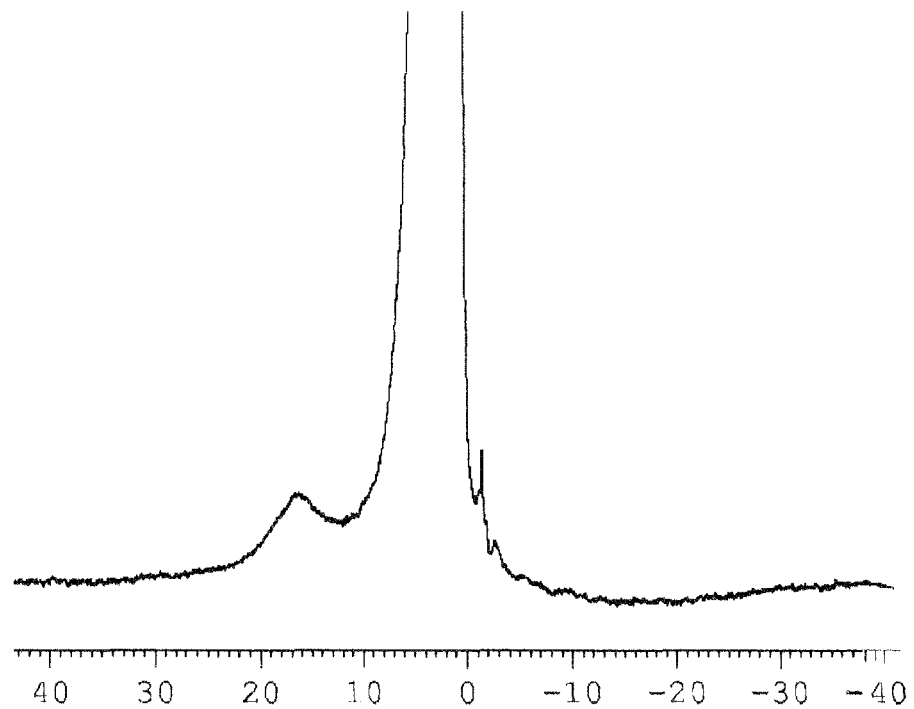

FIG. 13 reports the $^1$H-NMR spectrum (14.1 T, 298 K) of the preparation of the biotinylated LIPOCEST agent of Example 2.

Figure 14:
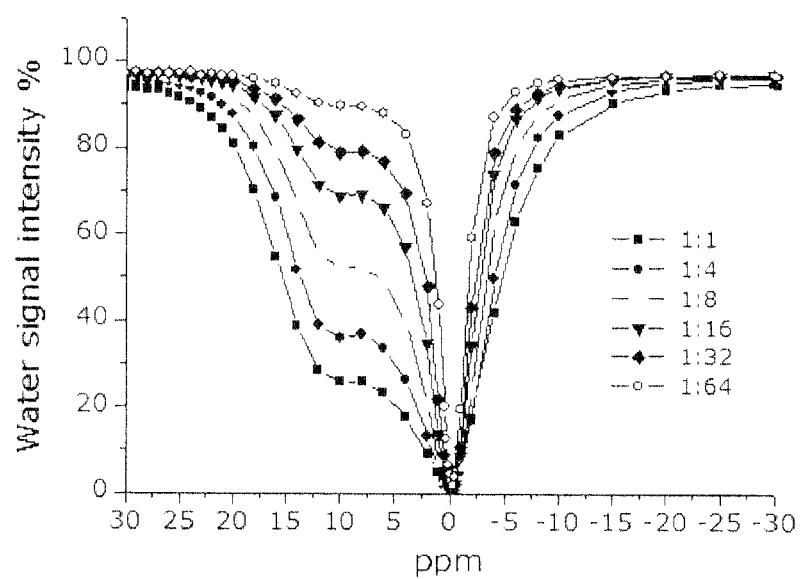

FIG. 14 reports the normalised Z-spectra of diluted samples of the preparation of the biotinylated LIPOCEST agent of Example 2 (7 T, irrad. pulse: rectangular, irrad. power 6 mT, irrad. time 2 s, 312 K).

Figure 15:
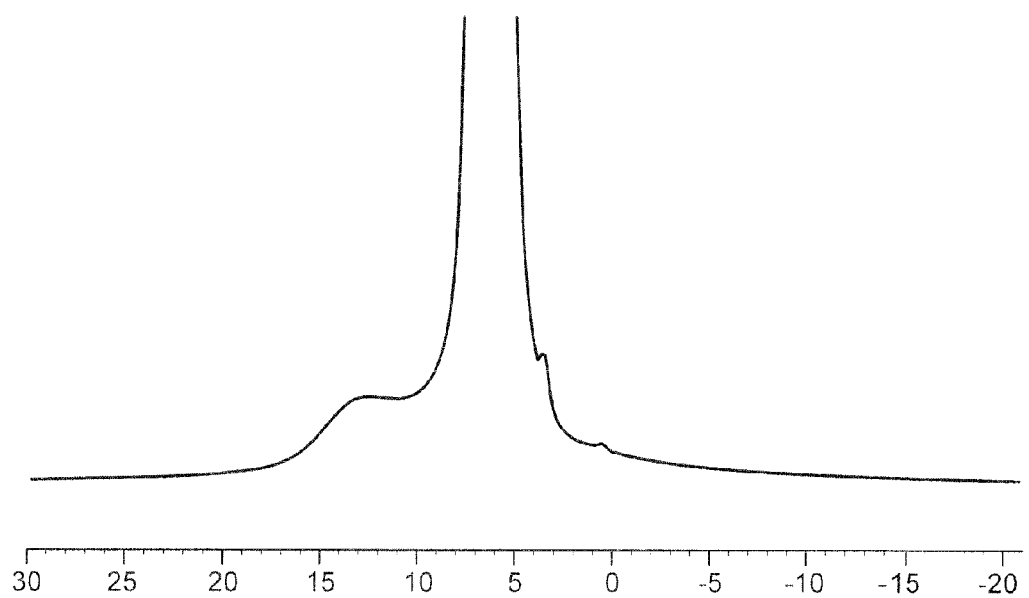

FIG. 15 reports the $^1$H-NMR spectrum (14.1 T, 298 K) of the preparation of the LIPOCEST of Example 3. The chemical shift difference between intraliposomal and bulk water was 10 ppm.

Figure 16:
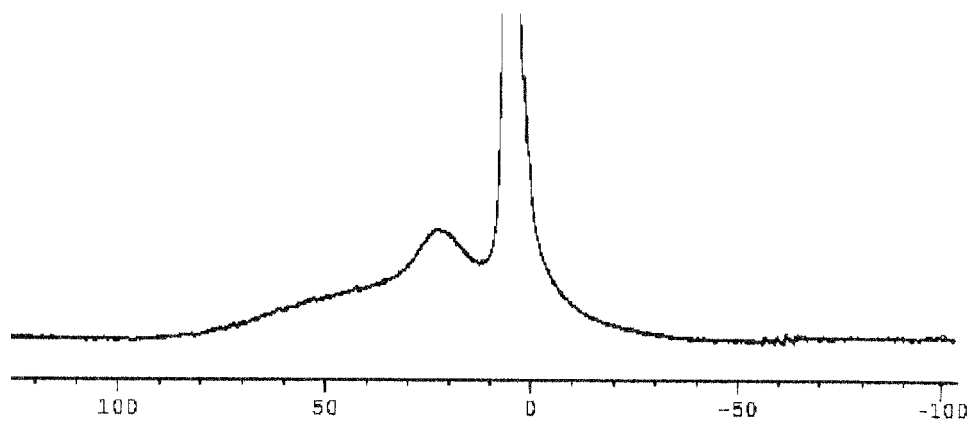

FIG. 16 reports the $^1$H-NMR spectrum (14.1 T, 298 K) of the of the preparation of the LIPOCEST of Example 4. The chemical shift difference between intraliposomal and bulk water was 19.3 ppm.

Figure 17:
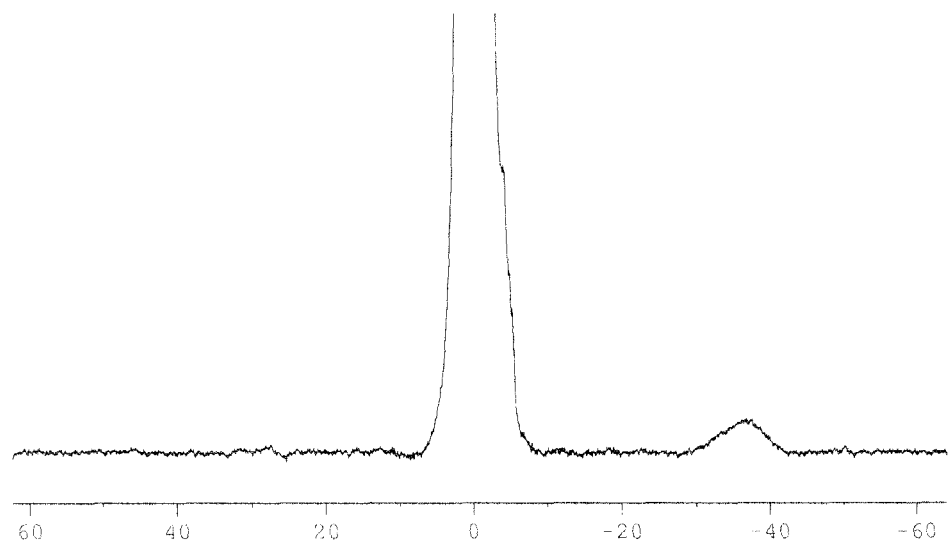

FIG. 17 reports the $^1$H-NMR spectrum (14.1 T, 298 K) of the preparation of the LIPOCEST of Example 5. The chemical shift difference between intraliposomal and bulk water was −36 ppm.

Figure 18:
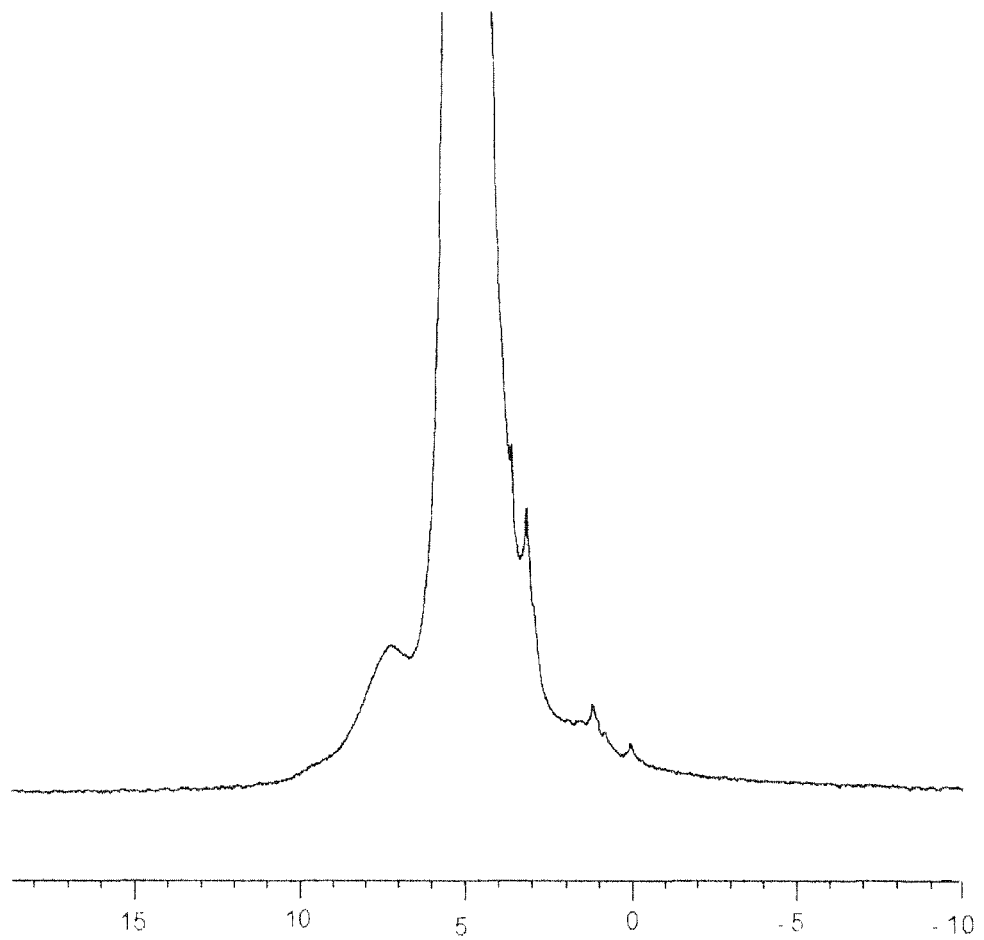

FIG. 18 reports the $^1$H-NMR spectrum (14.1 T, 298 K) of the preparation of the LIPOCEST of Example 6. The chemical shift difference between intraliposomal and bulk water was 3 ppm.

Figure 19:
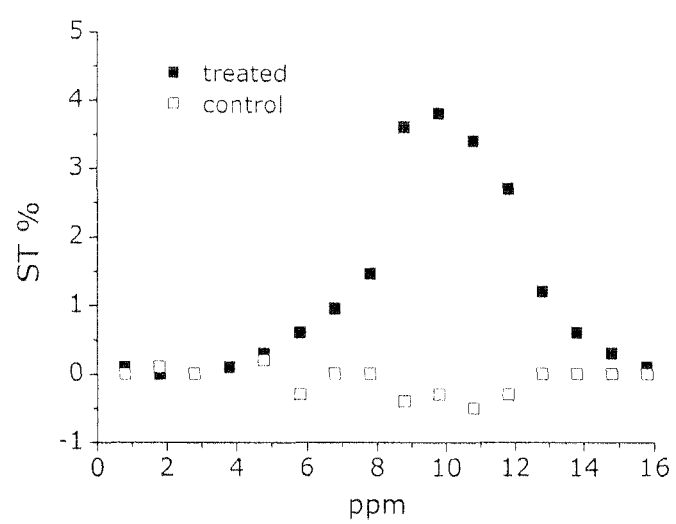

FIG. 19 reports the ST spectra of the two cellular pellets of Example 7, including, the first HUVEC cells treated with the biotinilated LIPOCEST and the second only HUVEC cells as control (7 T, irrad. pulse: rectangular, irrad. power 12 μT, irrad. time 2 s, 293 K).

Figure 20:
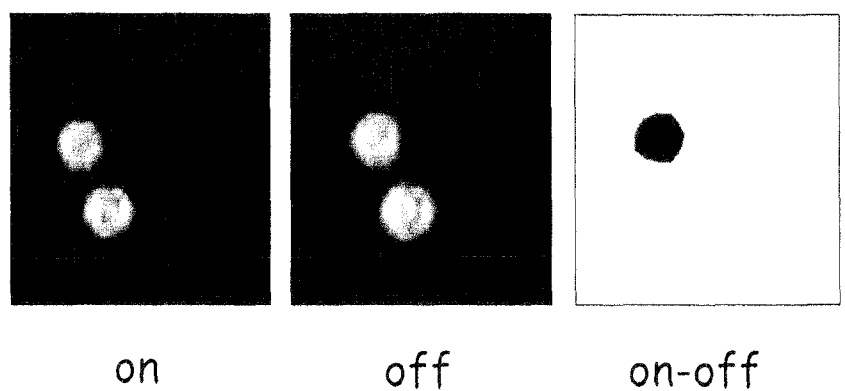

FIG. 20 reports the CEST-MR images registered for the two cellular pellets of example 7, [on-(irradiation at 10 ppm from bulk water), off-(irradiation at −10 ppm from bulk water), and (on-off)] of the phantom made of two capillaries containing two cellular pellets.

DETAILED DESCRIPTION OF THE INVENTION

The present invention relates to novel therapeutic or diagnostic agents comprising cyclic peptide derivatives able to selectively bind to integrin receptors. In particular, it is a first object of the invention a compound of formula (III)

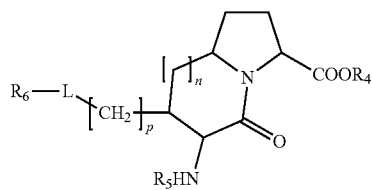

(III)

wherein
n is 1 or 2,
p is an integer between 1 and 5,
$R_4$ and $R_5$ together constitute the sequence Asp-Gly-Arg,
$R_6$ is a biologically active moiety,
L is a group (i) —CONH—, (ii) —NHCONH—, (iii) —NHCSNH—, a group of formula

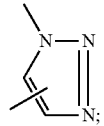

(iv)

-continued

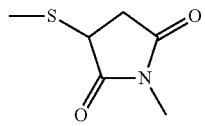

(v)

or it is a divalent linking moiety connecting $R_6$ to the —(CH$_2$) p-bicyclo derivative in formula (III), through any one of the above (i) to (v) groups, their salts, racemic mixtures, individual enantiomers, individual diastereoisomers and mixtures thereof in whatever proportion.

Within the compounds of formula (III), the peptide sequence Asp-Gly-Arg is advantageously bound to compounds in such a manner whereby the carboxyl group is attached to the aminoacid arginine, and the amino group is attached to aspartic acid.

According to preferred embodiment of the invention, p is 1 and n is 1.

According to another preferred embodiment of the invention, p is 1 and n is 2.

According to another preferred embodiment of the invention, within the compounds of formula (III), L is a group from (i) to (v).

As formerly reported, the compounds of the invention are able to selectively bind to integrin receptors, in particular αvβ3 and αvβ5 integrins overexpressed into angiogenic tissues. These compounds may thus optimally bind a cell surface or an intravascular surface expressing the targeted receptor wherein this results in an optimal selectivity and localization of the biological activity they may express.

Thus, this class of compounds may find application for the diagnosis, prevention and treatment of pathological conditions associated with angiogenesis.

In the present description, unless otherwise provided, with the term "Angiogenesis" as used herein we intend an invasive multi-step process characterized by endothelial cell proliferation, modulation of extracellular matrix (ECM), and cell adhesion and migration, resulting in the formation of new blood vessels and/or in the increase in the vascularity of an organ or tissue of the body.

With the term "angiogenic events or processes" as used herein we intend the events or processes involved in a number of pathological conditions, notably tumor growth and metastasis, and other conditions in which blood vessel proliferation is increased such as diabetic retinopathy, psoriasis and arthropathies.

The term "angiogenic disorders", angiogenic diseases" and "pathological conditions associated with angiogenesis" are used herein interchangeably to referrer to clinical conditions involving up-regulation of an angiogenic process leading to excessive blood vessel formation. These conditions include, but are not limited to, cancer, psoriasis, atherosclerosis, restenosis, a number of inflammatory disorders such as, for example, rheumatoid arthritis, and ocular neovascularization leading, in most cases to diabetic retinopathies, neovascular glaucoma, age-related macular degeneration or retinal vein occlusion.

The term "integrin", as used herein, refers to any of the many cell surface receptor proteins, also known as adhesion protein receptors, which bind extracellular matrix ligand or other cell adhesion protein ligands and thereby mediate cell-cell and cell-matrix adhesion processes. Integrins constitute a superfamily of membrane receptors that are encoded by genes belonging to a gene superfamily and are typically composed of heterodynamic transmembrane glycoproteins containing an α- and a β-subunit. Members of an integrin subfamily have a common β subunit, which can combine with different α subunits to form adhesion protein receptors with different specificities. Among the known α subunits, the α$_v$ subunit seems to be the most promiscuous, forming heterodimers with six different β subunits. Integrin $α_v$ include, for example, the receptors $α_vβ_3$ and $α_vβ_5$.

With the term "integrin binding moiety", as used herein, we intend an integrin-inhibiting moiety that specifically acts by binding to integrins, thereby precluding, reversing, inhibiting or otherwise interfering with the binding of integrins to their endogenous ligands. Preferably, integrin binding moieties exhibit a high binding affinity and specificity for $α_v$ integrins; more preferably, for the integrins $α_vβ_3$ and/or $α_vβ_5$; most preferably for the $α_vβ_3$ integrin. When an integrin binding moiety is part of a molecule, it confers its property to the molecule, and the said molecule become "targeted" to integrins, i.e. this molecule specifically and efficiently binds to integrins. The binding between integrins and an integrin binding moiety may be covalent or non-covalent, including, in this last case, hydrophobic interactions, electrostatic interactions, Van der Waals interactions, hydrogen bonding etc. Most often the binding is non-covalent.

With the term "integrin antagonist" and "integrin inhibitor" as used herein interchangeably we intend molecules, agents, or compounds able to inhibiting the biological activity of integrins.

With the term "binding affinity" and "affinity" as used herein interchangeably, we refer to the level of attraction between molecular entities. Affinity can be expressed quantitatively as a dissociation constant ($K_d$) or its inverse, the association constant ($K_a$). In the context of this invention, as reported below, two types of affinity are considered: (a) the affinity of an integrin binding moiety for integrins and (b) the affinity of metal chelates moiety for a transition metal or another metal entity.

Within the compounds of formula (III), $R_6$ designates a biologically active moiety.

With the term "biologically active molecule", as used herein, we intend any therapeutically or diagnostically effective molecule, a sugar, a drug, a phospholipid or lipid moiety, a biotin or an avidin residue that is linked to the targeting moiety through (L).

According to an aspect of the invention, $R_6$ represents a therapeutically or diagnostically effective molecule.

In a preferred embodiment of the invention $R_6$ represents an imaging detectable moiety.

With the term "imaging detectable moiety" and "imaging moiety" as used herein interchangeably we intend any moiety detectable by imaging procedures, that is to say any moiety able to provide, to improve or, in any way, to advantageously modify the signal detected by an imaging diagnostic technique today in use including, for instance, magnetic resonance imaging, radioimaging, ultrasound imaging, x-ray imaging, light imaging, thus enabling the registration of diagnostically useful, preferably contrasted, images when used in association with the said techniques. Suitable examples of the said imaging detectable moieties include, for instance, chelated gamma ray or positron emitting radionuclides; paramagnetic metal ions in the form of chelated or polychelated complexes as well as of micellar systems, liposomes and microspheres; magnetic, diamagnetic or superparamagnetic coated particles, microparticles, nanoparticles; X-ray absorbing agents including atoms of atomic number higher than 20; bubbles, microbubbles balloons and microemulsions including biocompatible gas; a dye molecule; a fluorescent molecule; a phosphorescent molecule; a molecule absorbing in the UV spectrum; a quantum dot; a molecule capable of absorption within near or far infrared radiations; optionally coated particles, microparticles and nanoparticles including perfluorocarbons and, in general, all moieties which generate a detectable substance.

A wide range of materials detectable by diagnostic imaging modalities is known in the art and the imaging modality to be used may be selected according to the imaging detectable moiety the diagnostic compounds of the invention include.

With the term "chelator", "metal chelating ligand" and "chelating ligand" as used herein interchangeably we intend chemical moieties, agents, compounds, or molecules characterized by the presence of polar groups able to a form a complex containing more than one coordinate bond with a transition metal or another metal entity. In a preferred aspect of the invention the said chelating ligand includes cyclic or linear polyamino polycarboxylic or phosphonic acids.

With the term "contrast imaging agent" or "contrast agent" as used herein, we refer to any detectable entity that can be used to in vitro or in vivo visualize or detect a biological element including cells, biological fluids and biological tissues originating from a live mammal patient, and preferably, human patient, as well as human body organ, regions or tissues affected by angiogenesis when the said detectable entity are used in association with a suitable diagnostic imaging technique.

With the term "metal entity" as used herein we intend a paramagnetic metal ion that is detectable by imaging techniques such as Magnetic Resonance Imaging (MRI), or to a radionuclide that is detectable by imaging techniques such as Single Photon Emission Computed Tomography (SPECT) and Positron Emission Tomography (PET).

MRI Contrast Agents

As formerly reported, and according to a preferred embodiment of the invention, within the compounds of formula (III) $R_6$ is an imaging detectable moiety.

Even more preferably, $R_6$ represents one or more paramagnetic metal ion in the form of a chelated or polychelated complex, or a suitable physiologically acceptable salt thereof.

Suitable paramagnetic metal ions for use in the present invention include any of the paramagnetic metal ions known in the art as contrast enhancers in MRI and easily incorporated into chelating or polychelating moieties.

Preferably, the paramagnetic metal ion is selected from the following: $Fe(^{2+})$, $Fe(^{3+})$, $Cu(^{2+})$, $Ni(^{2+})$, $Rh(^{2+})$, $Co(^{2+})$, $Cr(3+)$, $Gd(^{3+})$, $Eu(^{3+})$, $Dy(^{3+})$, $Tb(^{3+})$, $Pm(^{3+})$, $Nd(^{3+})$, $Tm(^{3+})$, $Ce(^{3+})$, $Y(^{3+})$, $Ho(^{3+})$, $Er(^{3+})$, $La(^{3+})$, $Yb(^{3+})$, $Mn(^{3+})$, $Mn(^{2+})$. More preferably, the paramagnetic metal ion is $Gd(^{3+})$.

A suitable metal chelating moiety may be any metal chelator, polychelator and metal complexing molecule that is able to bind with high affinity the said paramagnetic metal ions so as to provide highly stable, non-toxic, paramagnetic chelated complexes still leaving at least one coordination site open for a water molecule. A number of either linear or cyclic metal chelating moieties are known in the art including acids, for instance bearing methylene phosphoric acidic groups, methylene hydroxamic acidic groups, carboxyethylidene groups, or carboxymethylene groups.

Examples of chelators include, but are not limited to, diethylenetriamine pentaacetic acid (DTPA) and derivatide thereof including, for example, benzo-DTPA, dibenzo-DTPA, phenyl-DTPA, diphenyl-DTPA, benzyl-DTPA, and dibenzyl DTPA; 1,4,7,10-tetraazacyclotetradecane-1,4,7,10-tetraacetic acid (DOTA); 1-substituted 1,4,7,-tricarboxymethyl 1,4,7,10 teraazacyclododecane triacetic acid (DO3A); 1,4,7,10-tetraazacyclotetradecane-1,4,7,10-tetra(methyl tetraacetic acid (DOTMA), ethylenediaminetetraacetic acid (EDTA); and 1,4,8,11-tetraazacyclotetradecane-1,4,8,11-tetraacetic acid (TETA). Additional chelating ligands are ethylenebis-(2-hydroxy-phenylglycine) (EHPG) and derivatives thereof, including 5-Cl-EHPG, 5-Br-EHPG, 5-Me-EHPG, 5-t-Bu-EHPG, and 5-sec-Bu-EHPG; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N''-triacetic acid, benzo-TETA, benzo-DOTMA, and benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); derivatives of 1,5,10-N,N',N''-tris(2,3-dihydroxybenzoyl)-tricatecholate (LI-CAM) and 1,3,5-N,N',N''-tris(2,3-dihydroxybenzoyl) aminomethylbenzene (MECAM). Preferred chelators and chelates contemplated by the present invention are further described in WO 2005/062828, WO2003/008390 and EP1155023 that are incorporated herein by reference.

Further examples of preferred chelators according to the present invention are included in FIGS. 8A to 8C together with suitable bibliographic references concerning their preparation.

Polychelators or polychelating molecules or moieties, according to the present invention, include more than 50, preferably more than 100, and even more preferably more than 300 chelating units, suitably linked to a polymeric chain. Suitable examples of the said polychelators comprise, but are not limited to, suitably functionalized poly-amino acid chains including polylysine, polyalbumine and poly-saccharidic chains including polydextranes, dendrimers, and polymeric and copolymeric derivatives linking up to 300 chelating units. See, for a reference to the said polychelating units, WO 91/05762, U.S. Pat. No. 5,958,373, WO 90/12050, WO94/27498, EP0888129, U.S. Pat. No. 600,934, U.S. Pat. No. 5,517,993, WO93/06868, US20050085417, EP1151997, WO9306148, U.S. Pat. No. 6,274,713, WO 95/24225, U.S. Pat. No. 5,679,810, EP0607222, WO9507270, EP 0000378, WO9105762, WO 2003/014157, EP 0722442, WO 2003/014157, WO 97/01359, and WO 97/32862.

Examples of preferred MRI contrast agents of the invention comprise

Chelated complex 1

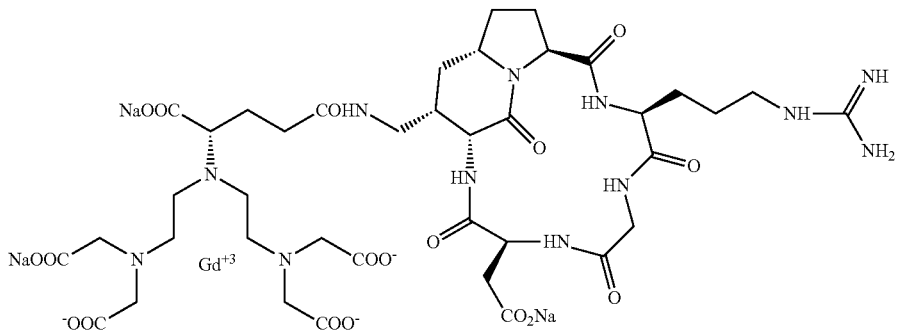

Chelated complex 2

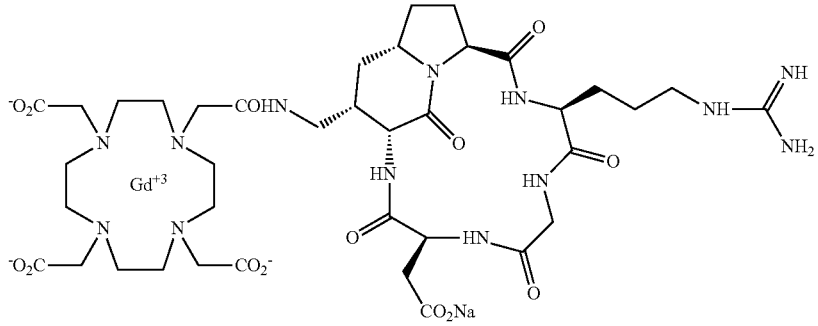

Chelated complex 3

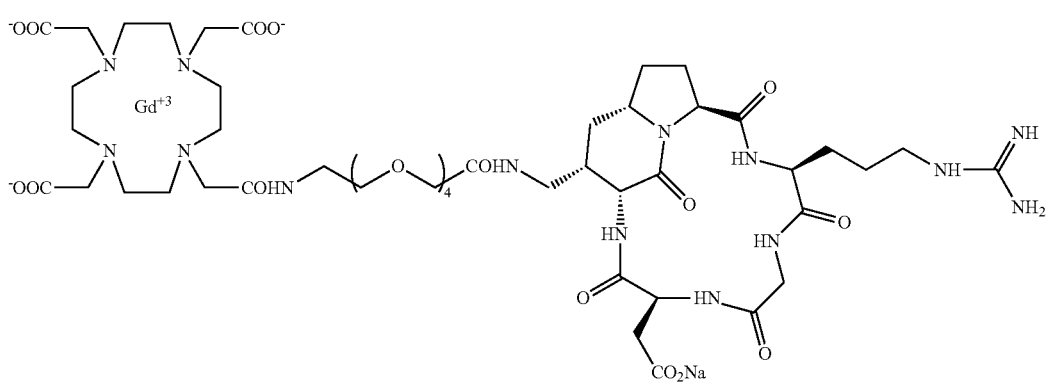

Therapeutically Effective Agents

In a further aspect $R_6$ is a therapeutic agent or a toxin for selective killing and/or inhibiting the growth of cancer cells, or, when required, for inhibiting or promoting the growth of normal tissues.

In a preferred embodiment of the invention, $R_6$ is a suitably chelated radioactive metal ion that emits ionizing radiations such as beta particles, alpha particles and Auger or Coster-Kroning electrons, thus providing a radiopharmaceutical agent able to target the said radioactive metal ion to the tumor neovasculature; hence, the beta or alpha-particles emitting radioisotope emits a cytotoxic amount of ionizing radiation causing the cell death.

For therapeutic purposes, the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au.

These pharmaceutical agents of the invention comprising a particle emitting radioactive metal ion are also useful for treating rheumatoid arthritis wherein the growth of a highly vascularized pannus is caused by the excessive production of angiogenic factors by infiltrating macrophages, immune cells, or inflammatory cells. The locally concentrated emission of cytotoxic radiation provided by the therapeutic agents of the invention thus promote the destruction of the new angiogenic vasculature, thus allowing the therapeutic treatment of this inflammatory process.

Nuclear Imaging (Radionuclide Imaging) and Radiotherapy

According to an alternative embodiment of the invention, $R_6$ is a suitably chelate gamma ray or positron emitting radionuclide or a radionuclide for therapy.

Compounds of the invention comprising the said $R_6$ moiety may be used as contrast agents for scintigraphy, PET or SPECT.

Preferred metal radionuclides for use in PET imaging are positron emitting metal ions, such as $^{51}$Mn, $^{52}$Fe, $^{60}$Cu, $^{68}$Ga, $^{72}$As, $^{94m}$Tc, or $^{110}$In.

Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In. For therapeutic purposes, the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au. $^{99m}$Tc is particularly preferred for diagnostic applications because of its low cost, availability, imaging properties, and high specific activity. The nuclear and radioactive properties of $^{99m}$Tc make this isotope an ideal scintigraphic imaging agent. This isotope has a single photon energy of 140 keV and a radioactive half-life of about 6 hours, and is readily available from a $^{99}$Mo-$^{99m}$Tc generator.

The metal radionuclides may be chelated by, e.g., linear, macrocyclic, terpyridine, and $N_3S$, $N_2S_2$, or $N_4$ chelants (see also U.S. Pat. No. 5,367,080, U.S. Pat. No. 5,364,613, U.S. Pat. No. 5,021,556, U.S. Pat. No. 5,075,099, U.S. Pat. No. 5,886,142), and other chelators known in the art including, but not limited to, HYNIC, DTPA, EDTA, DOTA, TETA, and bisamino bisthiol (BAT) chelators (see also U.S. Pat. No. 5,720,934). For example, $N_4$ chelators are described in U.S. Pat. Nos. 6,143,274; 6,093,382; 5,608,110; 5,665,329; 5,656,254; and 5,688,487. Certain $N_3S$ chelators are described in PCT/CA94/00395, PCT/CA94/00479, PCT/CA95/00249 and in U.S. Pat. Nos. 5,662,885; 5,976,495; and 5,780,006.

The chelator may also include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in Liu and Edwards, *Chem Rev*, 1999, 99, 2235-2268 and references therein.

The chelator may also include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

Preferred metal chelators include those of FIG. 8 from 8A to 8C (for $^{111}$In and lanthanides such as paramagnetic $Gd^{3+}$ and radioactive lanthanides, such as, for example $^{177}$Lu, $^{90}$Y, $^{153}$Sm, and $^{166}$Ho and those of FIG. 9 from 9A to 9B (for radioactive $^{99m}$Tc, $^{186}$Re, and $^{188}$Re). Particularly preferred metal chelators are those of formula 17-21 for $Gd^{3+}$ and radioactive lanthanides, and from 22 to 33 for radioactive $^{99m}$Tc, $^{186}$Re, and $^{188}$Re. These and other metal chelating groups are described in U.S. Pat. Nos. 6,093,382 and 5,608,110; U.S. Pat. No. 6,143,274; U.S. Pat. Nos. 5,627,286 and 6,093,382; U.S. Pat. Nos. 5,662,885, 5,780,006, and 5,976,495 which are incorporated by reference herein in their entirety. Additionally, the chelating formula 19 is described in, for example, U.S. Pat. No. 6,143,274; the chelating group of formula 31 and 32 are described in U.S. Pat. Nos. 5,627,286 and 6,093,382; and the chelating group of formula 33 is described in, for example, U.S. Pat. Nos. 5,662,885, 5,780,006, and 5,976,495.

In the above Formulae 17 and 18, R is alkyl, preferably methyl. In the above Formulae 31 and 32 X is either $CH_2$ or O, Y is either $C_1$-$C_{10}$ branched or unbranched alkyl; Y is aryl, aryloxy, arylamino, arylaminoacyl; Y is arylkyl—where the alkyl group or groups attached to the aryl group are $C_1$-$C_{10}$ branched or unbranched alkyl groups, $C_1$-$C_{10}$ branched or unbranched hydroxy or polyhydroxyalkyl groups or polyalkoxyalkyl or polyhydroxy-polyalkoxyalkyl groups, J is C(=O), OC(=O)—, $SO_2$, NC(=O)—, NC(=S)—, N(Y), NC(=NCH$_3$)—, NC(=NH)—, N=N—, homopolyamides or heteropolyamines derived from synthetic or naturally occurring amino acids; all where n is 1-100. Other variants of these structures are described, for example, in U.S. Pat. No. 6,093,382. The disclosures of each of the foregoing patents, applications and references are incorporated by reference herein, in their entirety.

In a still further embodiment $R_6$ is an optionally labelled sugar moiety for use, when labelled, in PET Imaging. In particular $R_6$ may represent a sugar moiety labeled by halogenation with radionuclides, such as, $^{124}$I, $^{125}$I, $^{131}$I, $^{123}$I, $^{77}$Br, and $^{76}$Br wherein $^{18}$F is preferred.

Optical Imaging, Sonoluminescence or Photoacoustic Imaging

In one further preferred embodiment, $R_6$ represents a dye molecule; a fluorescent molecule; a phosphorescent molecule; a molecule absorbing in the UV spectrum; a quantum dot; or a molecule capable of absorption of near or far infrared radiations. Optical parameters to be detected in the preparation of an image may include, e.g., transmitted radiation, absorption, fluorescent or phosphorescent emission, light reflection, changes in absorbance amplitude or maxima, and elastically scattered radiation. For example, biological tissue is relatively translucent to light in the near infrared (NIR) wavelength range of 650-1000 nm. NIR radiation can penetrate tissue up to several centimeters, permitting the use of the diagnostic agents of the invention comprising a NIR moiety to image target-containing tissue in vivo.

Near infrared dye may include, cyanine or indocyanine derivatives, such as, for example, Cy5.5, IRDye800, indocyanine green (ICG), indocyanine green derivatives including the tetrasulfonic acid substituted indocyanine green (TS-ICG), and combination thereof.

In another embodiment, the compounds of the invention may be conjugated with photolabels, such as optical dyes, including organic chromophores or fluorophores, having extensively conjugated and hence delocalized ring systems and having absorption or emission maxima in the range of 400-1500 nm. The compounds of the invention may alternatively be derivatized with a bioluminescent molecule. The preferred range of absorption maxima for photolabels is between 600 and 1000 nm to minimize interference with the signal from hemoglobin. Preferably, photoabsorption labels have large molar absorptivities, e.g. $>10^5$ cm$^{-1}$M$^{-1}$, while fluorescent optical dyes will have high quantum yields. Examples of optical dyes include, but are not limited, to those described in WO 98/18497, WO 98/18496, WO 98/18495, WO 98/18498, WO 98/53857, WO 96/17628, WO 97/18841, WO 96/23524, WO 98/47538, and references cited therein. For example, the photolabels may be covalently linked directly to the targeting moieties of the invention, or they may be linked thereto via a linking moiety, as described previously.

After injection of the optically-labeled diagnostic derivative according to the invention, the patient is scanned with one or more light sources (e.g., a laser) in the wavelength range appropriate for the photolabel employed in the agent. The light used may be monochromatic or polychromatic and continuous or pulsed. Transmitted, scattered, or reflected light is detected via a photodetector tuned to one or multiple wavelengths to determine the location of target-containing tissue (e.g. angiogenic tissue) in the subject. Changes in the optical parameter may be monitored over time to detect accumulation of the optically-labeled reagent at the target site. Standard image processing and detecting devices may be used in conjunction with the optical imaging reagents of the present invention.

The optical imaging agents described above may also be used for acousto-optical or sonoluminescent imaging performed with optically-labeled imaging agents (see, f.i., U.S. Pat. No. 5,171,298, WO 98/57666, and references therein). In acousto-optical imaging, ultrasound radiation is applied to the subject and affects the optical parameters of the transmitted, emitted, or reflected light. In sonoluminescent imaging, the applied ultrasound actually generates the light detected. Suitable imaging methods using such techniques are described in WO 98/57666, which is hereby incorporated by reference in its entirety.

Special Purpose Molecules

In a still further embodiment $R_6$ is a special purpose molecule. As special purpose molecule are defined some molecules that may or may not have a direct role in the interaction with a detection system, but have a functional attribute that facilitates the use of the peptidic constructs in some way. Such molecules, when appended to the peptidic construct, for example, may enable the incorporation of the peptidic construct into larger arrays of molecules (such as supramolecular constructs) which can conversely be detected by equipment or apparatus employed for detection of signals, whether by presence or absence of the signal, a change in signal intensity, reflection of a signal or a derivative signal during or after a period of irradiation by the equipment or apparatus.

Thus, in one embodiment, $R_6$ is a phospholipid or lipid moiety consenting to the cyclic peptides of the invention linked thereto to be incorporated, upon agitation (e.g., shaking, stirring, etc.) into liposomes, or even micellar systems, vesicles or microspheres suitably including, for example, metal entities and particularly, paramagnetic metal ions, or an echogenic gas, thus providing a macromolecular compound for use in MRI or ultrasound imaging including an high number of the said targeting moiety on its surface. Together with the peptidomimetic compounds of the invention comprising a lipid moiety these macromolecular system may further include surfactants, sphingolipids, oligolipids, phospholipids, proteins, polypeptides, carbohydrates, and synthetic or natural polymeric materials. See, e.g., WO 98/53857, WO 98/18498, WO 98/18495, WO 98/18497, WO 98/18496, and WO 98/18501 incorporated herein by reference in their entirety.

A "lipid" as used herein, is a synthetic or naturally-occurring amphipatic compound which comprises a hydrophilic component and a hydrophobic component. Lipid includes, for example, fatty acids, neutral fats, phosphatides, glycolipids, aliphatic alcohols and waxes, terpenes and steroids.

Examples of classes of suitable lipids constituting the $R_6$ moiety of the invention include: phosphatidylcholines, such as dioleoylphosphatidylcholine, dimyristoylphosphatidylcholine, dipalmitoyl-phosphatidylcholine and diasteroylphosphatidylcholine; phosphatidyl-ethanolamines, such as dipalmitoylphosphatidylethanol amine, dioleoylphosphatidylethanolamine and N-succinil-dioleoylphosphatidylethanolamine; phosphatidylserine; dipalmitoylphosphatidylserine; phosphatidylglycerols; sphingolipids; glycolipids such as ganglioside GM1; glucolips; sulphatides; phosphatidic acid, such as dipalmitoyl phosphatidic acid ("DPPA"); palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isostearic fatty acids; cholesterol and cholesterol derivatives, such as cholesterol hemisuccinate, cholesterol sulphate, and cholesteryl-(4-trimethylammonio)-butanoate; polyoxyethylene fatty acids asters, polyoxyethylene fatty acids alcohols; polyoxyethylene fatty acids alcohol ethers; polyoxyethylated sorbitan fatty acid esters, glycerol polyethylene glycol oxy-stearate; glycerol polyethylene glycol ricinoleate; ethoxylated soybean sterols; ethoxylated castor oil; polyoxyethylene polyoxypropylene fatty acid polymers; polyoxyethylene fatty acid stearates; 1,2-dioleoyl-sn-glycerol; 1,2-dipalmitoyl-sn-3-succinylglycerol; 1,3-dipalmitoyl-2-succinylglycerol; 1-hexadecyl-2-palmitoyl-glycerophosphoethanolamina; N-Succinyl-dioctadecylamine; palmitoylhomocysteine; lauryltrimethylammonium bromide; cetyltrimethyl-ammonium bromide; myristyltrimethylammonium bromide; alkyldimethylbenzylammonium chloride; wherein alkyl is a $C_{12}$, $C_{14}$, $C_{16}$ alkyl; benzyldimethyldodecylammonium bromide; benzyldimethyldodecyl ammonium chloride; benzyldimethylhexadecylammonium bromide; benzyldimethylhexadecylammonium chloride; benzyldimethyltetradecyl ammonium bromide; benzyldimethyltetradecyl ammonium chloride; cetyldimethylethylammonium chloride; cetylpyridinium bromide; cetylpyridinium chloride; N-[1,2,3-dioleoyloxy)-propyl]-N,N,N-trimethylammonium chloride (DOTMA); 1,2-dioleoyloxy-3-(trimethylammonium)propane (DOTAP); and 1,2-dioleoyl-c-(4'-trimethylammonium)-butanoyl-sn-glycerol (DOTB).

With the term "vesicle", as used herein, we refer to a spherical entity which is characterized by the presence of an internal void. Preferred vesicles are formulated from lipids, including the various lipids described herein. In any given vesicle, the lipids may be in the form of monolayer or bilayer, and the mono- or bilayer lipids may be used to form one or more of mono- or bilayers. The lipid vesicles described herein include such entities commonly referred to as liposomes, micelles, bubbles, microbubbles, microspheres and the like. The internal void of the vesicles may be filled with a liquid, including, for example, an aqueous liquid, a gas, a gaseous precursor, and/or a solid or solute material, including for example, a bioactive agent.

Liposomes, as used herein, refers to a generally spherical cluster or aggregate of amphipatic compounds, including lipid compounds, typically in the form of one or more concentric layers, for example, bilayers. They may also be referred to herein as lipid vesicles.

The term bubbles as used herein refers to a vesicles which are generally characterized by the presence of one or more membranes o walls surrounding an internal void that is filled with a gas or a precursor thereto. Exemplary bubbles includes, for example, micelles, liposomes, and the like.

Microspheres as used herein, is preferably a sphere of less than or equal to 10 microns.

Thus, in one embodiment the invention relates to a macromolecular system in the form of liposomes, micelles, microemulsions, bubbles, microbubbles, microballons or microspheres comprising a compound of the invention wherein $R_6$ is a phospholipid or a lipid moiety.

In one preferred embodiment, the said macromolecular system is a paramagnetic liposome, i.e. a liposome containing in its cavity $Gd^{3+}$ ions, for use in MRI of integrin $\alpha_v\beta_3$ expression.

In a further preferred embodiment the said macromolecular system is a LIPOCEST.

In another preferred embodiment, the said macromolecular system is a gas containing vesicle for use in ultrasound imaging.

In an additional embodiment the said gas filled vesicles are gas-containing microparticle.

Ultrasound Contrast Agents, in a further embodiment $R_6$ represents any material including surfactants, sphingolipids, oligolipids, phospholipids, proteins, polypeptides, carbohydrates, and synthetic or natural polymeric materials coupled to a peptidic derivative incorporated into a gas filled vesicle, i.e. a microbubbles, microballoons, microspheres or emulsions containing a liquid or gas moiety which functions as the detectable label (e.g., an echogenic gas or material capable of generating an echogenic gas).

Preferably, $R_6$ represents, a phospholipid or lipid moiety according to the above definition coupled to a peptidic derivative incorporated into a gas filled vesicle.

In one embodiment the said gas filled vesicles are bubbles or microballoons.

The preferred microballoons have an envelope including a biodegradable physiologically compatible polymer or a biodegradable solid lipid. The polymers useful for the preparation of the microballoons of the present invention can be selected from the biodegradable physiologically compatible polymers, such as any of those described in any of the following patents: EP 458745, U.S. Pat. No. 5,711,933, U.S. Pat. No. 5,840,275, EP 554213, U.S. Pat. No. 5,413,774 and U.S. Pat. No. 5,578,292, the entire contents of which are incorporated herein by reference. In particular, the polymer can be selected from biodegradable physiologically compatible polymers, such as polysaccharides of low water solubility, polylactides and polyglycolides and their copolymers, copolymers of lactides and lactones such as ε-caprolactone, γ-valerolactone and polypeptides. Other suitable polymers include poly(ortho)esters (see, e.g., U.S. Pat. No. 4,093,709; U.S. Pat. No. 4,131,648; U.S. Pat. No. 4,138,344; U.S. Pat. No. 4,180,646); polylactic and polyglycolic acid and their copolymers, for instance DEXON (see J. Heller, Biomaterials 1 (1980), 51; poly(DL-lactide-co-ε-caprolactone), poly(DL-lactide-co-γ-valerolactone), poly(DL-lactide-co-γ-butyrolactone), polyalkylcyanoacrylates; polyamides, polyhydroxybutyrate; poly-dioxanone; poly-β-aminoketones (A. S. Angeloni, P. Ferruti, M. Tramontini and M. Casolaro, The Mannich bases in polymer synthesis: 3. Reduction of poly(beta-aminoketone)s to poly(gamma-aminoalcohol)s and their N-alkylation to poly(gamma-hydroxyquaternary ammonium salt)s, Polymer 23 pp 1693-1697 (1982)); polyphosphazenes (Allcock, Harry R., Polyphosphazenes: new polymers with inorganic backbone atoms (Science 193(4259), 1214-19 (1976)) and polyanhydrides. The microballoons of the present invention can also be prepared according to the methods of WO-A-96/15815, incorporated herein by reference, where the microballoons are made from a biodegradable membrane comprising biodegradable lipids, preferably selected from mono- di-, tri-glycerides, fatty acids, sterols, waxes and mixtures thereof. Preferred lipids are di- or tri-glycerides, e.g. di- or tri-myristin, -palmityn or -stearin in particular tripalmitin or tristearin.

The microballoons may employ any of the gases disclosed herein or known to the skilled artisan.

Any biocompatible gas may be used in the vesicular contrast agents of the invention. The term "gas" as used herein includes any substances (including mixtures) substantially in gaseous form at the normal human body temperature.

The said gas may thus include, for example, air; nitrogen; oxygen; $CO_2$; argon; xenon or krypton, fluorinated gases (including for example, perfluorocarbons, $SF_6$, $SeF_6$) a low molecular weight hydrocarbon (e.g. containing from 1 to 7 carbon atoms), for example, an alkane such as methane, ethane, propane, butane or pentane, a cycloalkane such as cyclopropane, cyclobutane or cyclopentene, an alkene such as ethylene, propene, propadiene or butene, or an alkyne such as acetylene or propyne and/or mixtures thereof. However, fluorinated gases are preferred. Fluorinated gases include materials which contain at least one fluorine atom. Examples include, but are not limited to compounds such as $SF_6$, freons (organic compounds containing one or more carbon atoms and fluorine, i.e. $CF_4$, $C_2F_6$, $C_3F_8$, $C_4F_8$, $C_4F_{10}$, $CBrF_3$, $CCl_2F_2$, $C_2ClF_5$ and $CBrClF_2$) and perfluorocarbons. The term perfluorocarbon refers to compounds containing only carbon and fluorine atoms. Such compounds include saturated, unsaturated, and cyclic perfluorocarbons. The saturated perfluorocarbons, which are preferred, have the formula $C_nF_{n+2}$, where n is from 1 to 12, preferably from 2 to 10, more preferably from 3 to 8 and most preferably from 3 to 6. Suitable perfluorocarbons include, but are not limited to, $CF_4$, $C_2F_6$, $C_3F_8$, $C_4F_8$, $C_4F_{10}$, $C_5F_{12}$, $C_6F_{12}$, $C_7F_{14}$, $C_8F_{18}$ and $C_9F_{20}$. Most preferably, the gas or gas mixture comprises $SF_6$ or a perfluorocarbon selected from the group consisting of $C_3F_8$, $C_4F_8$, $C_4F_{10}$, $CF_{12}$, $C_6F_{12}$, $C_7F_{14}$, $C_8F_{18}$, with $C_4F_{10}$ being particularly preferred.

In certain circumstances it may be desirable to include a precursor to a gaseous substance (e.g., a material that is capable of being converted to a gas in vivo, often referred to as a "gas precursor"). Preferably, the gas precursor and the gas it produces are physiologically acceptable. The gas precursor may be pH-activated, photo-activated, temperature-activated, etc. For example, certain perfluorocarbons may be used as temperature-activated gas precursors. These perfluorocarbons, such as, e.g., perfluoropentane, have a liquid/gas phase transition temperature above room temperature (or the temperature at which the agents are produced and/or stored) but below body temperature; thus, they undergo a phase shift and are converted to a gas within the human body.

In one further embodiment, $R_6$ is a biotin moiety or a biotinylated moiety consenting to a cyclic peptides of the invention linked thereto to be appended to a suitably functionalized macromolecular aggregate that comprise, in its internal void, for example, metal entities or an echogenic gas, thus providing a detectable multifunctionalized macromolecular aggregate.

The multifunctionalized compounds obtained exploiting the said special purpose $R_6$ moieties comprise an high number of targeting units of the invention on thereof surface. Accordingly, they may optimally bind a cell surface or an intravascular surface expressing the targeted receptor and, when successfully bound to the angiogenic target selectively addressed by the peptidic moieties they comprise, then the said derivative may be detected by use of a suitable imaging technique depending on what the vesicle cavity has been filled, thereby allowing diagnosis or prognosis of a disease condition.

Liposomes, for example, may also be employed to facilitate delivery of encapsulated solutions of chemotherapeutic agents. In this case, the phospholipid-peptide conjugates of the invention can be incorporated into liposomes, thereby enabling the liposome to target a specific integrin receptors and release the therapeutic in higher concentration and proximity to the targeted region.

Suitable examples or the this multifunctionalized system are prepared according to known techniques (see, e.g., Sipkins, D. A. et al., 1998, Nat. Med. 4:623-626 and cited references). Best disclosure of these compounds and thereof preparations are comprised in the experimental section below.

Divalent Linking Moiety

With the term "divalent linking moiety", when referring to (L) in formula (III), we intend a bifunctional moiety including at least two binding groups for the attachment with the remaining portions of the molecule, for instance through cross-linking or coupling reactions.

Typically, any linking moiety (L) may be represented through the difunctional groups from (i) to (v) or it can be represented by a divalent linking moiety connecting $R_6$ to the —(CH$_2$)p-bicyclo derivative in formula (III), comprising two of the above (i) to (v) groups, as ending groups.

As a non limiting example, within a compound of formula (III) being prepared as schematically indicated below:

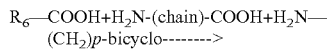

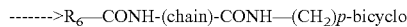

the linking moiety (L) is just the divalent moiety in bold, connecting $R_6$ to the —(CH$_2$)p-bicyclo residue, this latter herewith shortly referred to as the targeting moiety or unit.

Besides acting as a branching system between $R_6$ and the targeting unit, the linking moiety L may provide for a proper distance or "space" between the biologically active moiety $R_6$ and the targeting unit of the compound of the invention. In fact, an optimal distance between these two units may represent an important factor so as to get and maintain the targeting capability of the cyclic peptide of the invention. It is well known, in fact, that any improper or anyway sub-optimal derivatization of a peptidic-based targeting moiety may often result in a significant loss of the peptide affinity for the targeted objective.

Moreover, in a further and equally relevant view of the invention, the linkers (L) may significantly contribute to improve the hydrophilicity of the diagnostic or therapeutic agent, thus providing the desired pharmacokinetic or pharmacodynamic profile of the compound of formula (III).

Accordingly, L may include, without limitations: substituted or unsubstituted, either saturated or unsaturated, straight or branched alkyl chains; peptides from straight, branched or cyclic amino acid chains composed from a single amino acid or from different amino acids (e.g., extensions of the N- or C-terminus of the binding moieties); derivatized or underivatized polyethylene glycol, polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; glycosylated amino acid residues, alternating block copolymers; malonic, succinic, glutaric, adipic and pimelic acids; caproic acid; simple diamines and dialcohols; any of the other linkers disclosed herein; or any other simple polymeric linker known in the art (see, e.g., WO 98/18497, WO 98/18496).

From the above definitions, it is clear to the skilled person that in case L includes an alkyl chain, for instance a propylene chain —(CH$_2$)$_3$—, the divalent linking moiety L in formula (III) could be represented, just as an example, as

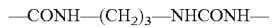

said group bridging the bioactive moiety $R_6$ through the carboxamido group, at one side, and the targeting unit —(CH$_2$) p-bicyclo through the ureido group, at the other side.

Likewise, for instance in the case of L including an amino acid, for example Ala, the divalent linking group L in formula (III) could be represented, as an example, as

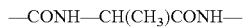

wherein $R_6$ may be connected, via carboxamido, to the amino group of Ala, whilst the targeting unit may be connected, in the present case through carboxamido, to the carboxy group of Ala.

The molecular weight (MW) of the linking moieties L of the invention may be selected, for instance up to about 1000 dalton, preferably up to about 500 and even more preferably up to about 300 dalton.

In addition, it may be desirable to utilize a linking moieties that is biodegradable in vivo so as to provide efficient routes of excretion upon administration of the compounds of the invention, for instance of a diagnostic agent.

Depending upon their location within the linking moieties itself, suitable biodegradable groups can be thus present. Typically, a biodegradable functionality may include an ester, double ester, amide, phosphoester, ether, acetal and ketal functionality.

As an additional example, the linking moiety of the invention may also include homobifunctional or heterobifunctional moieties or suitable combinations thereof.

With the term homobifunctional molecule or moiety, as used herein, we intend a molecule or moiety having at least two reactive functional groups which are the same. With the term heterobifunctional molecule or moiety, as used herein, we intend a molecule or moiety having at least two different reactive groups.

Suitable examples of homobifunctional molecule include, for example, dicarboxylic compounds and suitable derivatives thereof wherein the carboxylic group(s) are in a suitably activated or protected form; a diamine and suitable derivatives thereof wherein the amino group(s) are in a suitably activated o protected form.

Examples of dicarboxylic molecule include the following compounds:

HOOC—Z—COOH where Z can be in the form $(CH_2)_n$ to give compounds such as, e.g, HOOC—$(CH_2)_n$—$CO_2H$ where n=0-10. The group Z can also be an alkyl chain which is mono or polysubstituted by one or more of the following groups: —NH—, —O—, —CO—, —NH(CO)—, —(CO)NH—, —O(CO)—, or —(OC)O— thus resulting in structures like, for instance:

HOOC—$CH_2$—O—$(CH_2)_2$—O—$(CH_2)_2$—O—$CH_2$—COOH

HOOC—$CH_2$—NH—$CH_2$—COOH

HOOC—$(CH_2)_2$—$CO_2$—$(CH_2)_2$—OCO—$(CH_2)_2$—COOH

HOOC—CH(OH)—CH(OH)—COOH

In a further embodiment, the said dicarboxylic molecules can also comprise a substituted aromatic or heterocyclic acid of the form HOOC—Z—COOH, where Z represents the aromatic or heterocyclic nucleus which is the scaffold bearing the two carboxylic groups. Examples of such molecules include, without limitation, benzene-1,4-dicarboxylic acid, biphenyl-1,4'-dicarboxylic acid, (4-carboxymethoxy-phenoxy)-acetic acid, (4'-carboxymethoxy-biphenyl-4-yloxy)-acetic acid, N-methylpyrrole-2,5-dicarboxylic acid, pyridine-2,6-dicarboxylic acid, N-methylpyrrole-2,3-dicarboxylic acid, N-methylpyrrole-2,4-dicarboxylic acid, pyridine 2,3-dicarboxylic acid, pyridine-3,5-dicarboxylic acid, pyridine 3,4-dicarboxylic acid or piperidine 3,5-dicarboxylic acid. The saturated derivatives of the aromatic compounds described above, where Z is now a saturated derivative of the aromatic or heterocyclic Z, can also be employed to provide suitable linkers L according to the present invention.

Examples of homobifunctional diamine molecules include the following:

$NH_2$—$(CH_2)_n$—$NH_2$, where n=0-20; or $NH_2$—$CH_2(CH_2)_j$O—$(CH_2(CH_2)_mO)_n$—$CH_2$—$(CH_2)_p$—$NH_2$, where j=1-20, m=1-2, n=1-100 and p=1-20.

According to an additional embodiment, the linking moieties L may be derived from a substituted aromatic or heterocyclic diamine of the form $NH_2$-Q-Z-Q'—$NH_2$, where Z represents the aromatic or heterocyclic nucleus which is the scaffold bearing the two amino groups; and Q and Q' are:

—$(CH_2)_n$ where n=2-10; or
—$CH_2(CH_2)_f$ where f=1-9; or
—$(CH_2CH_2O)_q(CH_2)_r$— where q=1-10 and r=2-10; or
—$(CH_2)_n$NH—C(=O)— where n=2-10; or
—$(CH_2CH_2O)_q(CH_2)_r$—NH—C(=O)— where q=1-10 and r=2-10;

and where Q and Q' can be the same or different members of the set of moieties described herein.

Clearly, when referring to dicarboxylic or diamine molecules or moieties, previous considerations to the linking group (L) in formula (III) apply as well. Therefore, when referring to a dicarboxylic acid like

HOOC—$CH_2$—O—$(CH_2)_2$—O—$(CH_2)_2$—O—$CH_2$—COOH a divalent linking moiety L could be represented in formula (III), for instance as $R_6$—NHCO—$CH_2$—O—$(CH_2)_2$—O—$(CH_2)_2$—O—$CH_2$—CONH—$(CH_2)$p-bicyclo or, even $R_6$—CONHCO—$CH_2$—O—$(CH_2)_2$—O—$(CH_2)_2$—O—$CH_2$—CONH—$(CH_2)$p-bicyclo.

Analogously, any diamine like $NH_2$—$(CH_2)_n$—$NH_2$ could give rise, in formula (III), to a divalent linking moiety for instance as:

$R_6$—CONH—$(CH_2)_n$—NHCONH—$(CH_2)$p-bicyclo or
$R_6$—NHCONH—$(CH_2)_n$—NHCONH—$(CH_2)$p-bicyclo or
$R_6$—NHCONH—$(CH_2)_n$—NHCSNH—$(CH_2)$p-bicyclo, and the like.

In a further embodiment, the linking moiety of the invention may comprise a suitable mono or bis-imide derivative of the aforementioned bis-amines, wherein maleimido derivatives are particularly preferred.

Examples of heterobifunctional linking moieties may include compounds at least bearing an amino and a carboxylic function as reactive groups.

In a preferred embodiment, the said amino acid molecules are derived from a D or L amino acid, including, as a non limiting example, glycine, lysine, serine, ornithine, 2,3-diaminopropionic acid, or a suitable combination thereof.

In another embodiment, the said amino acids may be suitably glycosylated thus enhancing solubility and binding capability with integrin via aspecific or non-specific interactions involving the glycosydic moiety.

Accordingly, L may optionally include one or more sugar moiety suitably selected from the following: N-acetylgalactoseamine, D-(+)-allose, D-(+)-altrose, D-(+)-glucose, D-(+)-mannose, D-(-)-gulose, D-(-)-idose, D-(+)-galactose, D-(-)-talose, D-(-)-ribose, D-(-)-arabinose, D-(+)-xylose or D-(-)-lyxose for example, linked to a serine, threonine or asparagines residue, and, preferably, serine, through thereof side-chain oxygen via the anomeric carbon.

For additional definitions of possible linking moieties according to the invention see, as an example, the following sections related to the manufacturing process.

The term "pharmaceutically acceptable salt", as used herein, refers to derivatives of the compounds of the invention wherein the parent compound is modified by making the acid or basic groups not yet internally neutralized in the form of non-toxic, stable salts which does not destroy the pharmacological activity of the parent compound. Suitable example of the said salts include: mineral or organic acid salts, of basic residues such as amines; alkali or organic salts of acidic residues such as carboxylic acids; and the like.

Preferred cations of inorganic bases which can be suitably used to salify the compounds of the invention comprise ions of alkali or alkaline-earth metals such as potassium, sodium, calcium or magnesium.

Preferred cations of organic bases comprise, inter alia, those of primary, secondary and tertiary amines such as ethanolamine, diethanolamine, morpholine, glucamine, N-methylglucamine, N,N-dimethylglucamine.

Preferred anions of inorganic acids which can be suitably used to salify the complexes of the invention comprise the ions of halo acids such as chlorides, bromides, iodides or other ions such as sulfate.

Preferred anions of organic acids comprise those of the acids routinely used in pharmaceutical techniques for the salification of basic substances such as, for instance, acetate, succinate, citrate, fumarate, maleate or oxalate.

Preferred cations and anions of amino acids comprise, for example, those of taurine, glycine, lysine, arginine, ornithine or of aspartic and glutamic acids.

The pharmaceutically acceptable salts of the invention may be prepared from the parent compound which contain a basic or acidic moiety by conventional chemical methods. Generally, such salts can be prepared by reacting the free base or acid forms of these compounds with a stoichiometric amount of the appropriate base or acid in an organic solvent or in a mixture of the two.

Multimeric Constructs

In a further embodiment, the present invention relates to novel multimeric constructs including two or more active moieties linked to an anchoring system. Suitable example of the said active moieties include: a targeting moiety, a diagnostically active moiety, a therapeutic agent, a drug, a sugar, a lipid, a biotin residue.

In particular, in a further aspect, the invention relates to novel multimeric targeting constructs that can exploit the avidity and specificity of multivalent interactions with targeted αvβ3 integrins by including at least two cyclic peptides of the invention, an anchoring system and optional linkers and to novel diagnostic or therapeutic compounds including them.

With the term "anchoring system", as used herein, we intend a polifunctional compound containing at least three, optionally protected, equal or different binding sites or functional groups deriving from any polyvalent organic residue which can be aliphatic with open chain, optionally branched, or alicyclic, or heterocyclic containing N, O, and/or S or aromatic or heteroaromatic, or it is a streptavidin or avidin moiety. The terms "functionality" or "functional group", are used herein interchangeably to refer to specific groups of atoms within molecules or moieties that are responsible for the characteristic chemical reactions of those molecules or moieties. In the context of the present invention, the functional group is the specific active part of a binding group allowing cross-linking or coupling reactions.

With the terms "binding group" or "binding unit" or "branching group" as interchangeably used herein we intend a group or unit able to chemically react with a second, suitable, group thus resulting in the chemical conjugation or "binding" thereof.

With the term "protecting group", as used herein, we designates a protective group adapted to preserving the function to which it is bound. Specifically, protective groups are used to preserve amino function or carboxyl function. Appropriate protective groups include for example benzyl, benzyloxycarbonyl, alkyl or benzyl esters, or other substituents commonly used for the protection of such functions, which are well known to those skilled in the art, for example those described in conventional manuals such as T. W. Green, Protective Groups in Organic Synthesis (Wiley, NY 1981).

A "multimeric targeting construct", as used herein, is a multimeric construct comprising two or more cyclic peptide of the invention that thus can exploit the avidity and specificity of multivalent interactions with targeted αvβ3 integrins.

With the term "construct" or "multimeric construct" as used herein interchangeably, we intend a multimeric or oligomeric derivative of an active moiety that includes at least two of the said moieties suitably linked to an anchoring system.

It is therefore an additional object of the invention a compound of formula (IV)

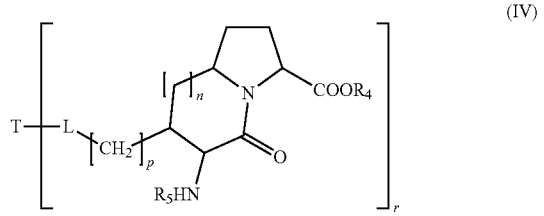

wherein:
$R_4$, $R_5$, n, p, and L, equal or different among them, have the meanings above reported for the compounds of formula (III),
T is an anchoring system, and
r is an integer from 2 to 10, their salts, racemic mixtures, individual enantiomers, individual diastereoisomers and mixtures thereof in whatever proportion.

Preferably, within the compounds of formula (IV), r is an integer from 2 to 5.

Suitable examples of anchoring (T) systems according to the invention include:
(a) N-branched lysine systems (see, f. i., Veprek, P et al., J. Pept. Sci. 5, 5 (1999); 5, 203 (1999),
(b) polycarboxylic derivatives,
(c) polyaminated derivative,
(d) amino acids, Non limiting examples of preferred anchoring systems according to the invention are included in FIGS. 7A, 7B and 7C. All of these compounds are well known in the art and most of them are already marketed. The non-marketed compounds may be easily prepared according to known methods, for example as per the accompanying bibliographic references. The compounds from 20 to 26 are prepared according references cited into EP 1259532.

It is understood to those skilled in the art that lysine derivatives, ornithine, or 2,3-diamino propionic acid may be serially employed to elongate and/or to suitably increase the multiplicity of the said multimers.

An alternative embodiment is represented by the above multimeric constructs wherein the anchoring system (T) is a streptavidin or an avidin/biotin system.

In this respect, it is well known to those skilled in the art, that each avidin molecule or moiety binds, selectively, four biotin molecules or moieties. Thus, for example, an avidin molecule may act as an anchoring system able to bind three units of a biotinylated targeting peptide of the invention, i.e., for example, a compound of formula (III) in which $R_6$ is, or includes, a biotin moiety.

It is therefore an additional object of the invention a compound of formula (V)

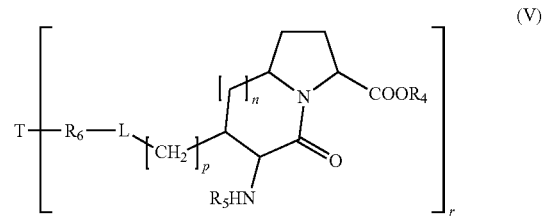

wherein
$R_4$, $R_5$, n, p and L, equal or different among them, have the meanings formerly reported for the compounds of formula (III),
$R_6$ is a biotin moiety,
T is a streptavidin or an avidin moiety,
r is 2 or 3,
their salts, racemic mixtures, individual enantiomers, individual diastereoisomers and mixtures thereof in whatever proportion.

Preferably, within the compounds of formula (V), r is 3.

The compounds of formulae (IV) and (V) possess interesting pharmacological properties, particularly an antagonistic effect towards the αvβ3 and αvβ5 integrins, and display interesting antiangiogenic activities.

A further object of the present invention is hence the use of these compounds for the preparation of drugs, particularly useful for their antagonistic action towards the αvβ3 and αvβ5 integrins.

More particularly, the invention concerns the use of compounds of general formulae (IV) and (V) for the preparation of drugs useful for the treatment of both altered angiogenic phenomena, and for those that may be encountered in metastasising tumour processes, retinopathies, acute renal damage and osteoporosis.

In one preferred embodiment of the invention, the anchoring system (T) binds with at least two targeting units of the invention and with at lest one biologically active molecule or moiety $R_6$, optionally through divalent linking moieties.

Therefore, it is a further object of the invention a compound of formula (VI)

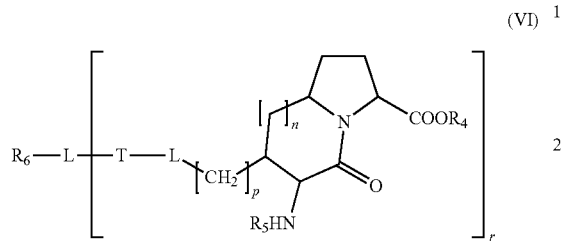

(VI)

wherein $R_4$, $R_5$, n, p, T and L, equal or different among them, have the meanings formerly reported for the compound of formula (IV);

r is an integer from 2 and 10, and $R_6$ is a biologically active moiety, their salts, racemic mixtures, individual enantiomers, individual diastereoisomers and mixtures thereof in whatever proportion.

In a different aspect, the anchoring system (T) of the invention may bind, optionally through linking moieties, to two or more biologically active molecules according to the invention thus providing a multimeric construct showing improved biological activity.

Thus, in a still further embodiment the invention relates to novel compounds of formula (VII)

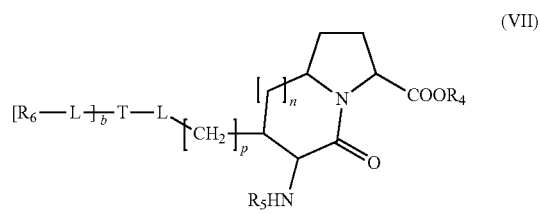

(VII)

in which:

$R_4$, $R_5$, n, p, T and L, equal or different among them, have the meanings formerly defined for compounds of (IV), b is an integer from 2 to 5, and $R_6$ is a biologically active moiety, their salts, racemic mixtures, individual enantiomers, individual diastereoisomers and mixtures thereof in whatever proportion.

Moreover, the multimeric targeting derivatives of formula (V) still have at least one free, optionally protected, binding site able to further bind, a biotin residue or a suitably biotinylated biologically active molecule.

It is therefore a further object of the invention a macromolecular aggregate such as, for example, a vescicle, a microsphere, a micelle or a liposome moiety, each of which comprising a high number of biotin residues on their surface, the said biotin residues being coupled, or anyway connected, with the above multimeric targeting constructs of formula (V).

Alternatively, these macromolecular aggregate may be obtained by coupling the said biotinylated vescicles, microspheres, micelles or a liposomes with a compound of formula (III) wherein $R_6$ is biotin moiety suitably coupled to an avidin moiety.

These aggregates may be prepared according to conventional methods known in the art, for instance as per the experimental section.

As an example, the said macromolecular aggregates can be represented by formula (VIII)

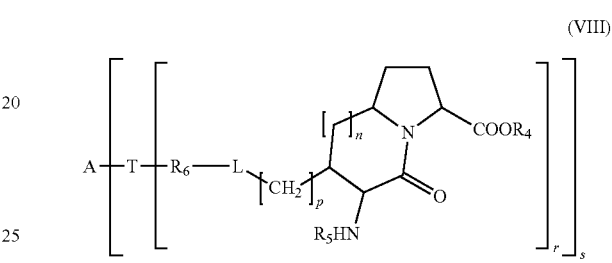

(VIII)

wherein:

$R_4$, $R_5$, n, p and L have the meanings above reported, $R_6$ is a biotin moiety, T is a streptavidin or an avidin moiety, r is 2 or 3, A is a vesicle, a microsphere, a micelle or a liposome moiety comprising a number of biotin units on their surface, s represents the number of the compounds of formula (V) per macromolecular aggregate.

Preferably the said s value is expressed as percent the said biotinylated peptidic derivative represents, being 100 the global components amount, including, surfactants, sphingolipids, oligolipids, phospholipids, proteins, polypeptides, carbohydrates, and synthetic or natural polymeric materials amounts.

Preferably, within the compounds of formula (VIII), r is 3.

Preferably, within the compounds of formula (VIII), s is up to 10%, more preferably up to 3 and most preferably s is 1%.

Suitable examples of compounds of formula (VIII) comprise macromolecular aggregates wherein A is represented by a paramagnetic liposome, a LIPOCEST or an echogenic gas filled vesicular compound.

In one embodiment, A in formula (VIII) comprises a biotinylated vesicular compound filled with an echogenic gas.

In another embodiment A in formula (VIII) is a biotinylated paramagnetic or superparamagnetic particle.

In a particularly preferred embodiment, A in formula (VIII) comprises a biotinylated LIPOCEST.

With LIPOCEST, as used herein, we intend a paramagnetic liposomes that act as CEST agents (LIPOCEST agents) for use in CEST imaging protocols.

With CEST imaging as used herein, we relates to the generation of contrast in an MRI imaging through irradiation of mobile protons in a CEST contrast agent containing at least one mobile proton in exchange with water or in a suitable CEST imaging system. In the present invention the CEST imaging system is represented by a liposomal system. In this case the chemical shift of the intraliposomal water protons which must be irradiated to observe saturation transfer has been suitably "shifted" as a result of their interaction with a paramagnetic chelate containing a metal selected from iron (II) (high-spin configuration), iron (III), cobalt (II), rhodium (II), copper (II), nickel (II), cerium (III), praseodymium (III), neodymium (III), gadolinium(III), dysprosium (III), erbium (III), terbium (III), holmium (III), thulium (III), ytterbium (III) and europium (III).

The paramagnetic complex can be encapsulated in the aqueous cavity of the liposome (if hydrophilic), and/or incorporated in the lipidic bilayer of the membrane (if amphiphilic).

The chemical shift difference between the resonances of intraliposomal and bulk water protons ($\Delta^{LIPO}$) is dependent on the formulation and preparation of the liposomes as well as the physico-chemical properties of the paramagnetic complex. In particular, the chemical shift of the water proton is affected by: i) the concentration of the hydrophilic paramagnetic complex in the aqueous cavity (if encapsulated) and/or the concentration of the paramagnetic complex incorporated in the membrane and facing the aqueous inner cavity of the liposome, and ii) the liposome shape. Macromolecular aggregates comprising a biotinylated LIPOCEST, their preparation and characterization are best detailed in the experimental section below.

Those skilled in the art may understand that macromolecular aggregates according to the invention comprising a number of peptidomimetic moieties on their surface may equally be obtained by connecting a macromolecular compound such as, for example, a vesicle, a microsphere, a micelle or a liposome including an high number of streptavidin or avidin moieties on their surface with a suitable number of biotinylated targeting derivatives of the invention, i.e., for example, compounds of formula (III) wherein $R_6$ is or comprises a biotin residue.

All the compounds of each of the formulae from (III) to (VIII) moreover possess interesting pharmacological properties, particularly an antagonistic effect towards the $\alpha v \beta 33$ and $\alpha v \beta 5$ integrins, and display interesting antiangiogenic activities.

Thus, according to another aspect thereof, the invention concerns pharmaceutical compositions containing, as active ingredient, at least one compound of each of the formulae from (III) to (VIII), the pharmaceutically acceptable salts, racemic mixtures, individual enantiomers, individual diastereoisomers and mixtures thereof in whatever proportion, in combination with one or more possible pharmaceutically acceptable carriers or excipients.

In a further aspect, the invention concerns a contrast agent according to anyone of formulae (III), (V), or (VIII) wherein $R_6$ is an imaging detectable moiety or in the form of imaging detectable macromolecular aggregate comprising on their surface a number of targeting moieties according to the invention.

In one embodiment the said contrast agent is an MRI contrast agent, and, preferably, is a paramagnetic liposomes that act as CEST agents.

Preparations

The novel compounds of the invention may be prepared by starting, at first, from the compounds of formula (I) below

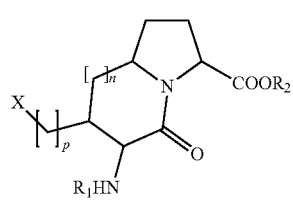

(I)

where:
n is 1 or 2,
p is an integer between 1 and 5, $R_1$ is H, ($C_1$-$C_4$) alkyl or a protective group,
$R_2$ is H or a protective group,
X is —$N_3$, —$NHR_3$, —$SR_3$, —N=C=O, or —N=C=S,
wherein $R_3$=H or a protective group;
their salts, racemic mixtures, individual enantiomers, individual diasteroisomers and mixtures thereof in any portion.

The compounds of formula (I) may exist in different configurations

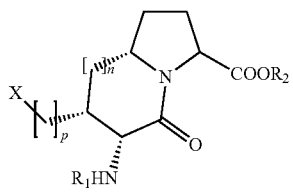

(Ia)

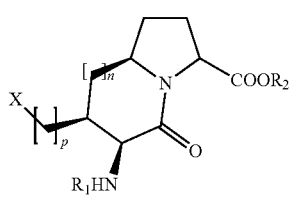

(Ib)

where n, $R_1$, $R_2$ and X are as defined above and the wedge-shaped and dashed bonds indicate that the substituents are positioned above and below the plane respectively. Unless otherwise provided, the term "($C_1$-$C_4$) alkyl" designates a linear or branched, saturated or unsaturated alkyl substituent comprising from 1 to 4 carbon atoms such as for example methyl, ethyl, propyl, isopropyl, butyl, tert-butyl. However, it is possible to use alkyl substituents containing a higher number of carbon atoms providing they are compatible with the reaction conditions of the present invention. According to the present invention, the expression "protective group" designates a protective group adapted to preserving the function to which it is bound, specifically the amino function or carboxyl function. Appropriate protective groups include for example benzyl, benzyloxycarbonyl, alkyl or benzyl esters, or other substituents commonly used for the protection of such functions, which are well known to those skilled in the art, for example those described in conventional manuals such as T. W. Green, *Protective Groups in Organic Synthesis* (Wiley, NY 1981).

The salts of the compounds of formulae (I), (Ia) and (Ib), according to the present invention, comprise both those with mineral or organic acids and those forming physiologically and pharmaceutically acceptable salts, such as for example hydrochloride, hydrobromide, sulphate, hydrogen sulphate, dihydrogen sulphate, maleate, fumarate, 2-naphthalene-sulphonate, para-toluenesulphonate, oxalate etc.

Salts of the compounds of formulae (I), (Ia) and (Ib) according to the present invention also further include physiologically and pharmaceutically acceptable quaternary ammonium salts.

Said salts are prepared according to the well known techniques for the person skilled in the art.

When there is a free carboxyl group ($R_2$=H) present, the salts of the compounds of formula (I) also comprise salts with organic or mineral bases, such as for example alkaline metal or alkaline earth metal salts, such as sodium salts, potassium or calcium salts, or with an amine such as trometamol (tromethamine), or salts of arginine, lysine or any other physiologically and pharmaceutically acceptable amine.

A process for the synthesis of the compounds of formula (I) is described in detail over the course of the present description, making reference to the synthetic schemes reported in the enclosed FIGS. 1-6.

According to the present invention, compounds of formulae (I), (Ia) and (Ib) may be prepared according to the processes described hereinafter.

Particularly, compounds of general formulae (Ia) 6,5-trans- and (Ib) 6,5-cis-fused, wherein p is 1, and n is 1 may be prepared according to a synthetic process outlined in Scheme 1, comprising the following stages:
a) hydrogenation of the isoxazolidine of compound 1 or of compound 2, for example with $H_2$, Pd/C in MeOH;
b) protection of the amine group with a suitable protective group, such as for example Cbz, Boc, etc.;
c) transformation of the free hydroxyl group into an azide through the Mitsunobu reaction, or by means of any other known method (for example, transformation into mesylate and subsequent nucleophilic substitution with sodium azide), to give compounds of formulae 6, 9;
d) reduction of the azide group into an amino group through the Staudinger reaction, or by means of hydrogenation to give compounds 7 and 10.

The compounds of general formulae (Ia) 7,5-trans and (Ib) 7,5-cis fused, wherein p is 1 and n is 2 may be prepared according to a synthetic process outlined in Scheme 2, comprising the following stages:
a) hydrogenation of the isoxazolidine of compound 3 or of compound 4, for example with $H_2$, Pd/C in MeOH;
b) protection of the amine group with a suitable protective group, such as for example Cbz, Boc, etc.;
c) transformation of the hydroxyl group into an azide through the Mitsunobu reaction, or by means of any other known method (transformation into mesylate and subsequent nucleophilic substitution with sodium azide), to give compounds of formulae 12, 15;
d) reduction of the azide group into an amino group through the Staudinger reaction, or by means of hydrogenation to give compounds 13, 16.

Corresponding compounds wherein X is —N=C=O or —N=S=O may be obtained from the above amino compounds 13 and 16 according to known procedures, i.e., for example, by reaction of the said compounds with phosgene or thiophosgene, respectively.

Compounds wherein X is —SH may be obtained for example by transformation of the hydroxyl group, through the Mitsunobu reaction, with thiolacetic acid (Tetrahedron Lett. 1981, 22, 3119), or by means of any other known methods.

Compounds of formula (I) wherein p is from 2 to 5 can be obtained according to known procedures, preferably starting from the above hydroxyl groups. For example, the compound of formula (I) where p is 2 can be obtained from the corresponding compound where p is 1 and X is OH by mesylation, reaction with NaCN and reduction of the nitrile. In another example, compound of formula (I) where p is 3 can be obtained from the corresponding compound where p is 1 and X is OH by oxidation to aldehyde, Wittig reaction with diethyl cyanomethylphosphonate and hydrogenation.

Figure 1:
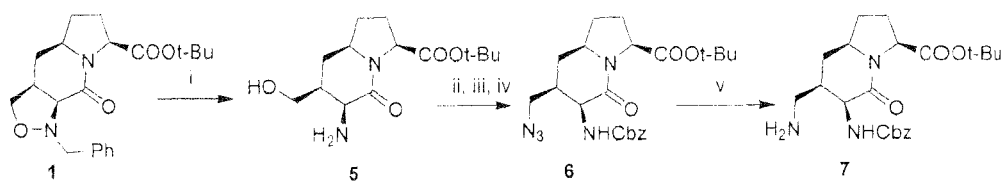
FIGS. 1-6 comprise synthetic schemes detailing the preparation of the peptidomimetic compounds of the invention. In particular.
Figure 1:
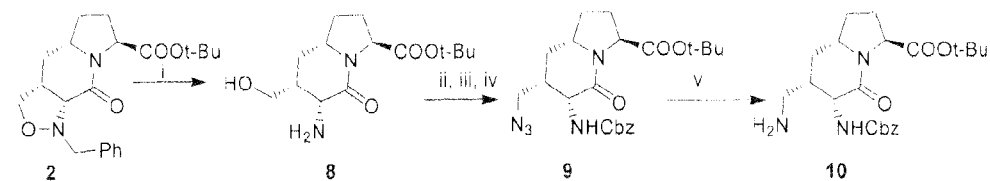
Figure 2:
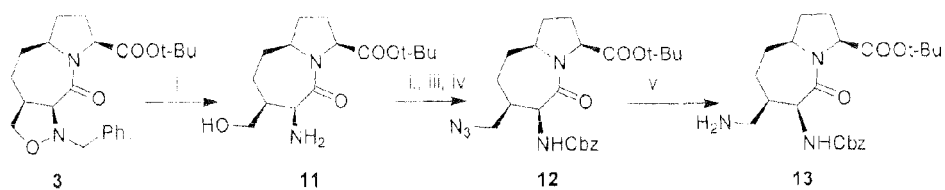
Figure 2:
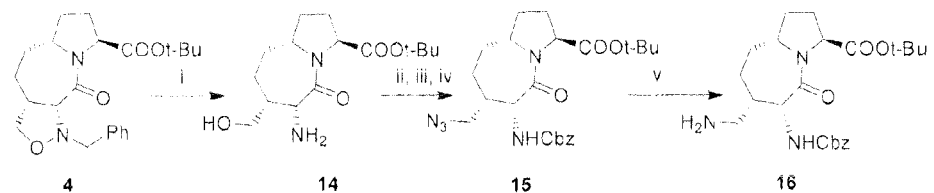
Figure 3:
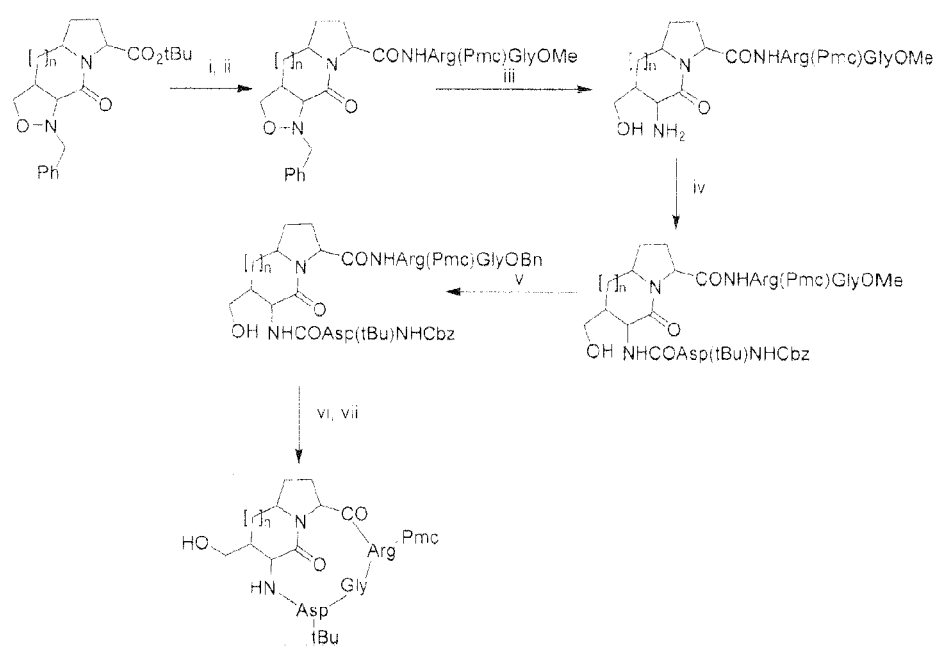

The tricyclic starting compounds 1-4 of FIGS. 1 and 2 may be prepared according to the procedures described in FIG. 6—Scheme A—Preparation of the starting products.

Then, the substitution of the $R_1$ and $R_2$ groups in formula (I) with the Arg-Gly-Asp (RGD) chain provides compounds which are able are able to selectively bind to integrin receptors and to act as selective inhibitor for αvβ3 and αvβ5 integrins, of general formula (II)

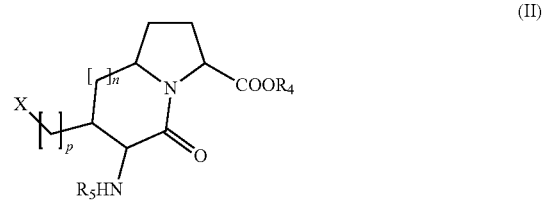

wherein:
n is 1 or 2,
p is an integer between 1 and 5,
$R_4$ and $R_5$ together constitute the sequence Asp-Gly-Arg,
X is —$N_3$, —$NHR_3$, —$SR_3$, —N=C=O, or —N=C=S,
where:
$R_3$=H or a protective group;
their salts, racemic mixtures, individual enantiomers, individual diastereoisomers and mixtures thereof in whatever proportion.

As before, the following configurations may be highlighted for the compounds of formula (II)

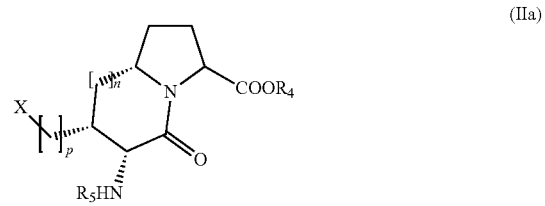

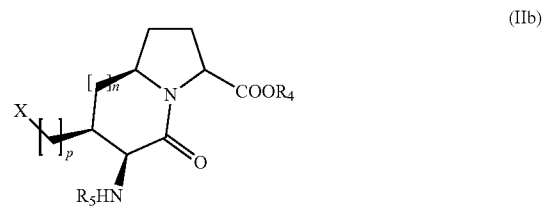

wherein n, $R_4$, $R_5$ and X are as defined above and the wedge-shaped and dashed bonds indicate that the substituents are positioned above and below the plane respectively.

The peptide sequence Asp-Gly-Arg is advantageously bound to compounds (II), (IIa) and (IIIb) in such a manner whereby the carboxyl group is attached to the amino acid arginine, and the amino group is attached to aspartic acid.

The details provided above for the variable substituents and the salts of the compounds of formula (I) are also applicable to the compounds of formulae (II), (IIa) and (IIb).

The Asp-Gly-Arg chain may be introduced by adapting the compounds of formulae (I), (Ia) and (Ib) described above, according to a process comprising the following stages (Scheme 3):
when $R_2$ is a protective group, chemoselective deprotection reaction of the carboxyl group of compound of general formula (I) and condensation with the appropriately protected Arg-Gly dipeptide;
reduction of the oxazolidine by means of catalytic hydrogenation;
transformation of the methyl ester of glycine into the benzyl ester through a transesterification reaction, followed by the simultaneous removal of the protective group from the glycine and the amino group from the aspartic acid by catalytic hydrogenation;

condensation agent mediated intramolecular cyclisation and subsequent deprotection of the amino acid side chain protective groups.

The functional group protection and deprotection reactions may be carried out in accordance with known techniques.

Compounds (IIa) and (IIb) may hence be obtained, according to a process comprising the following stages (schemes 4-5):

transformation of the hydroxyl group of compounds 17, 18, 19, 20 into the corresponding azides according to known procedures, for example through the Mitsunobu reaction, or mesylation and subsequent nucleophilic substitution with sodium azide, to give compounds 21, 23, 2, 27;

subsequent reduction by means of catalytic hydrogenation or Staudinger reaction thus providing corresponding amino derivatives;

optional transformation of the amino groups into corresponding cyanates or thiocyanates by use of phosgene or thiophosgene, respectively, using known reactions;

optional conjugation with molecules of biological interest by means of known reactions, subsequent deprotection of the aminoacid side chain protective groups to give the compounds of formulae 22, 24, 23 and 25.

In particular, the preparation of compounds 6,5- and 7,5-cis is reported in scheme 4 and the preparation of compounds 6,5- and 7,5-trans is reported in scheme 5.

Examples and details of such reactions are provided in the experimental section of the present description.

The functional group protection and deprotection reactions may be carried out in accordance with known techniques, such as those described in the experimental section of the present description.

Details of this kind of preparation for different, even if structurally analogous compounds, are provided in WO2005/042531.

The compounds of formula (II), (IIa) and (IIb) thus prepared and bearing any proper X group, as above defined, are further reacted so as to get the compounds of the invention.

As an example, the compounds of formula (II) wherein X is an optionally protected amino group may be reacted with moieties bearing a terminal carboxy group or a derivative thereof, so as to give rise to a carboxamido linkage.

This reaction, accomplished according to well known operative conditions, can be schematically represented as follows, for instance for the preparation of a compound of formula (III) wherein L is a group —CONH—:

R—COOH+H$_2$N—(CH$_2$)p-targeting unit---→
R$_6$—CONH—(CH$_2$)p-targeting unit

Likewise, for instance in the case X is a group —NCO or —NCS, the compounds of formula (III) wherein L is a group —NHCONH— or —NHCSNH— may be obtained as follows:

R$_6$—NH$_2$+OCN—(CH$_2$)p-targeting unit---→
R$_6$—NHCONH—(CH$_2$)p-targeting unit or R$_6$—NH$_2$+SCN—(CH$_2$)p-targeting unit---→
R$_6$—NHCSNH—(CH$_2$)p-targeting unit.

The compounds wherein L is a group (iv) may be obtained by reacting the corresponding derivative of formula (II) wherein X is azido (—N$_3$) with the corresponding moiety properly functionalised through a terminal alkino group —C≡CH, according to well known operative conditions, such as, for example, the so called "click chemistry" 1,3-dipolar cycloaddition reaction, (see, Kolb, H et al, Angew. Chem. Int. Ed. 2001, 40, 2004-20021).

See, as an example:

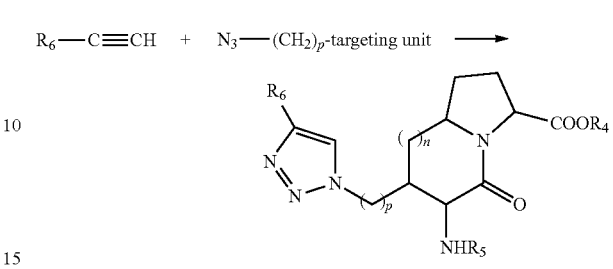

The compounds wherein L is a group (v) may be obtained by reacting the corresponding derivative of formula (II) wherein X is SH with the corresponding moiety properly functionalised with a maleimide, according to well known operative conditions (see Brinkley, M. Bioconjugate Chem. 1992, 3, 2-13).

See, as an example:

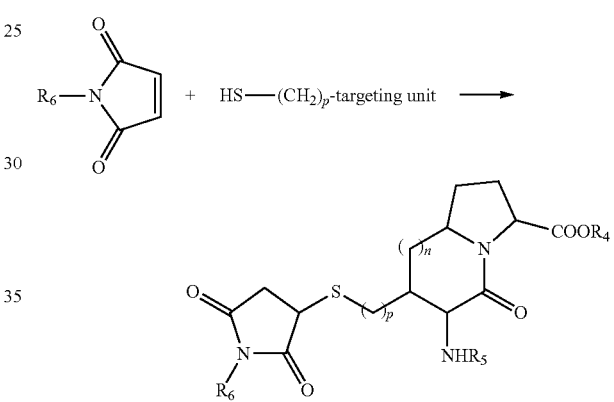

Clearly, the above schemes may apply as well for the preparation of the compounds of formula (III) of the invention wherein L is a divalent linking moiety comprising any one of the aforementioned (i) to (v) groups.

In such a case, the following order of reactions may apply, for instance in the preparation of a compound of formula (III), wherein L is the following group:

—NHOC—CH$_2$—O—(CH$_2$)$_2$—O—(CH$_2$)$_2$—O—CH$_2$—CONH—

R$_6$—NH$_2$+HOOC—CH$_2$—O—(CH$_2$)$_2$—O—(CH$_2$)$_2$—O—CH$_2$—COOH---→
---→R$_6$—HNOC—CH$_2$—O—(CH$_2$)$_2$—O—(CH$_2$)$_2$—O—CH$_2$—COOH and, then
R$_6$—HNOC—CH$_2$—O—(CH$_2$)$_2$—O—(CH$_2$)$_2$—O—CH$_2$—COOH+H$_2$N—(CH$_2$)p-targeting unit
---→R$_6$—HNOC—CH$_2$—O—(CH$_2$)$_2$—O—(CH$_2$)$_2$—O—CH$_2$—CONH—(CH$_2$)p-targeting unit.

From the above it is clear to the skilled person that, whenever convenient, the order of the reactions may be properly varied, substantially as follows:

HOOC—CH$_2$—O—(CH$_2$)$_2$—O—(CH$_2$)$_2$—O—CH$_2$—COOH+H$_2$N—(CH$_2$)p-targeting unit→
→HOOC—CH$_2$—O—(CH$_2$)$_2$—O—(CH$_2$)$_2$—O—CH$_2$—CONH—(CH$_2$)p-targeting unit and, then +R$_6$—NH$_2$ so as to get the compound of formula (III).

Any of the said cross-linking or coupling reactions may be performed according to appropriate reactions well known to those skilled in the art.

Thus, for examples, the lactamic structures including an azido group may be bound the desired biologically active molecules or compounds of biological importance through appropriate reactions i.e., for example, Click chemistry.

When the lactamic structures includes an amine group, the biologically active moiety may be bound, for example, through a simple amidation reaction.

Moreover, the cyclic peptidomimetic wherein X=—NH—CO or —NH—CS may be bound to suitable amine group of the biologically active molecule according to procedures known to the person skilled in the art to give, for example, corresponding ureas or thioureas derivatives.

Examples and details concerning the former functional groups and cross-linking reaction between them are provided in the experimental section of the present description.

Preferably, in case L is other than a group (i) to (v) within the compounds of the invention, it may be conveniently derived from the following molecules (shortly referred to as linkers) listed in table I below

TABLE 1

| LINKER | |
|---|---|
| A1 | 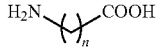 |
| | n = 1-6, 11 |
| A2 | 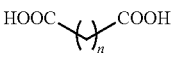 |
| | n = 1-4 |
| A3 | 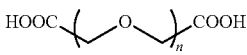 |
| | n = 1-3 |
| A4 |  |
| | n = 2-6 |
| A5 | 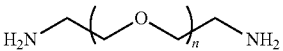 |
| | n = 1-5 *Tetrahedron Lett.* 1998, 39, 6277; *Makromol. Chem.* 1979, 180, 2539. |
| A6 | 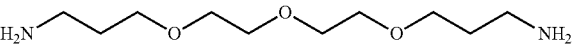 [SMILES: NCCCOCCOCCOCCCN] |
| A7 | 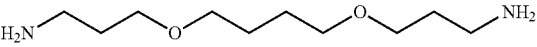 |
| A8 | 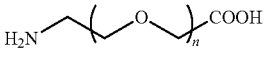 |
| | n = 1-4; *J. Org. Chem.* 2001, 66, 4799; *Org. Prep. Proceed. Int.* 2002, 34, 326 |
| A9 | 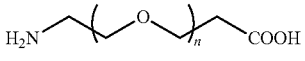 |
| | n = 1-6; *Bioconjugate. Chem.* 1999, 10, 1021. |
| A10 | 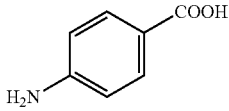 |
| A11 | 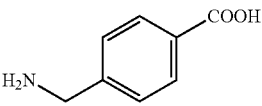 [SMILES: NCc1ccc(C(=O)O)cc1] |
| A12 | 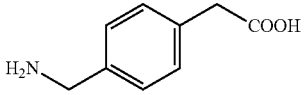 [SMILES: NCc1ccc(CC(=O)O)cc1] |

TABLE 1-continued
| LINKER | |
|---|---|
| A13 | 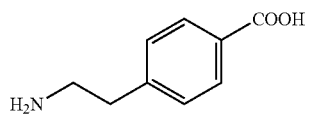 [SMILES: NCCc1ccc(C(=O)O)cc1] |
| A14 | 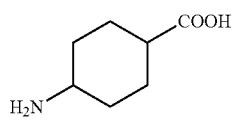 |
| A15 | 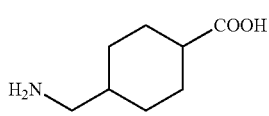 |
| A16 | 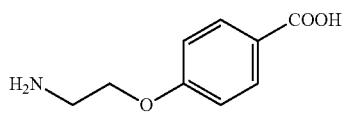 [SMILES: NCCOc1ccc(C(=O)O)cc1] |
| A17 | 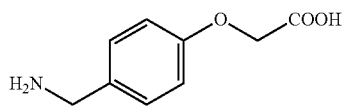 [SMILES: NCc1ccc(OCC(=O)O)cc1] |
| A18 | 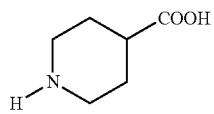 |
| A19 |  |
| A20 | 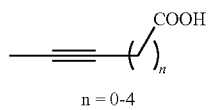<br>n = 0-4 |
| A21 | 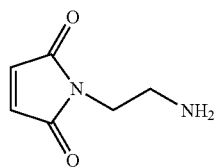<br>Bioconjugate Chem. 1990, 1, 431 |
| A22 | 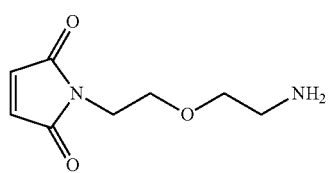<br>Bioconjugate Chem. 1990, 1, 431 |
| A23 | 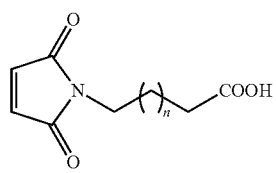<br>n = 0-3 |

TABLE 1-continued

| LINKER | |
|---|---|
| A24 | 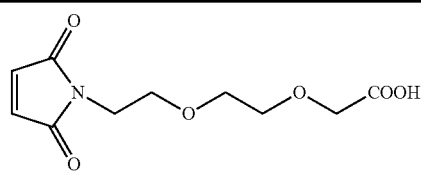<br>Bioconjugate Chem. 1996, 7, 180 |
| A25 | 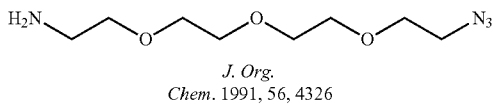 [SMILES: [N-]=[N+]=NCCOCCOCCOCCN]<br>J. Org. Chem. 1991, 56, 4326 |
| A26 | 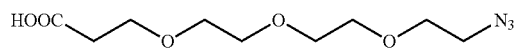<br>Bioconjugate Chem. 1999, 10, 1021. |
| A27 | 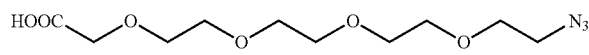<br>Bioconjugate Chem. 2000, 11, 14. |
| A28 | 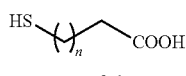<br>n = 0-1 |
| A29 | 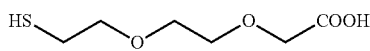<br>Bioconjugate Chem. 1996, 7, 180 |
| A30 | 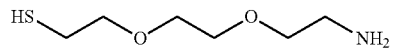<br>Tetrahedron 1997, 53, 10939 |
| A31 | 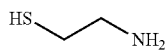 | or it may be even obtained from a suitable combination thereof thus providing modified and/or elongated compounds such as, for example,

A32

Most of the linkers of Table 1 are well known and commercially available from, for example, Aldrich Neosystem and Peptides International catalogs. The non-marketed compounds may be easily prepared according to known methods, for example as per the accompanying bibliographic references.

The compound A 32 is new and it constitutes a further object of the present invention.

As formerly explained, the above linkers or suitable combinations thereof may be connected to X, from one side, and to $R_6$, from the other side, by use of cross-linking or coupling reactions well known in the art. When X is an azide group, for example, one approach, may be based on the so called "click chemistry" 1,3-dipolar cycloaddition reaction, (see, f.e., Kolb, H et al, Angew. Chem. Int. Ed. 2001, 40, 2004-20021), between the said azide group and a terminal acetilenic group of the bifunctional moiety. This kind of approach is best detailed in the experimental section below. This same kind of reaction, obviously allows to connect an acetylenic group on the peptide side with a linker bearing a terminal azido group.

When X is SH—, a suitable reaction may occur with a bifunctional linker including, for example, a maleimido terminal group such as, for instance those listed as A22-A24 in Table 1.

When X is $NH_2$, the linker may suitably include a C terminus, i.e. a carboxylic terminal group. The connection between L and $R_6$ may be through a number of arrangements, including, e.g., (a) from C-terminus to C-terminus; (b) from N-terminus (i.e. a terminal amine group) to C-terminus; (c) from C-terminus to N-terminus; or (d) from N-terminus to N-terminus depending on the binding groups of L and $R_6$ involved in the cross-linking reaction.

The above coupling reactions may further apply when considering the preparation of all of the compounds of the invention deriving from coupling one or more peptidomimetic moieties of formula (II), an anchoring system selected from those of FIG. 7A-7C, one or more $R_6$ biologically active moieties of the invention, through one or more linking units.

Obviously, when operating all the above coupling reactions, the optional functional groups on the coupling molecules that are not involved in the said reactions must be protected to avoid undesired bonds being formed. The protecting groups that can be used are listed, for example, in Greene, *Protective groups in Organic Synthesis*, John Wiley & Sons, New York (1981).

Chelates

In the case of $R_6$, as per the compounds of the invention, is a diagnostic or radiotherapeutic agent, for instance a metal chelate or a system containing several or many metal chelates of any suitable metal ion among those formerly reported, complexation may occurs by properly labelling any compound of the invention wherein $R_6$ is or comprises a chelating unit or units with the proper metal of choice, according to well known methods.

For example, the paramagnetic complexes of the invention and, particularly, the Gd(III) chelates may be prepared by stoichiometric addition of suitable Gd(III) derivatives, particularly Gd(III) salts or oxides. See, for instance, EP 230893 disclosing labelling with paramagnetic metal ions, and WO 98/52618, U.S. Pat. No. 5,879,658, and U.S. Pat. No. 5,849,261 disclosing labelling with radioactive metals.

As an example, complexes of radioactive technetium or indium of the invention are particularly useful for diagnostic imaging whilst complexes of radioactive rhenium are particularly useful for radiotherapy.

When considering PET imaging, complexes of Ga-68 and Cu-64 as well as various Lanthanides are particularly useful.

In forming a complex of radioactive technetium, for instance, a technetium complex, preferably a salt of $^{99m}Tc$ pertechnetate, is reacted with the unlabelled compounds of the invention in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of compound of the invention to be labeled and a sufficient amount of reducing agent to label the reagent with $^{99m}Tc$. Alternatively, the complex may be formed by reacting a compounds of this invention, which is conjugated with an appropriate chelating moiety with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the $^{99m}Tc$ pertechnetate salts useful with the present invention are included the alkali metal salts such as the sodium salt, or ammonium salts or lower alkyl ammonium salts. Preparation of the complexes of the present invention where the metal is radioactive rhenium may be accomplished using as starting materials rhenium compounds wherein the metal is in the +5 or +7 oxidation state. Examples of compounds in which rhenium is in the Re(VII) state are $NH_4ReO_4$ or $KReO_4$. Re(V) is available as, for example, $[ReOCl_4](NBu_4)$, $[ReOC_4]$ $(AsPh_4)$, $ReOCl_3(PPh_3)_2$ and as $ReO_2(pyridine)_{4'}$ (Ph is phenyl; Bu is n-butyl). Other rhenium reagents capable of forming a rhenium complex may also be used.

Radioactively-labeled scintigraphic imaging agents provided by the present invention must contain a suitable amount of radioactivity. In forming $^{111}In$ or $^{99m}Tc$ complexes, it is generally preferred to form radioactive complexes in solutions containing radioactivity at concentrations of from about 0.01 millicurie (mCi) to 100 mCi per mL.

The compounds of the invention find a variety of applications in the therapeutic and diagnostic field.

MRI contrast agents according to the present invention, for instance, may be used in the same manner as conventional MRI contrast reagents. When the target is, for example, an angiogenic site in a tissue, certain MR techniques and pulse sequences may be preferred to enhance the contrast of the site to the background blood and tissues. These techniques include (but are not limited to), for example, black blood angiography sequences that seek to make blood dark, such as fast spin echo sequences (see, e.g., Alexander et al., *Magnetic Resonance in Medicine*, 40(2): 298-310 (1998)) and flow-spoiled gradient echo sequences (see, e.g., Edelman et al., *Radiology*, 177(1): 45-50 (1990)). These methods also include flow independent techniques that enhance the difference in contrast, such as inversion-recovery prepared or saturation-recovery prepared sequences that will increase the contrast between target containing tissue, such as an angiogenic tumor, and background tissues. Finally, magnetization transfer preparations may also improve contrast with these agents (see, e.g., Goodrich et al., *Investigative Radiology*, 31(6): 323-32 (1996)).

The paramagnetic contrast agents of the invention, for use in MRI techniques, are administered to the patient in the form of an injectable compositions. The method of administering the MRI contrast agent is preferably parenterally, meaning intravenously, intraarterially, intrathecally, interstitially, or intracavitarily. For imaging active angiogenesis, intravenous or intraarterial administration is preferred.

For MRI, it is contemplated that the subject will receive a dosage of contrast agent sufficient to enhance the MR signal at the target (e.g., a site of angiogenesis) at least 10%. After injection of the targeted contrast agent of the invention including the MRI agent, the patient is scanned in the MRI machine to determine the location of any sites containing the target. In therapeutic settings, upon target localization, a cytotoxic or therapeutic agent can be immediately administered, if necessary, and the patient can be subsequently scanned to visualize the therapeutic effect.

In case of radiotherapy, proper dose schedules known in the art may be used for the radiotherapeutic compounds of the present invention.

The compounds can be administered using many methods which include, but are not limited to, a single or multiple IV or IP injections, using a quantity of radioactivity that is sufficient to cause damage or ablation of the targeted tissue, but not so much that substantive damage is caused to non-target (normal tissue). The quantity and dose required is different for different constructs, depending on the energy and half-life of the isotope that is used, the degree of uptake and clearance of the agent from the body and the mass of the tumor. In general, doses can range from about 0.01 mCi to about 100 mCi, preferably from 1 mCi to 50 mCi. Typically, a single dose of about 30-50 mCi to a cumulative dose of up to about 3 Curies may apply.

The radiotherapeutic compositions of the invention can include physiologically acceptable buffers, and can require radiation stabilizers to prevent radiolytic damage to the compound prior to injection. Radiation stabilizers are known to those skilled in the art, and may include, for example, para-aminobenzoic acid, ascorbic acid, gentisic acid and the like.

In case of radionuclide imaging, the compound of the invention may be administered to the patient through injection. A PET camera or a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

A single, or multi-vial kit that contains all of the components needed to prepare the radiopharmaceuticals of this invention, other than the radionuclide, is an integral part of this invention.

A single-vial kit preferably contains a chelating ligand (if a metal radionuclide is used), a source of a stannous salt (if reduction is required, e.g., when using technetium), or other pharmaceutically acceptable reducing agent, and is appropriately buffered with pharmaceutically acceptable acid or base to adjust the pH to a value of about 3 to about 9. The quantity and type of reducing agent used would depend highly on the nature of the exchange complex to be formed. The proper conditions are well known to those that are skilled in the art. It is preferred that the kit contents be in lyophilized form. Such a single vial kit may optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or $\alpha$-, $\beta$-, or $\gamma$-cyciodextrin that serve to improve the radiochemical purity and stability of the final product. The kit may also contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial may contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. may be present in either or both vials.

As above reported, the compounds of the invention can be suitably formulated according to known methods and the compositions thereof do represent an additional object of the invention.

In order to obtain the desired prophylactic, therapeutic or diagnostic effect, a therapeutically or diagnostically effective dose or amount of the active ingredient is advantageously administered in the form of a unit dose, one or more times daily. The daily dosages are obviously selected by the health professional depending on the biologically active molecule introduced.

The term "effective dose or amount", as used herein, refers to any amount of a diagnostic or a therapeutic molecule of the invention, or pharmaceutical composition thereof, that is sufficient to fulfil its intended diagnostic or therapeutic purpose(s): i.e., for example, to visualize a patient biological element including cells, biological fluids and biological tissues as well as human body organs, regions or tissues affected by angiogenesis, or its intended therapeutic purpose(s); or to delay or to prevent to onset of a pathological condition associated with angiogenesis; or to slow down or stop the progression, aggravation, or deterioration of the symptoms.

The diagnostic or therapeutic agents of the invention have a wide range of applications as they can be used for oral, intravasal, (for instance intravenous, intraarterial, intracoronaric, intraventricular administration and the like), intrathecal, intraperitoneal, intralymphatic and intracavital administrations. Compositions for the desired route of administration can be prepared by any of the methods well known in the pharmaceutical arts. Details concerning dosages, dosage forms, modes of administration, composition and the like are further discussed in a standard pharmaceutical text, such as *Remington's Pharmaceutical Sciences,* 18th Ed., Alfonso R. Gennaro, ed. (Mack Publishing Co., Easton, Pa. 1990), which is hereby incorporated by reference.

In one preferred embodiment, a suitable pharmaceutical composition according to the invention is formulated in accordance with routine procedures as a pharmaceutical composition adapted for intravenous administration to human being. Typically, compositions for intravenous administration are solutions in sterile isotonic aqueous buffer. Other pharmaceutically acceptable carriers include, but are not limited to, sterile water, saline solution, buffered saline water, saline solution, buffered saline (including buffers like phosphate or acetate), alcohol, vegetable oils, polyethylene glycols, gelatin, lactose, amylose, magnesium stearate, talc, silicic acid, paraffin, etc. Where necessary, the composition may also include a solubilizing agent and a local anaesthetic such as, e.g., lidocaine to ease pain at the site of the injection; and further may include preservatives, stabilizers, wetting agents, emulsifiers, salts, lubricants, etc. as long as they do not react deleteriously with the active compounds. Similarly, the composition may comprise conventional excipients, i.e., pharmaceutically acceptable organic or inorganic carrier substances suitable for parenteral, enteral or intranasal application which do not deleteriously react with the active compounds. Generally, the ingredients will be supplied either separately or mixed together in unit dosage form, for example, as a dry lyophilized powder or water free concentrate in a hermetically sealed container such as, e.g., an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline may be provided so that the ingredients may be mixed prior to administration.

Such pharmaceutical compositions are preferably formulated for parenteral administration, and most preferably for intravenous or intra-arterial administration. Generally, and particularly when administration is intravenous or intra-arterial, pharmaceutical compositions may be given as a bolus, as two or more doses separated in time, or as a constant or non-linear flow infusion.

The diagnostic or therapeutic agents of the invention can be administered to an individual over a suitable time course, depending on the nature of the condition and the desired outcome. As described herein, the compounds of the present invention can further be administered systemically or locally including, for example, through topical application, transdermal, parenteral, gastrointestinal, intravaginal, and transalveolar administration.

For topical applications, the compounds of the invention can be suspended, for example, in a cream, gel or rinse which allows the peptidic derivatives or multimeric constructs to penetrate the skin and enter the blood stream, for systemic delivery, or contact the are of interest, for localized delivery. Compositions suitable for topical application include any pharmaceutically acceptable base in which the polypeptides are at least minimally soluble. For transdermal administration, the compounds of the invention can be applied in pharmaceutically acceptable suspension together with a suitable transdermal device or "patch." Examples of suitable transdermal devices for administration of the diagnostic or therapeutic agents of the present invention are described, for example, in U.S. Pat. No. 6,165,458, issued Dec. 26, 2000 to Foldvari, et al., and U.S. Pat. No. 6,274,166B1, issued Aug. 4, 2001 to Sintov, et al., the teachings of which are incorporated herein by reference.

For parenteral administration, the diagnostic or therapeutic agents of the invention can be suspended, for example, in a pharmaceutically acceptable sterile isotonic solution, such as saline and phosphate buffered saline. Then they may be injected intravenously, intramuscularly, intraperitoneally, or subcutaneously.

For the oral administration, the agents of the invention can be formulated according to preparation methods routinely used in the pharmaceutical technique or as coated formulations to gain additional protection against the stomach acidic pH, thus preventing the chelated metal ion from release, which takes place particularly at the typical pH values of gastric fluids.

Other excipients, for example including sweeteners and/or flavouring agents, can also be added, according to known techniques of pharmaceutical formulations.

For gastrointestinal and intravaginal administration, the compounds of the invention can be incorporated into pharmaceutically acceptable powders, pills or liquids for ingestion, and suppositories for rectal or vaginal administration.

For transalveolar, buccal or pulmonary administration, the diagnostic or therapeutic agents pf the invention can be suspended in a pharmaceutically acceptable excipient suitable for aerosolization and inhalation or as a mouthwash. Devices suitable for transalveolar administration such as atomizers and vaporizes are also included within the scope of the invention. Suitable formulations for aerosol delivery of polypeptides using buccal or pulmonary routes can be found, for example in U.S. Pat. No. 6,312,665B1, issued Nov. 6, 2001 to Pankaj Modi, the teachings of which are incorporated herein by reference.

In addition, the agents of the invention can be administered nasally or ocularly, where the diagnostic or therapeutic compounds of the invention are suspended in a liquid pharmaceutically acceptable agent suitable for dropwise dosing.

In an even further aspect the invention relates to the use of the said novel diagnostic agents for the preparation of a diagnostic formulation for use in the diagnostic imaging, both in vitro and in vivo, of pathological systems, including cells, biological fluids and biological tissues originating from a live mammal patient, and preferably, human patient, as well as of human body organ, regions or tissues affected by angiogenic processes, including tumorous or cancerous tissues, inflammations, over-expressing integrin and particularly αvβ3 integrin receptors, as well as for monitoring the progress and results of therapeutic treatment of the said pathologies. In yet another aspect the invention provides a method for imaging angiogenesis both in vitro and in vivo comprising the use of a diagnostic imaging agent of the invention targeted to integrin receptors and an imaging technique.

In a preferred aspect the invention provides a method of in vivo imaging of a patient comprising: administering, by injection or infusion, to a patient an imaging effective amount of a diagnostic agent of formulae (III), (VI), (VII) and (VIII) wherein the peptidic moiety of the said diagnostic compound allows the imaging agent to interact with integrins so consenting thereof detection by use of an imaging technique.

In a further aspect, the invention concerns a therapeutic agent according to anyone of formulae (III), (VI) or (VII) wherein $R_6$ is a therapeutically effective moiety and, preferably, a radiotherapeutical agent, or in the form of therapeutically effective macromolecular aggregate comprising on their surface a number of targeting moieties according to the invention.

In still further aspect the invention provides a method of preventing or inhibiting angiogenesis both in vitro and in vivo comprising contacting a pathological systems, including cells, biological fluids, biological tissues, originating from a live mammal patient, and preferably, human patient, or a body organ, tissue or area exhibiting angiogenic vasculature with a therapeutic agent of the invention.

EXPERIMENTAL SECTION

Terms and Abbreviations Definition

CEST Contrast Enhanced Saturation Transfer
ATCC: American Type Culture Cell
MEM: Minimum Essential Medium
O.G.: Official Gazette
PBS: Dulbecco's Phosphate Buffered Saline without Ca++ and Mg++
RT: Room Temperature
EBM: Endothelial Cell Basal Medium
EGM: Endothelial Growth Medium
HUVEC: Human Umbilical Vein Endothelial Cell
DMEM: Dulbecco's Modified Eagle's Medium
FCS: Foetal Calf Serum
RGD: Arg-Gly-Asp
Fmoc or fmoc 9-fluorenylmethyloxycarbonyl
NHS N-hydroxysuccinimide
DMF dimethylformamide
DMAP 4-dimethylaminopyridine
TEA Triethylamine
MeCN acetonitrile
MsCl methanesulfonylchloride
DCM dichloromethane
DMSO dimethyl sulfoxide
TFA trifluoroacetic acid
Cbz Carbobenzyloxy
Boc t-butyloxycarbonyl
Ser Serine
Pro Proline
Gly Glycine
Arg Arginine
POPC 1-Palmitoyl-2-Oleoyl-sn-Glycero-3-Phosphocholine.
DSPE-PEG2000Biotin 1,2-Distearoyl-sn-Glycero-3-Phosphoethanolamine-N-[Biotinyl(Polyethylene Glycol)2000] (Ammonium Salt)
DPDP 1,2-Dipalmitoyl-sn-Glycero-3-Phosphocholine
DPPC 1,2-Dipalmitoyl-sn-Glycero-3-Phosphocholine
DIPEA Diisopropylethylamine
HBTU (2-(1H-Benzotriazol-1-yl)-1,2,3,3-tetramethyluronium hexafluorophosphate)
ST Saturation Transfer Preparation and tests concerning novel cyclic pentapeptide derivatives of the invention are illustrated in the following examples. The specific parameters included in the following examples are intended to illustrate the practice of the invention, and they are not presented to in any way limit the scope of the invention. A skilled technician may understand that different preparation approaches may equally be adopted based on synthetic procedures well known in the art.

General Observations:

The reported $^1$H-NMR and $^{13}$C-NMR data for prepared compounds have been recorded in the solvents indicated using a Brüker Avance-400 instrument at 400 MHz and 100.6 MHz respectively. Chemical shift values are indicated in ppm and the coupling constants in Hz. Optical rotatory powers are measured using a Perkin-Elmer model 241 polarimeter. Thin layer chromatography (TLC) is performed using Merck F-254 plates. Flash chromatography is performed using Macherey-Nagel 60, 230-400 mesh silica gel. Solvents are anhydrified in accordance with standard procedures and reactions requiring anhydrous conditions are carried out in an argon atmosphere. FAB+ mass spectrometry has been performed using a VG 7070 EQ-HF spectrophotometer, ESI+ mass spectrometry has been performed using a Bruker Esquire 3000 plus spectrophotometer.

LIPOCEST agents have been characterised by 1H-NMR using a Bruker Avance 600 spectrometer. Details on each of the adopted conditions are cited in the examples below.

The MR-CEST images have been acquired on a Bruker Avance 300 spectrometer equipped with a microimaging probe.

Preparation of the Cyclic Pentapeptides
Functionalization of the Compounds Deriving 1,3 dipolar Cyclization (Scheme 1 and Scheme 2).

a) Protection of the Free Amino Group

To a solution of product 5 or 14 (0.51 mmol) in anhydrous $CH_2Cl_2$ (5 ml) under argon atmosphere and at room temp., are added in the following sequence TEA (184 µl, 1.33 mmol), Cbz-Cl (95 µl, 0.61 mmol) and finally DMAP (15 mg, 0.126 mmol). The solution is kept under stirring for approx. 18 hours. After this period of time, it is taken up with $CH_2Cl_2$ (5 ml) and washed with $NH_4Cl$ (2×5 ml). The organic phase, dried over $Na_2SO_4$, is taken to evaporated and the crude product thus obtained is purified by flash chromatography (EtOAc/ETP 7:3→8:2) to give the desired product as a white foam (60%-78%).

Characterization of Compound 5-Cbz

Yield: 78%. $[\alpha]_D^{22}$=−13.7 (c=1.0, $CHCl_3$). 1H-NMR (400 MHz, $CDCl_3$): δ 1.48 (s, 9H, $C(CH_3)_3$), 1.6 (m, 1H, H-5), 1.7 (m, 1H, H-7), 2.06 (m, 1H, H-8), 2.2 (m, 1H, H-8), 2.23 (m, 1H, H-7), 2.3 (m, 1H, H-5), 2.75 (m, 1H, Ht-4), 2.92 (bs, 1H, OH), 3.6 (dd, 1H, HCHOH), 3.71 (m, 1H, HCHOH), 3.72 (m, 1H, H-6), 4.38 (t, 1H, H-3), 4.48 (d, 1H, H-9), 5.15 (dd, 2H, $CH_2Ph$), 6.0 (d, 1H, NHCbz), 7.28-7.42 (m, 5H, aromatic protons). 13C NMR (100.6 MHz, $CDCl_3$): δ 171.7, 168.1, 156.7, 136.4, 128.5, 128.8, 127.9, 82.4, 66.9, 63.5, 58.9, 55.7, 52.1, 37.9, 32.5, 32.0, 31.6, 29.7, 29.2, 27.9. MS [FAB+]: 419.3 [M+1]+. Calculated elemental analysis $C_{22}H_{30}N_2O_6$: C, 63.14; H, 7.23; N, 6.69; observed C, 62.16; H, 7.25; N, 6.67.

Characterization of Compound 14-Cbz

Yield: 60%. $[\alpha]_D^{22}$=−25.5 (c=1.0, $CHCl_3$). 1H-NMR (400 MHz, $CDCl_3$): δ 1.48 (s, 9H, $C(CH_3)_3$), 1.51 (m, 1H, H-6), 1.53 (m, 1H, H-4), 1.75 (m, 1H, H-5), 1.83 (m, 1H, H-6), 1.98 (m, 1H, H-9), 2.0 (m, 1H, H-5), 2.2 (m, 1-t, H-9), 2.25 (m, 1H, H-8), 2.33 (m, 1H, H-8), 3.4 (t, 1H, HCHOH), 3.72 (d, 1H, OH), 3.82 (d, 1H, HCHOH), 4.03 (t, 1H, H-7), 4.42 (dd, 1H, H-3), 4.5 (d, 1H, H-10), 5.15 (dd, 2H, $CH_2Ph$), 6.48 (d, 1H, NHCbz), 7.31-7.43 (m, 5H, aromatic protons). 13C NMR (100.6 MHz, $CDCl_3$): δ 170.5, 170.3, 158.0, 136.0, 128.6, 128.2, 128.1, 81.6, 67.5, 64.5, 61.0, 58.7, 55.5, 42.5, 33.9, 32.1, 30.9, 29.7, 29.3, 28.0, 27.2. MS [ESI+]: 433.3 [M+H]+, 455.3 [M+Na]+, Calculated elemental analysis $C_{23}H_{32}N_2O_6$: C, 63.87; H, 7.46; N, 6.48; observed C, 63.85; H, 7.47; N, 6.47.

b) Synthesis of Azide-Derivatives

To a solution of product 5-Cbz or 14-Cbz (0.29 mmol) in anhydrous $CH_2Cl$ (4 ml) under argon atmosphere and at room temp., are added in the following sequence MsCl (846 µl, 0.59 mmol) and TEA (165 ti, 1.18 mmol). The solution is kept under stirring for approx. 45 minutes. After this period of time, it is taken up with $CH_2Cl$ and washed with $NH_4Cl$. The organic phase, dried over $Na_2SO_4$ is evaporated and the crude product thus obtained dissolved in DMF (3.2 ml) and, under argon atmosphere and at room temp., $NaN_3$ (154 mg, 2.37 mmol) is added. The reaction is kept under stirring at 80° C. for approx. 18 hours. After this period of time, the DMF is evaporated off to dryness, and the crude product dissolved in $CH_2Cl_2$ and washed with $H_2O$. The organic phase, dried over $Na_2SO_4$, is taken to dryness and the crude product thus obtained is purified by flash chromatography (AcOEt/ETP 7:3) to give the desired product as a white foam (76%-90%).

Characterization of Compound 6

Yield: 76%. $[\alpha]_D^{22}$=+19.0 (c=1.0, $CHCl_3$). 1H-NMR (400 MHz, $CDCl_3$): δ 1.48 (s, 9H, $C(CH_3)_3$), 1.61 (m, 1H, H-5), 1.72 (m, 1H, H-7), 2.08 (m, 1H, H-8), 2.14 (m, 1H, H-8), 2.24 (m, 1H, H-7), 2.31 (m, 1H, H-5), 2.9 (m, 1H, H-4), 3.28 (dd, 1H, J=Hz, $HCHN_3$), 3.48 (dd, 1H, $HCHN_3$), 3.7 (m, 1H, H-6), 4.31 (t, 1H, H-3), 4.39 (d, 1H, H-9), 5.15 (s, 2H, $CH_2Ph$), 6.0 (bs, 1H, NHCbz), 7.28-7.42 (m, 5H, aromatic protons). 13C NMR (100.6 MHz, $CDCl_3$): δ 170.4, 166.7, 156.1, 136.3, 128.5, 128.1, 127.9, 81.9, 67.0, 59.0, 55.3, 55.8, 52.6, 35.4, 32.3, 31.8, 29.2, 28.0. MS [ESI+]: 444.3 [M+H]+. Calculated elemental analysis $C_{22}H_{29}N_5O_5$: C, 59.58; H, 6.59; N, 15.79; observed C, 59.57; H, 6.58; N, 15.81.

Characterization of Compound 15

Yield: 90%. $[\alpha]_D^{22}$=−13.8 (c=1.0, $CHCl_3$). 1H-NMR (400 MHz, $CDCl_3$): δ 1.48 (s, 9H, $C(CH_3)_3$), 1.5 (m, 1H, H-5), 1.68 (m, 1H, H-4), 1.70 (m, 1H, H-6), 1.72 (m, 1H, H8), 1.82 (m, 1H, H-5), 1.98 (m, 1H, H-9), 2.13 (m, 1H, H-6), 2.21 (m, 1H, H-9), 2.34 (m, 1H, H-8), 3.26 (dd, 1H, J=18.9 Hz, J=12.1 Hz, $HCHN_3$), 3.65 (dd, 1H, $HCHN_3$), 4.09 (t, 1H, J=9.0 Hz, H-7), 4.42 (dd, 1H, H-3), 4.46 (dd, 1H, J=8.7 Hz, J=2.0 Hz, H-10), 5.12 (dd, 2H, J=15.7 Hz, J=12.2 Hz, $CH_2Ph$), 6.08 (d, 1H, J=7.18 Hz, NHCbz), 7.3-7.42 (m, 5H, aromatic protons). 13C NMR (100.6 MHz, $CDCl_3$): δ 170.5, 169.7, 156.6, 136.3, 128.5, 128.1, 81.6, 67.1, 60.9, 58.3, 55.9, 53.7, 40.9, 33.3, 31.9, 31.5, 28.0, 27.2. MS [ESI+]: 448.2 [M+H]+, 480.2 [M+Na]+, Calculated elemental analysis $C_{23}H_{31}N_5O_5$: C, 60.38; H, 6.83; N, 15.31; observed C, 60.36; H, 6.84; N, 15.32.

c) Reduction of Azide-Derivatives

To a solution of product 6 or 15 (0.034 mmol) in anhydrous $CH_2Cl_2$ (350 µl) under argon atmosphere and at room temp., is added 1M $Me_3P$ in toluene (51 µl, 0.051 mmol). After approx. 2 hours, upon completion of the reaction, the reaction is taken up with $CH_2Cl_2$ (1 ml), and $H_2O$ (1 ml) added, and the mixture is allowed under stirring for approx. 10 minutes. After this period of time, the two phases are separated. The organic phase, dried over $Na_2SO_4$, is evaporated to dryness.

Characterization of Compound 7

Yield: 93%. $[\alpha]_D^{22}$=−13.9 (c=1.0, $CHCl_3$). 1H-NMR (400 MHz, $CDCl_3$): δ 1.47 (s, 9H, $C(CH_3)_3$), 1.55 (m, 1H, H-5), 1.72 (m, 1H, H-7), 2.07 (m, 1H, H-8), 2.16 (m, 1H, H-8), 2.21 (m, 1H, H-7), 2.30 (m, 1H, H-5), 2.68 (m, 1H, H-4), 2.72-2.97 (m, 2H, $CH_2NH_2$), 3.73 (m, 1H, H-6), 4.31 (t, 1H, H-3), 4.41 (d, 1H, H-9), 5.15 (s, 2H, $CH_2Ph$), 6.4 (d, 1H, NHCbz), 7.23-7.42 (m, 5H, aromatic protons). 13C NMR (100.6 MHz, $CDCl_3$): δ 170.8, 168.1, 156.4, 136.6, 128.5, 128.0, 127.9, 81.8, 67.8, 58.9, 55.6, 53.0, 32.5, 32.0, 29.7, 29.3, 28.0. MS [ESI+]: 418.4 [M+H]+. Calculated elemental analysis $C_{22}H_{31}N_3O_5$: C, 63.29; H, 7.48; N, 10.06; observed C, 63.27; H, 7.47; N, 10.08.

Characterization of Compound 16

Yield: 76%. $[\alpha]_D^{22}$=−14.5 (c=1.0, $CHCl_3$). 1H-NMR (400 MHz, $CDCl_3$): δ 1.45 (s, 9H, $C(CH_3)_3$), 1.5 (m, 1H, H-5), 1.53 (m, 1H, H-4), 1.65 (m, 1H, H-6), 1.72 (m, 1H, H8), 1.81 (m, 1H, H-5), 1.98 (m, 1H, H-9), 2.14 (m, 1H, H-6), 2.21 (m, 1H, H-9), 2.33 (m, 1H, H-8), 2.83 (bs, 2H, CH$_2$NH$_2$), 4.08 (t, 1H, J=9.0 Hz, H-7), 4.41 (m, 1H, H-3), 4.47 (d, 1H, J=8.5 Hz, H-10), 5.13 (dd, 2H, J=15.7 Hz, J=12.2 Hz, CH$_2$Ph), 6.16 (d, 1H, J=7.0 Hz, NHCbz), 7.28-7.42 (m, 5H, aromatic protons). $^{13}$C NMR (100.6 MHz, CDCl$_3$): δ 170.6, 156.8, 136.2, 128.5, 128.0, 81.5, 67.0, 60.8, 58.3, 56.3, 44.4, 33.7, 32.0, 31.3, 28.0, 27.2. MS [ESI$^+$]: 432.5 [M+H]$^+$. Calculated elemental analysis C$_{23}$H$_{33}$N$_3$O$_5$: C, 64.02; H, 7.71; N, 9.74; observed C, 64.04; H, 7.72; N, 9.73

Preparation of Amide Derivatives of the Cyclic Pentapeptide Containing the RGD Sequence (Scheme 4 and Scheme 5)

a) Synthesis of Azide-Derivatives

To a solution of product 17-20 (0.055 mmol) in anhydrous CH$_2$Cl$_2$ (700 µl) under argon atmosphere and at room temp., are added in the following sequence MsCl (8.5 µl, 0.11 mmol) and TEA (30 µl, 0.22 mmol). The solution is kept under stirring for approx. 30 minutes. After this period of time, the solvent is evaporated to dryness and the crude product filtered over silica gel (CH$_2$Cl$_2$/MeOH 9:1). The crude product thus obtained is dissolved in DMF (55 µl) and, under argon atmosphere and at room temp., NaN$_3$ (36 mg, 0.55 mmol) is added. The reaction is kept under stirring at 80° C. for approx. 18 hours. After this period of time, the DMF is evaporated off to dryness, and the crude product dissolved in CH$_2$Cl$_2$ and washed with H$_2$O. The organic phase, dried over Na$_2$SO$_4$, is evaporated and the crude product thus obtained is purified by flash chromatography (CH$_2$Cl$_2$/iPrOH 9:1→8:2) to give the desired product as a white foam (30%-75%).

Characterization of Compound 21

Yield: 62%. (White solid). [α]$_D^{22}$=−6.3 (c=1.0, CHCl$_3$). $^1$H NMR (400 MHz, Acetone-D6): δ 1.23 (s, 6H, C(CH$_3$)$_2$ Pmc), 1.38 (s, 9H, C(CH$_3$)$_3$), 1.44 (m, 1H, Hβ Arg), 1.47 (m, 1H, H-7), 1.49 (m, 1-1H, H-8), 1.51 (m, 1H, Hβ Arg), 1.60 (m, 1H, H● Arg), 1.72 (m, 2H, CH$_2$CH$_2$Ar Pmc), 1.74 (m, 1H, H-5), 1.80 (m, 1H, Hγ Arg), 2.02 (s, 3H, CH$_3$ Pmc), 2.1 74 (m, 1H, H-5), 2.12 (m, 1H, H-4), 2.18 (m, 1H, H-7), 2.3 (m, 1H, H-8), 2.48 (s, 3H, CH$_3$ Pmc), 2.50 (s, 3H, CH$_3$ Pmc), 2.54 (m, 2H, CH$_2$CH$_2$Ar Pmc), 2.60 (m, 1H, Hβ Asp), 2.91 (m, 1H, Hβ Asp), 3.17 (m, 1H, Hδ Arg), 3.19 (m, 1H, CH$_2$N$_3$), 3.23 (m, 1H, Hδ Arg), 3.48 (m, 1H, CH$_2$N$_3$), 3.6 (m, 1H, Hα Gly), 3.8 (m, 1H, Hα Gly), 4.0 (m, 1H, H-6), 4.17 (m, 1H, H-9), 4.4 (m, 1H, H-3), 4.63 (m, 1H, Hα Arg), 4.72 (m, 1H, Hα Asp), 6.14 (bs, 1H, (NH)$_2$C=NH), 6.37 (bs, 2H, (NH)$_2$C=NH), 7.32-7.48 (m, 2H, NH Arg, NH bicyclic), 7.8 (bs, 1H, NH Gly), 8.12 (bs, 1H, NH Asp). $^{13}$C NMR HETCOR (400 MHz, Acetone-D6): δ 67.5, 54.8, 51.8, 51.4, 50.2, 49.4, 45.8, 40.1, 39.9, 34.7, 32.8, 31.8, 31.5, 30.2, 28.1, 27.2, 26.8, 25.2, 21.3, 18.5, 17.5, 12.1. MS [FAB$^+$]: calculated for C$_{40}$H$_{59}$N$_{11}$O$_{10}$S: 885.42, observed: 886 [M+H]$^+$. Calculated analysis for C$_{40}$H$_{59}$N$_{11}$O$_{10}$S: C, 54.22; H, 6.71; N, 17.39; observed C, 54.20; H, 6.72; N, 17.37.

Characterization of Compound 23

Yield: 30%. (White solid). [α]$_D^{22}$=−65.15 (c=1.0, Acetone). $^1$H NMR (400 MHz, Acetone-D6): δ 1.18 (m, 6H, C(CH$_3$)$_2$ Pmc), 1.3 (s, 9H, C(CH$_3$)$_3$), 1.44 (m, 1H, H-8), 1.45 (m, 3H, H-6, Hγ Arg), 1.5 (m, 1H, Hβ Arg), 1.57 (m, 1H, Hβ Arg), 1.62 (m, 1H, H-4), 1.65 (m, 1H, H-5), 1.7 (m, 2H, CH$_2$CH$_2$Ar Pmc), 1.73 (m, 2H, H-5, H-9), 1.95 (m, 1H, H-9), 1.96 (s, 3H, CH$_3$ Pmc), 1.98 (m, 1H, H-6), 2.13 (m, 1H, H-8), 2.46 (s, 3H, CH$_3$ Pmc), 2.48 (s, 3H, CH$_3$ Pmc), 2.55 (m, 2H, CH$_2$CH$_2$Ar Pmc), 2.7 (m, 1H, Hβ Asp), 2.78 (m, 1H, Hβ Asp), 3.07 (m, 1H, HCHN$_3$), 3.11 (m, 2H, Hδ Arg), 3.56 (m, 1H, HCHN$_3$), 3.63 (m, 1H, Hα Gly), 3.87 (m, 1H, H-7), 3.93 (m, 1H, Hα Gly), 4.33 (m, 1H, Hα Asp), 4.35 (m, 1H, H-3), 4.42 (m, 1H, Hα Arg), 4.64 (m, 1H, H-10), 6.25 (bs, 1H, (NH)$_2$C=NH), 6.36 (bs, 2H, (NH)$_2$C=NH), 7.46 (m, 1H, NH bicyclic), 7.77-7.9 (m, 2H, NH Gly, NH Arg), 8.05 (bs, 1H, NH Asp). $^{13}$C NMR HETCOR (400 MHz, Acetone-D6): δ 61.2, 58.9, 53.5, 53.3, 53.1, 51.4, 43.6, 40.3, 39.6, 36.3, 33.3, 33.1, 31.6, 28.7, 27.3, 26.9, 26.1, 25.8, 25.5, 21.0, 18.0, 16.9, 11.4. MS [ESI$^+$]: calculated for C$_{41}$H$_{61}$N$_{11}$O$_{10}$S: 899.43, observed: 900.9 [M+H]$^+$. Calculated analysis for C$_{41}$H$_{61}$N$_{11}$O$_{10}$S: C, 54.71; H, 6.83; N, 17.12; observed C, 54.73; H, 6.82; N, 17.11.

Characterization of Compound 25

Yield: 60%. (White solid). [α]$_D^{22}$=−65.83 (c=1.15, CHCl$_3$). $^1$H NMR (400 MHz, Acetone-D6): δ 1.27 (m, 1H, H-5), 1.30 (s, 6H, C(CH$_3$)$_2$ Pmc), 1.45 (s, 9H, C(CH$_3$)$_3$), 1.52 (m, 1H, Hβ Arg), 1.59 (m, 1H, H-7), 1.60 (m, 1H, Hγ Arg), 1.62 (m, 1H, Hβ Arg), 1.81 (m, 2H, CH$_2$CH$_2$Ar Pmc), 1.98 (m, 1H, Hγ Arg), 2.0 (m, 1H, H-8), 2.1 (s, 3H, CH$_3$ Pmc), 2.38 (m, 1H, H-5), 2.42 (m, 1H, H-7), 2.43 (m, 1H, H-8), 2.56 (s, 3H, CH$_3$ Pmc), 2.58 (s, 3H, CH$_3$ Pmc), 2.6 (m, 1H, Hβ Asp), 2.62 (m, 2H, CH$_2$CH$_2$Ar Pmc), 2.9 (m, 1H, H-4), 2.95 (m, 1H, Hβ Asp), 3.19 (m, 1H, Hδ Arg), 3.25 (m, 1H, Hδ Arg), 3.37 (m, 2H, CH$_2$N$_3$), 3.62 (d, 1H, J=13.3 Hz, Hα Gly), 4.1 (m, 1H, H-6), 4.12 (m, 1H, Hα Gly), 4.25 (m, 2H, H-9), 4.39 (m, 1H, H-3), 4.6 (m, 1H, Hα Arg), 4.67 (m, 1H, Hα Asp), 6.12 (bs, 1H, (NH)$_2$C=NH), 6.35 (bs, 2H, (NH)$_2$C=NH), 7.32-7.48 (m, 2H, NH Arg, NH bicyclic), 7.82 (bs, 1H, NH Gly), 8.1 (bs, 1H, NH Asp). $^{13}$C NMR HETCOR (400 MHz, Acetone-D6): δ 62.5, 55.7, 53.4, 51.2, 42.7, 40.6, 40.3, 36.3, 35.5, 34.9, 33.4, 33.3, 30.0, 28.4, 28.3, 27.5, 26.0, 22.1, 20.8, 17.9, 16.7, 13.2, 11.4. MS [FAB$^+$]: calculated for C$_{40}$H$_{59}$N$_{11}$O$_{10}$S: 885.42, observed: 886 [M+H]$^+$. Calculated analysis for C$_{40}$H$_{59}$N$_{11}$O$_{10}$S: C, 54.22; H, 6.71; N, 17.39; observed C, 54.21; H, 6.73; N, 17.38.

Characterization of Compound 27

Yield: 75%. (White solid). [α]$_D^{22}$=−35.74 (c=1.2, CHCl$_3$). $^1$H-NMR (400 MHz, CDCl$_3$): δ 1.32 (s, 6H, C(CH$_3$)$_2$ Pmc), 1.46 (s, 9H, C(CH$_3$)$_3$), 1.48 (m, 1H, H-6), 1.5 (m, 1H, Hβ Arg), 1.60 (m, 1H, Hγ Arg), 1.62 (m, 1H, Hβ Arg), 1.65 (m, 1H, H-5), 1.7 (m, 1H, H-4), 1.73 (m, 1H, H-8), 1.82 (m, 2H, CH$_2$CH$_2$Ar Pmc), 1.96 (m, 1H, Hγ Arg), 2.02 (m, 1H, H-9), 2.1 (m, 1H, H-5), 2.11 (s, 3H, CH$_3$ Pmc), 2.21 (m, 1H, H-4), 2.23 (m, 1H, H-9), 2.45 (m, 1H, Hβ Asp), 2.56 (s, 3H, CH$_3$ Pmc), 2.58 (s, 3H, CH$_3$ Pmc), 2.64 (m, 2H, CH$_2$CH$_2$Ar Pmc), 2.87 (m, 1H, Hβ Asp), 3.18 (m, 2H, Hδ Arg), 3.22 (m, 1H, HCHN$_3$), 3.53 (d, 1H, J=13.0 Hz, Hα Gly), 3.62 (m, 1H, HCHN$_3$), 4.24 (m, 1H, H-7), 4.26 (m, 1H, Hα Gly), 4.41 (m, 2H, H-10), 4.59 (m, 1H, Hα Arg), 4.61 (m, 1H, H-3), 4.96 (m, 1H, Hα Asp), 6.32 (bs, 3H, (NH)$_2$C=NH), 7.46-7.58 (m, 3H, NH Gly, NH Arg, NH bicyclic), 7.9 (bs, 1H, NH Asp). $^{13}$C NMR HETCOR (400 MHz, CDCl$_3$): δ 63.4, 58.9, 55.0, 53.8, 51.9, 49.7, 44.3, 40.5, 39.3, 35.2, 33.0, 32.5, 32.6, 31.2, 28.0, 27.8, 26.7, 25.3, 21.3, 18.6, 17.3, 11.9. MS [FAB$^+$]: calculated for C$_{41}$H$_{61}$N$_{11}$O$_{10}$S: 899.43, observed: 901 [M+H]$^+$. Calculated analysis for C$_{41}$H$_{61}$N$_{11}$O$_{10}$S: C, 54.71; H, 6.83; N, 17.12; observed C, 54.70; H, 6.83; N, 17.11.

b) Hydrogenation of the Azide Group

To a solution of product 21, 23, 25 or 27 (0.03 mmol) in MeOH (1 ml) is added a catalytic amount of 10% Pd/C. The suspension is kept stirring under hydrogen atmosphere for 4 hours. After this period of time the reaction mixture is filtered over a bed of Celite, the organic phase is evaporated to dryness and the crude amines are used in the following reaction without any further purification.

c) Synthesis of the Amides 22, 24, 26 and 28

To a solution of R$_6$COOH (0.043 mmol) and HBTU (0.050 mmol) in anhydrous CH$_2$Cl$_2$ (0.5 mL), a solution of 21-NH$_2$ (or 23-NH$_2$ or 25-NH$_2$ or 27-NH$_2$) (0.023 mmol) and DIPEA (0.115 mmol) in anhydrous CH$_2$Cl$_2$ (0.5 mL) was added dropwise. The reaction mixture was stirred at room temperature for 18 h then a further amount of CH$_2$Cl$_2$ (3 mL) was added. The solution was washed with saturated aqueous NaHCO$_3$ (3×5 mL) and then with 1M aqueous KHSO$_4$ (1×5 mL). The organic phase was separated, dried (Na$_2$SO$_4$) and evaporated. The residue was purified by flash-chromatography. The solid obtained was dissolved in TFA/thioanisole/1,2-ethandithiol/anisole (90:5:3:2, v/v/v/v; 1 mL) and the solution was stirred for 4 h at room temperature. The mixture was evaporated, the residue dissolved in H$_2$O (4 mL) and the solution washed with diisopropyl ether (2×5 mL). The aqueous phase was evaporated and the residue purified by preparative HPLC (eluent A: 97% H$_2$O, 3% CH$_3$CN+0.1% TFA; eluent B: CH$_3$CN+0.1% TFA; flow: 4 mL/min; stationary phase: Waters X-terra RP18 column 5 μm, 19×50 mm; detection: UV, k: 220 nm) to obtain product 22 (or 24 or 26 or 28) as white solid.

Preparation of Chelating Ligands

Preparation of the compound 5 of FIG. 8A, hereinafter referred to as compound F.

a) Preparation of the Intermediate B

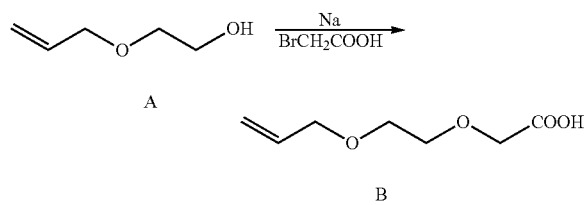

2-Allyloxyethanol A (20.2 mL; 19.2 g; 189 mmol) was dissolved in anhydrous THF (115 mL) and Na (4.12 g; 1.18 mmol) was added in little portions at 0° C. The mixture was stirred at room temperature for 2 h then anhydrous THF (22 mL) was added affording the precipitation of a white solid. The suspension was stirred at room temperature for 1 day. Bromoacetic acid (12.4 g; 0.09 mmol) dissolved in anhydrous THF (20 mL) was added dropwise and the solution was stirred for 48 h. The mixture was diluted with EtOH (150 mL) and then water (20 mL) keeping the temperature at 0° C. The solvents were evaporated under vacuum to obtain a yellow oil. The residue was dissolved in water (150 mL) and the solution washed with Et$_2$O (2×100 mL) and CHCl$_3$ (2×100 mL). 37% HCl was added to the aqueous phase to reach pH 1 and the solution was extracted with CHCl$_3$ (4×100 mL). The organic layer was separated, dried (Na$_2$SO$_4$) and evaporated under vacuum to obtain compound B (5.42 g; 71.8 mmol). Yield 38%.

MS (ESI$^+$): C$_7$H$_{12}$O$_4$; calc. 160.07. found 161.1 (M+H)$^+$.

b) Preparation of the Intermediate C

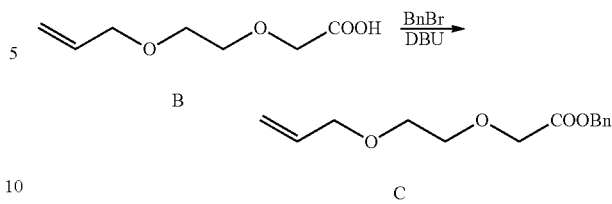

A solution of benzyl bromide (4.56 mL; 6.57 g; 38.0 mmol) in toluene (30 mL) was added dropwise to a solution of compound B (5.13 g; 32.0 mmol) and DBU (4.77 mL; 4.87 g; 32.0 mmol) in toluene (70 mL). After 2 h the mixture was filtered and evaporated under vacuum. The residue was dissolved in CHCl$_3$ (50 mL) and the solution washed with water (3×50 mL). The organic layer was separated, dried (Na$_2$SO$_4$) and evaporated under vacuum. The residue (7.23 g) was purified by flash-chromatography (eluent: 80:20 v/v petroleum ether/EtOAc) to obtain compound C (5.40 g; 21.6 mmol) as a yellow oil. Yield 68%.

MS (ESI$^+$): C$_{14}$H$_{18}$O$_4$; calc. 250.12. found 251.1 (M+H)$^+$.

c) Preparation of the Intermediate D

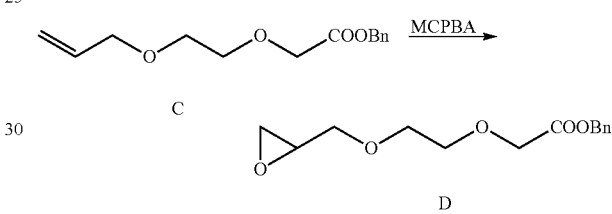

A solution of MCPBA (3.96 g; 23.0 mmol) in CHCl$_3$ (70 mL) was added dropwise into a solution of compound C (5.20 g; 21.0 mmol) in CHCl$_3$ (50 mL). The mixture was stirred for 48 h then washed with 10% aq. Na$_2$SO$_3$ (3×150 mL) and water (3×150 mL). The organic layer was separated, dried (Na$_2$SO$_4$) and evaporated under vacuum. The residue (4.88 g) was purified by flash-chromatography (eluent: 1:1 v/v CH$_2$Cl$_2$/Et$_2$O) to obtain compound D (4.05 g; 15.1 mmol) as a yellow oil. Yield 72%

MS (ESI$^+$): C$_{14}$H$_{18}$O$_5$; calc. 266.12. found 267.1 (M+H)$^+$.

d) Preparation of the Intermediate E

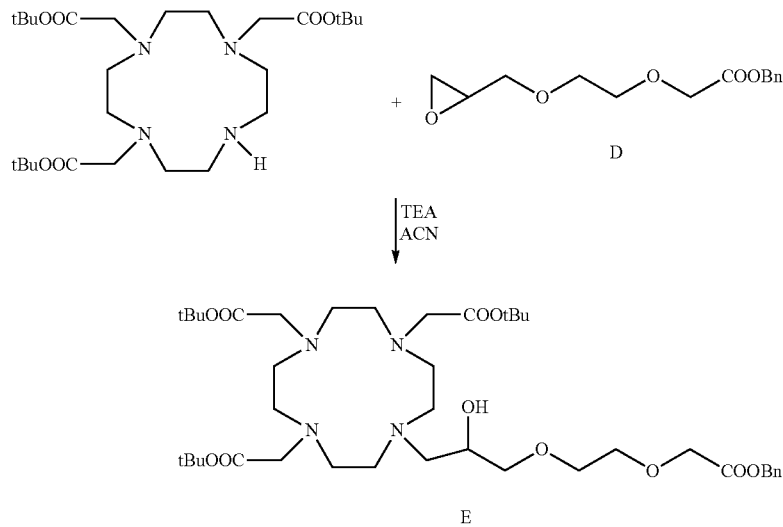

A solution of compound D (2.44 g; 9.20 mmol) in MeCN (30 mL) was added dropwise into a solution of DO3A tris-tert-butylester (3.19 g; 6.20 mmol) and triethylamine (1.27 mL; 9.20 mmol) in MeCN (30 mL). The mixture was stirred at 50° for 32 h then cooled to room temperature and evaporated under vacuum. The residue was dissolved in CHCl$_3$ (50 mL) and the solution washed with water (50 mL) and brine (50 mL). The organic layer was separated, dried (Na$_2$SO$_4$) and evaporated under vacuum. The residue (6.48 g) was purified by flash-chromatography (eluent 9:1:0.1 v/v/v CHCl$_3$/MeOH/NH$_4$OH) to obtain compound E (2.87 g; 3.66 mmol) as a yellow oil. Yield 59%.

MS (ESI$^+$: C$_{40}$H$_{68}$N$_4$O$_{11}$; calc. 780.49. found 803.5 (M+Na)$^+$.

e) Deprotection of E to Give the Product F

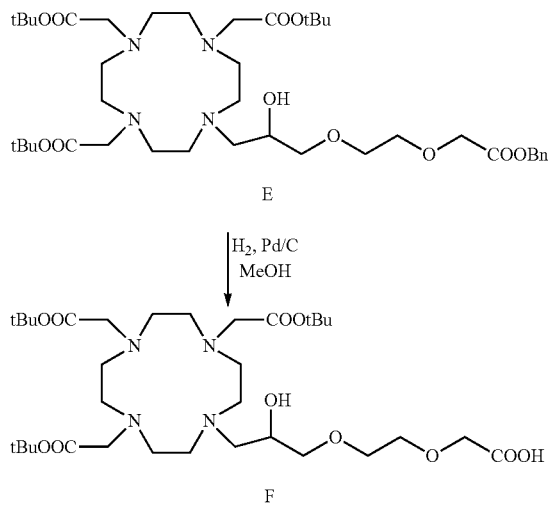

10% Pd/C (28 mg) was added to a solution of intermediate E (140 mg; 0.18 mmol) in MeOH (10 mL). The reaction mixture was stirred under an hydrogen atmosphere for 2 h then filtered through Millipore® apparatus (FH 0.5 μm) and evaporated to give the compound F (110 mg; 0.16 mmol) as a white oil. Yield 88%.

MS (ESI$^+$): C$_{33}$H$_{62}$N$_4$O$_{11}$; calc. 690.44. found 713.4 (M+Na)$^+$.

Linkers

Preferred molecules useful as linkers according to the present invention and listed in Table 1 are well known, and already marketed or they may be easily prepared according to cited literature and/or known synthetic procedures.

The preparation of the compound A32 of table 1 is included below as non limiting examples.

The starting compound of formula

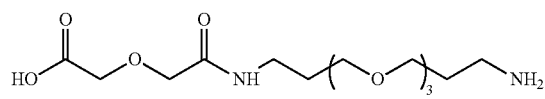

was prepared according to Arosio, D. et al., *Org. Biomol. Chem.* 2004, 2, 2113-2124. The amino group of this compound was protected with CbzCl.

The NBoc derivative was coupled with propargylamine and the Boc protecting group was removed to give the desired compound according to scheme 7 below

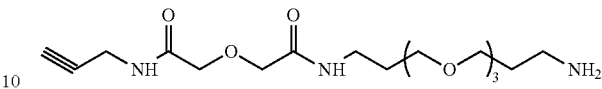

Preparation of Compounds According to Formula (III)

a) Biotinilated Derivatives and Fluorescent Derivatives

The preparation of the biotinilated and fluorescent derivatives comprises the following steps:

1) Preparation of the azide derivatives of the peptidomimetic compound.

This preparation has been performed as above described, and schematized in scheme 6 below.

Scheme 6

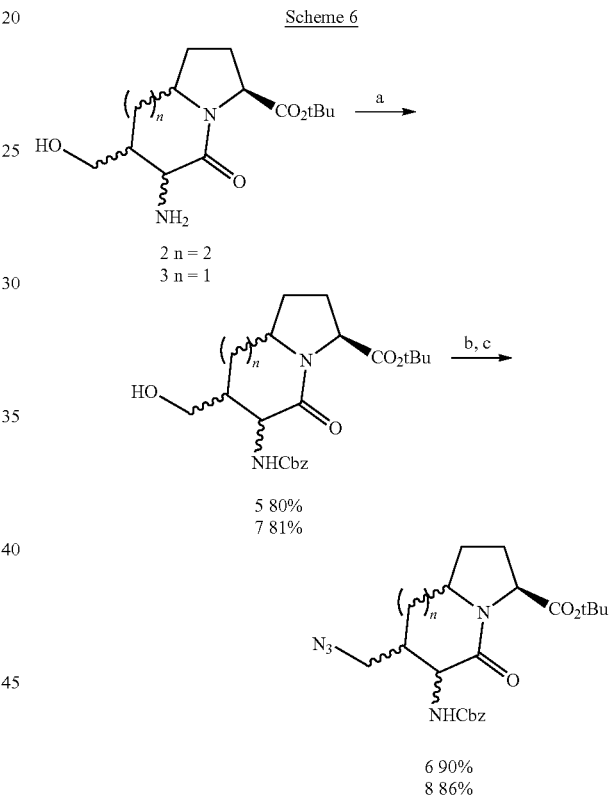

2) Preparation of the linker (A32);

3) coupling of the linker with the biotin and fluoresceine residues

The coupling reactions have been performed according to the following scheme 7:

Scheme 7

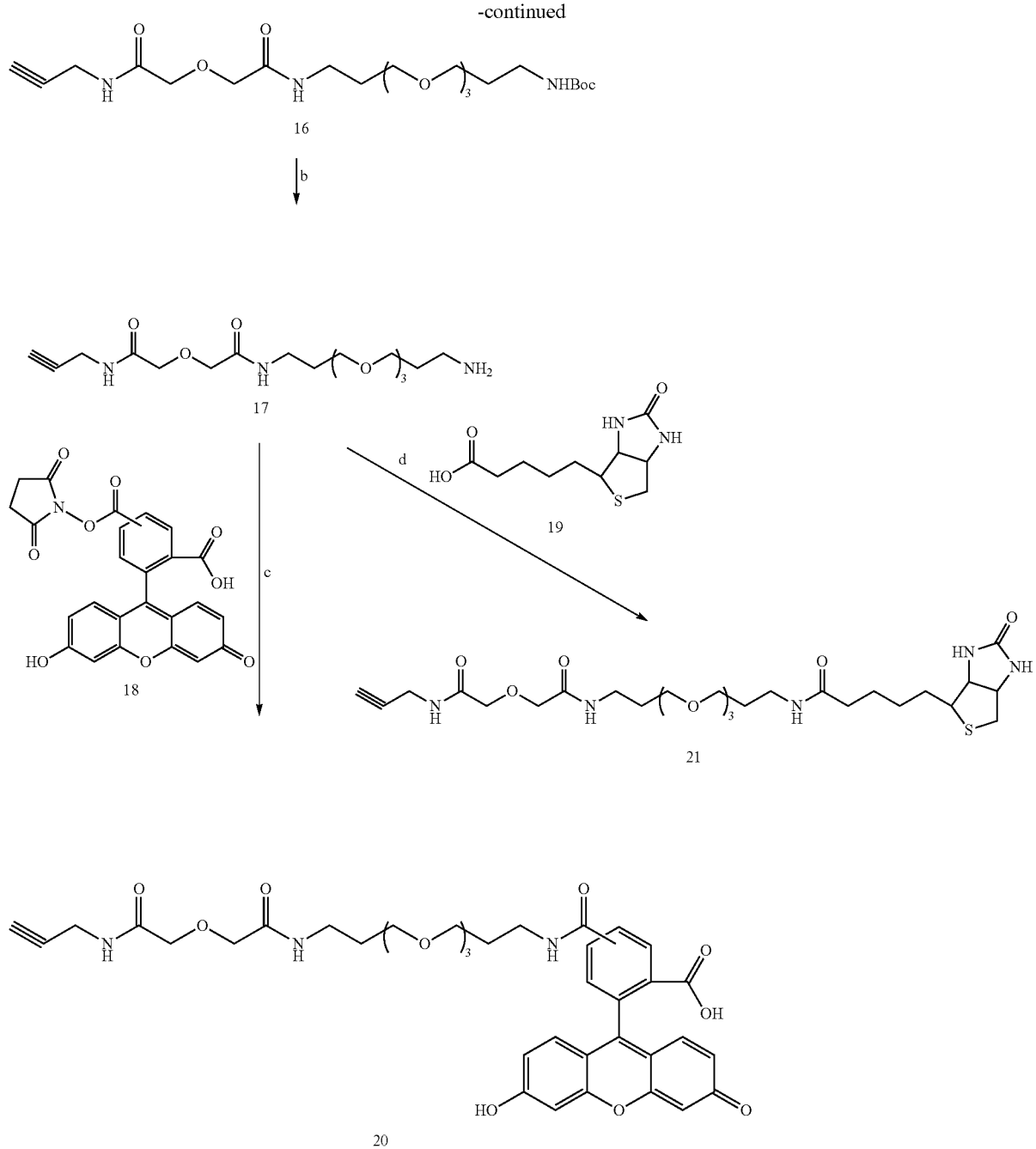

The linker, compound 17 of the scheme, was conjugated to biotin molecule 19 using HBTU and DIPEA. The conjugation with fluorescein, to give the desired conjugated compound 20, was performed adding commercially available 5(6)-carboxyfluorescein-N-hydroxysuccinimide ester 18 to a basic solution of 17.

4) coupling reaction between the intermediate 6, 8 and 20, 21 to provides the compounds 22, 23, 24 and 25.

This step has been performed as per the following scheme 8:

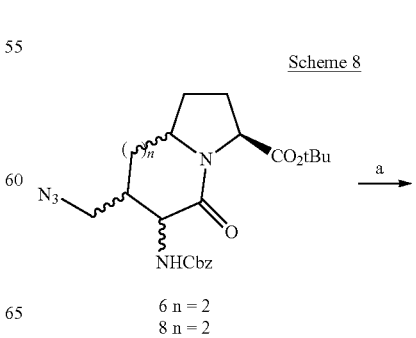

Scheme 8

6 n = 2
8 n = 2

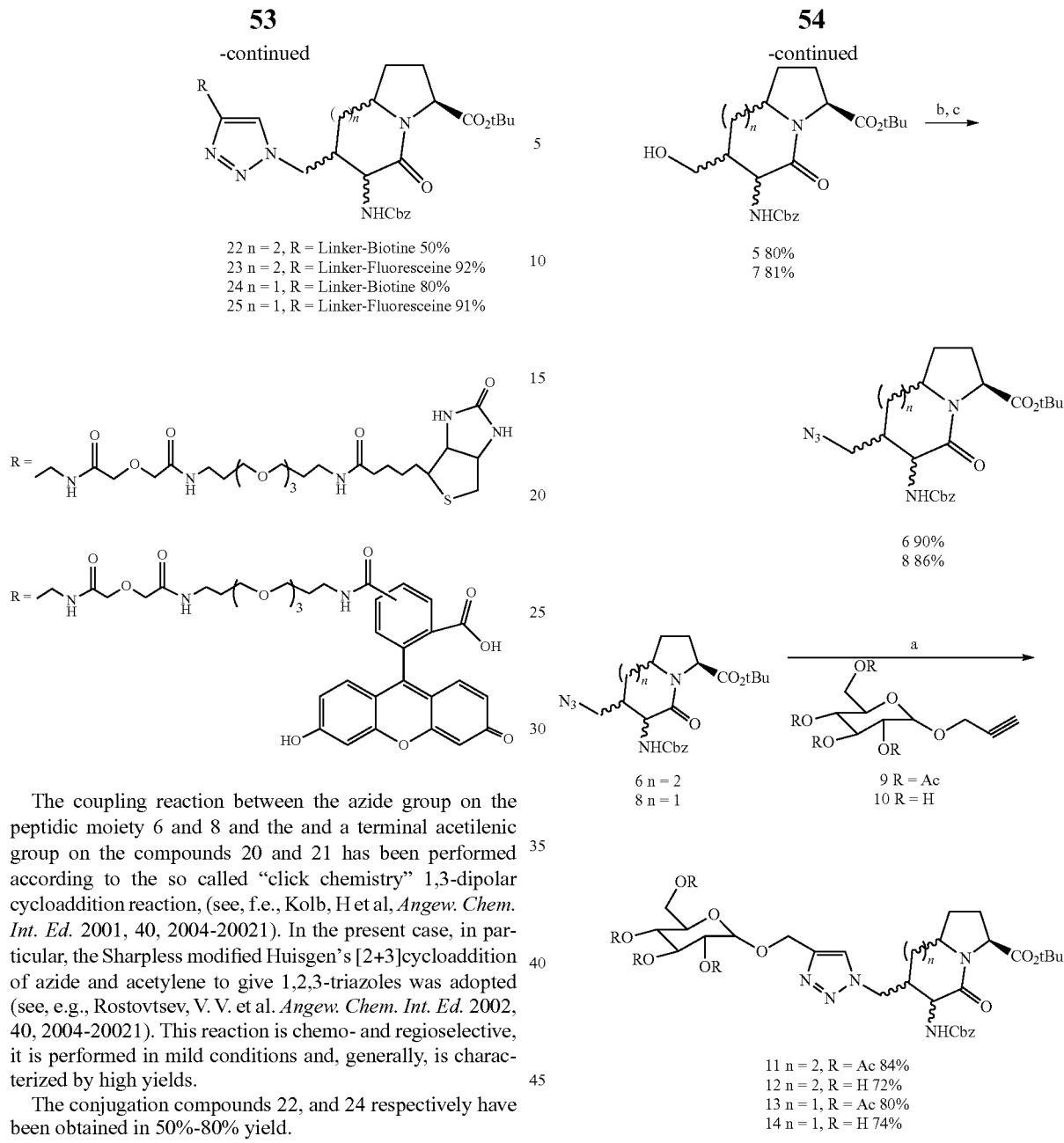

22 n = 2, R = Linker-Biotine 50%
23 n = 2, R = Linker-Fluoresceine 92%
24 n = 1, R = Linker-Biotine 80%
25 n = 1, R = Linker-Fluoresceine 91%

5 80%
7 81%

6 90%
8 86%

6 n = 2
8 n = 1

9 R = Ac
10 R = H 11 n = 2, R = Ac 84%
12 n = 2, R = H 72%
13 n = 1, R = Ac 80%
14 n = 1, R = H 74%

The coupling reaction between the azide group on the peptidic moiety 6 and 8 and the and a terminal acetilenic group on the compounds 20 and 21 has been performed according to the so called "click chemistry" 1,3-dipolar cycloaddition reaction, (see, f.e., Kolb, H et al, *Angew. Chem. Int. Ed.* 2001, 40, 2004-20021). In the present case, in particular, the Sharpless modified Huisgen's [2+3]cycloaddition of azide and acetylene to give 1,2,3-triazoles was adopted (see, e.g., Rostovtsev, V. V. et al. *Angew. Chem. Int. Ed.* 2002, 40, 2004-20021). This reaction is chemo- and regioselective, it is performed in mild conditions and, generally, is characterized by high yields.

The conjugation compounds 22, and 24 respectively have been obtained in 50%-80% yield.

The same reaction performed between 6 or (and the fluoresceine tag 20, gave the final compounds 23 and 25 in higher yields (91%-92%)

b) Sugar Derivatives

The preparation has been performed according to the procedure schematized below in Scheme 9:

Scheme 9

2 n = 2
3 n = 1

The compounds 11, 12, 13, and 14 have been prepared by 1,3-dipolar cycloaddition between pseudopeptides 6 and 8 and 1-O-propargyl 2,3,4,6-tetra-O-acetyl-β-D-glucose 9 or 1-O-propargyl-β-D-glucose 10. The cycloaddition was performed using Cu(OAc)$_2$ and Na ascorbate as catalyst in tBuOH/H2O 1:1 as per scheme 9. The reaction proceeded overnight at room temperature and the desired products were isolated, after purification by falsh chromatography in good yields.

c) Chelated Complex Derivatives

Preparation of the Chelated Complex 1

The preparation has been performed according to the procedure schematized below in Scheme 10.

Scheme 10
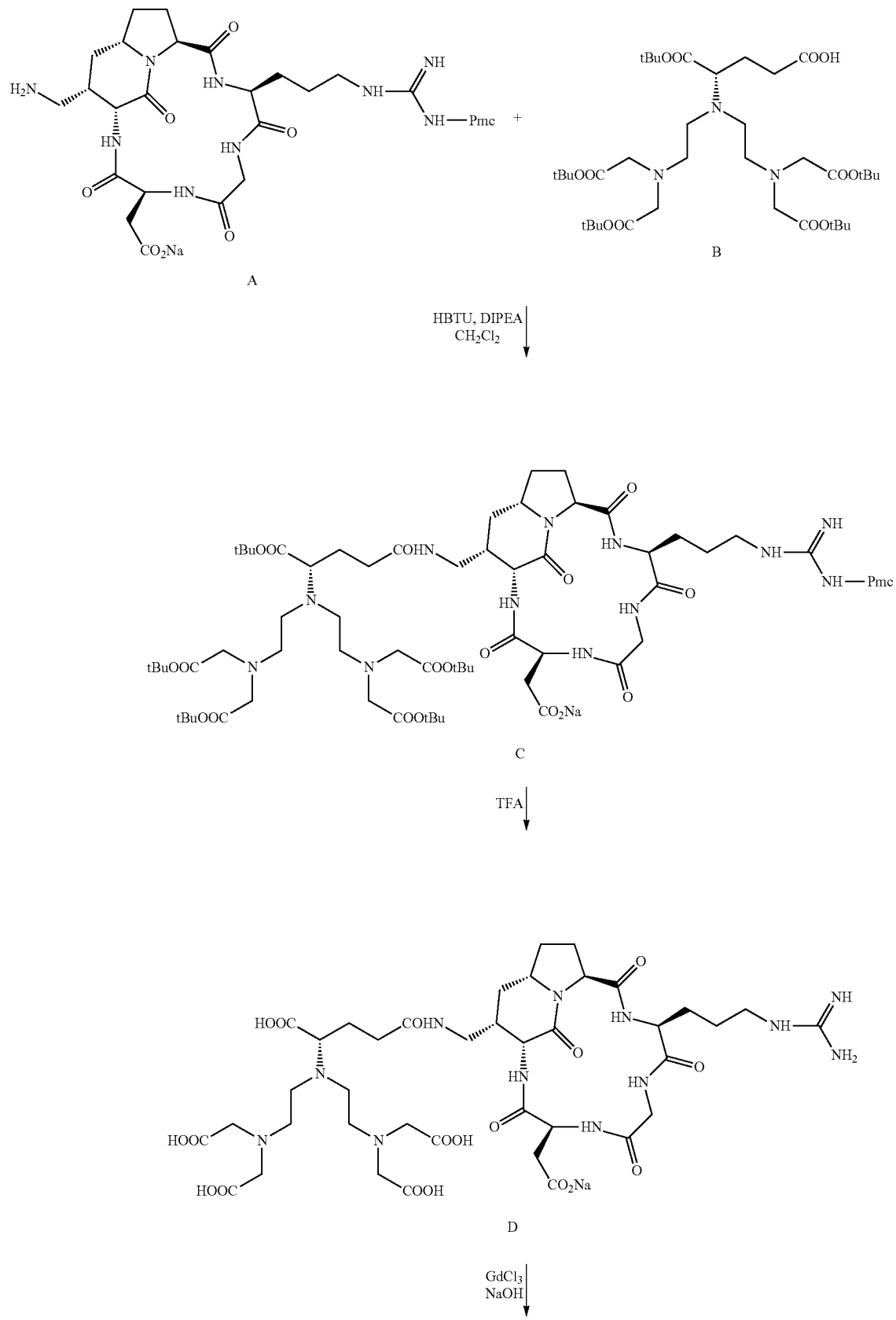

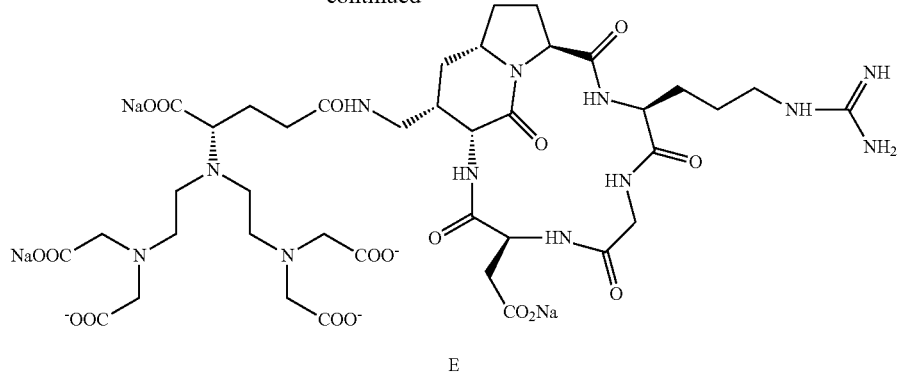

E a) Preparation of the Intermediate C

To a solution of compound B (0.043 mmol) and HBTU (0.050 mmol) in anhydrous $CH_2Cl_2$ (0.5 mL), a solution of A (0.023 mmol) and DIPEA (0.115 mmol) in anhydrous $CH_2Cl_2$ (0.5 mL) was added dropwise. The reaction mixture was stirred at room temperature for 18 h then a further amount of $CH_2Cl_2$ (3 mL) was added. The solution was washed with saturated aqueous $NaHCO_3$ (3×5 mL) and then with 1M aqueous KHSO4 (1×5 mL). The organic phase was separated, dried ($Na_2SO_4$) and evaporated. The residue was purified by flash-chromatography (eluent: 9:1 $CH_2Cl_2$/MeOH, v/v; stationary phase: $SiO_2$) affording product C (0.013 mmol) as a white solid. Yield 57%. MS [ESI+] for $C_{77}H_{126}N_{12}O_{21}S$: calc. 1586.89. found 794.7 $[M+2H]^{2+}$.

b) Preparation of the Intermediate D

A solution of product C (0.013 mmol) in TFA/thioanisole/1,2-ethandithiol/anisole (90:5:3:2, v/v/v/v; 1 mL) was stirred for 4 h at room temperature. The mixture was evaporated, the residue dissolved in $H_2O$ (4 mL) and the solution washed with diisopropyl ether (2×5 mL). The aqueous phase was evaporated and the residue purified by preparative HPLC (eluent A: 97% $H_2O$, 3% $CH_3CN$+0.1% TFA; eluent B: $CH_3CN$+0.1% TFA; flow: 4 mL/min; stationary phase: Waters X-terra RP18 column 5 µm, 19×50 mm; detection: UV, λ: 220 nm) to obtain product D (0.012 mmol) as a white solid. Yield 93%.

MS [ESI+] for $C_{39}H_{60}N_{12}O_{18}$: calc. 984.41. found 985.4 $[M+H]^+$, 493.2 $[M+2H]^{2+}$.

c) Preparation of the Intermediate E

To a solution of compound D (0.010 mmol) in $H_2O$ (5 mL) a 6.20 mM aqueous solution of $GdCl_3$ (1.77 mL) was slowly added adjusting the pH to 7 with 0.05 M aqueous NaOH (0.605 mL). The mixture was loaded onto a XAD 16.00 column (5 mL) and the desired compound was eluted with a MeCN/$H_2O$ gradient. The fractions containing the product were evaporated to give compound E (0.009 mmol) as a white solid. Yield 90%.

MS [ESI+] for $C_{39}H_{57}GdN_{12}O_{18}$: calc. 1139.32. found 569.7 $[M+2H]^2$.

Preparation of the Chelated Complex 2

The preparation has been performed according to the procedure schematized below in Scheme 11.

Scheme 11

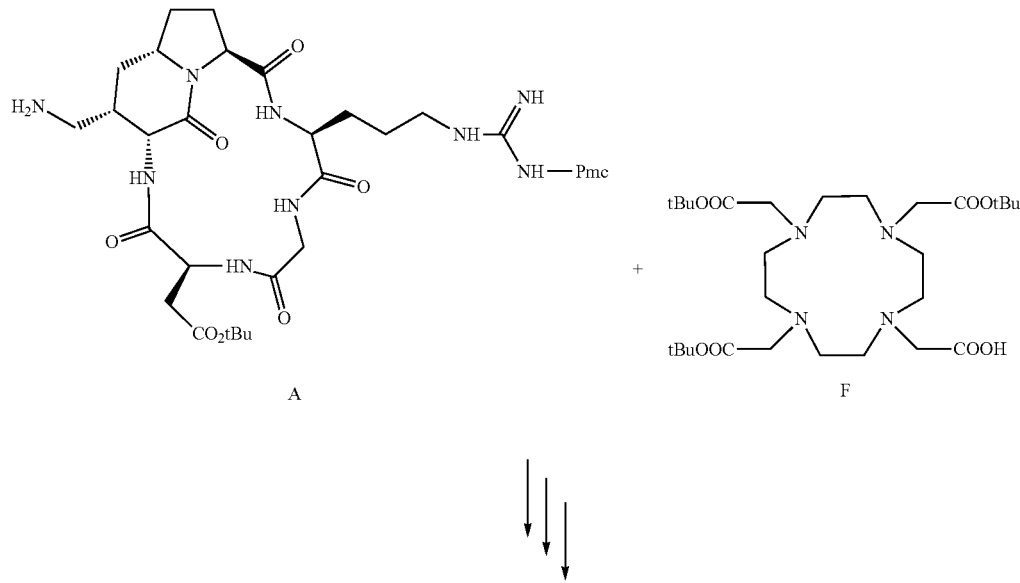

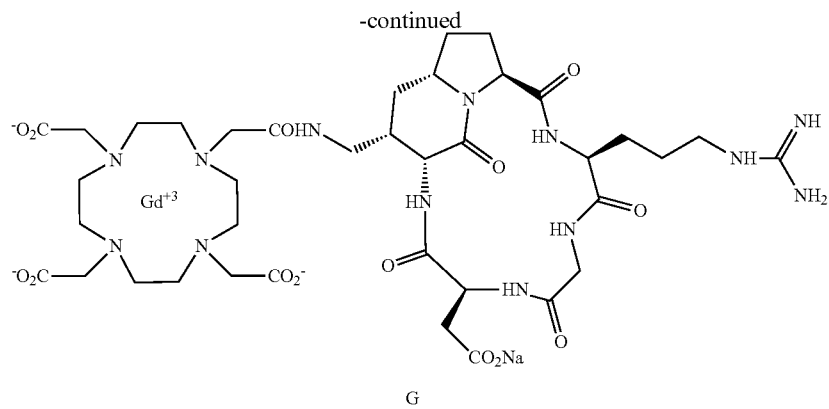

G

Preparation of the Product G

The same procedure described in Scheme 10 was applied to compounds A and F to obtain product G.

Chelated Complexes

Generally speaking, the paramagnetic complexes of the invention and, particularly, the Gd(III) chelated may be prepared by stoichiometric addition of suitable Gd(III) derivatives, particularly Gd(III) salts or oxides.

Preferably, Gd(III) chloride or oxide is employed by working according to well known experimental methods, for instance as reported in EP 230893.

d) Lipid Derivatives

The preparation of the peptidomimetic derivative I including a N-Succinyl-dioctadecylamine moiety as lipophilic unit was performed according to the procedure schematized below in Scheme 12.

Scheme 12

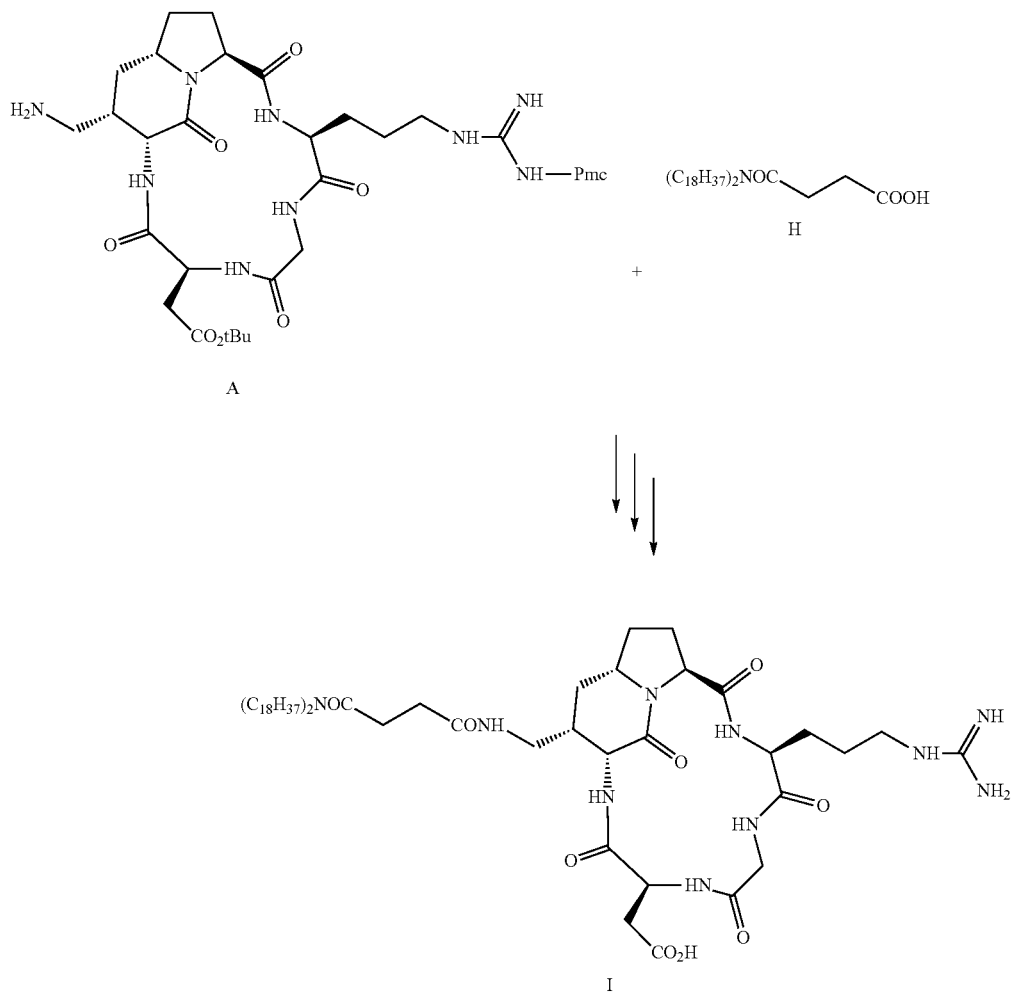

In particular, the same procedure described in Scheme 10 was applied to compounds A and H to obtain product I.

Multimeric Aggregate of the Invention

LIPOCEST as MR Imaging Reporters

With LIPOCEST as MR Imaging detectable moiety, as used herein, we intend a paramagnetic liposomes that act as CEST agents (LIPOCEST agents) for use in CEST imaging protocols.

LIPOCEST agents according to the invention can be prepared following any established protocols for liposome preparation.

The most used procedure for preparing large unilamellar liposomes (LUV) is the "thin film hydration method".

Briefly, a mixture of the lipidic components of the liposome membrane (phospholipids, cholesterol, amphiphilic paramagnetic complex at a given molar ratio) are dissolved in an organic solvent (usually a chloroform/methanol mixture). The solvent is slowly evaporated in order to obtain a thin lipidic film which is further dried under vacuum for ca. 2 h. The film is hydrated, at a given temperature (usually ca. 55° C.) and under vortexing, with an aqueous solutions which may contain the hydrophilic paramagnetic metal complex to be encapsulated. This solution can be ipo-, iso, or hyper-tonic. The resulting suspension containing multilamellar vesiscles (MLV) is extruded several times (usually ≥5) through polycarbonate filters with well-defined pore size (50 to 200 nm). After the extrusion, the paramagnetic metal complex which has not encapsulated is exhaustively removed by dialysis against an isotonic buffer. Besides the typical liposome characterisation (determination of size, polydispersity, Zeta potential, and the like), LIPOCEST agents have to be studied in order to determine: i) the chemical shift difference between the resonances of intraliposomal water and of that of the extraliposomal water proton, and ii) their ST efficiency.

$\Delta^{LIPO}$ values can be simply determined by recording a $^1$H-NMR spectrum of the LIPOCEST suspension. Alternatively, the same information can be gained by collecting a Z-spectrum, in which the intensity of the water proton signal is measured as a function of the irradiation frequency. Besides the $\omega^{LIPO}$ determination, the Z-spectrum is very useful for assessing the saturation transfer efficiency of the LIPOCEST agent. This is usually done by plotting the data obtained in the Z-spectrum in the ST % form.

According to the osmolarity of the aqueous solution used for hydrating the lipidic film, LIPOCEST agents can be classified in two main groups:
i) standard LIPOCEST (S-LIPOCEST), if the aqueous solution is iso- or hyper-tonic. The paramagnetic metal complex can be only encapsulated (S-LIPOCEST-E), only incorporated in the membrane (S-LIPOCEST-I), or both (S-LIPOCEST-EI).
ii) not-standard LIPOCEST (NS-LIPOCEST), if the aqueous solution is ipotonic.

The paramagnetic metal complex can be only encapsulated (NS-LIPOCEST-E), only incorporated (NS-LIPOCEST-I), or both (NS-LIPOCEST-EI)

The most important difference between S- and NS-LIPOCEST agents is that the latter display larger $\Delta^{LIPO}$ values.

Analogously to liposomes, LIPOCEST agents can be sterically protected in order to increase their in vivo stability. Usually, this is done by incorporating PEGylated phospholipids in the membrane.

Targeting LIPOCEST agents can be prepared by using two main approaches:
according to the first one, the recognition vector is incorporated in the liposome membrane and the LIPOCEST agent can interact directly to the biological target.
according to the second one the LIPOCEST-target recognition is indirect and the two units can interact through the presence of a third component which promotes the recognition. For instance if both the vector and the LIPOCEST are biotinylated, the targeting protocol requires the presence of avidin or streptavidin. The biotinylation of the LIPOCEST can be successfully carried out by incorporating in the membrane biotinylated phospholipids.

The following examples may best disclose this aspect of the invention.

Example 1

Preparation and Characterisation of Biotinylated LIPOCEST Agents Encapsulating [Tm-20]$^-$ Preparation 1-Palmitoyl-2-Oleoyl-sn-Glycero-3-Phosphocholine (POPC), Cholesterol, and 1,2-Distearoyl-sn-Glycero-3-Phosphoethanolamine-N-[Biotinyl(Polyethylene Glycol) 2000](Ammonium Salt) (DSPE-PEG2000Biotin) were dissolved in a chloroform/methanol 3:1 mixture. The molar ratio of the components (POPC/Chol/DSPE-PEG2000-Biotin) was 55:40:5 and the total amount of lipids was 20 mg.

The solution was slowly evaporated in order to obtain a thin lipidic film which was further dried under vacuum for 2 hours.

The film was hydrated with 1 mL of a solution of [Tm-20]$^-$ 0.2 M. (chelator 20 structure is shown in of FIG. 8C) The suspension was vortexed at 55° C. and then extruded (55° C., 4000 kPa) 5 times through polycarbonate filters (diameter 200 nm).

The resulting biotinylated liposomes were dialysed in order to remove the not-encapsulated metal complex (two dialysis cycles of 4 hours each against an isotonic buffer at pH 7).

Characterisation

The mean size of this LIPOCEST preparation was 250 nm (PDI=0.08).

FIG. 10 reports the $^1$H-NMR spectrum (14.1 T, 298 K) of this preparation. The chemical shift difference between intraliposomal and bulk water was 3 ppm.

FIG. 11 reports the normalised Z-spectrum of this preparation (7 T, irrad. pulse: rectangular, irrad. power 6 mT, irrad. time 2 s, 312 K). The occurrence of the saturation transfer is evident by looking at the hump visible in the downfield side of the spectrum.

FIG. 12 reports the corresponding ST-spectrum of this preparation. A ST % of ca. 70% was observed at 3 ppm from bulk water.

Example 2

Preparation and Characterisation of Biotinylated LIPOCEST Agents Incorporating Tm-21a and Encapsulating [Tm-20]$^-$ Preparation 1-Palmitoyl-2-Oleoyl-sn-Glycero-3-Phosphocholine (POPC), Cholesterol, 1,2-Distearoyl-sn-Glycero-3-Phosphoethanolamine-N-Biotinyl(Polyethylene Glycol) 2000](Ammonium Salt) (DSPE-PEG2000Biotin), and Tm-21a complex (chelator 21a is shown in FIG. 8C) were dissolved in a chloroform/methanol 3:1 mixture. The molar ratio of the components (POPC/Chol/DSPE-PEG2000-Biotin/Tm-21a) was 43:28:4:25 and the total amount of the components was 20 mg.

The solution was slowly evaporated in order to obtain a thin lipidic film which was further dried under vacuum for 2 hours.

The film was hydrated with 1 mL of a solution of [Tm-20]⁻ 0.02 M. The suspension was vortexed at 55° C. and then extruded (55° C., 4000 kPa) 5 times through polycarbonate filters (diameter 200 nm).

The resulting biotinylated liposomes were dialysed in order to remove the not-encapsulated metal complex (two dialysis cycles of 4 hours each against an isotonic buffer at pH 7).

Characterisation

The Mean Size of this LIPOCEST Preparation was 170 nm (PDI=0.1)

FIG. 13 reports the $^1$H-NMR spectrum (14.1 T, 298 K) of this preparation. The chemical shift difference between intraliposomal and bulk water was 15 ppm. FIG. 14 reports the normalised Z-spectra of diluted samples of this preparation (7 T, irrad. pulse: rectangular, irrad. power 6 mT, irrad. time 2 s, 312 K). A ST % of ca. 10% was still detected in the sample diluted 64 times.

Example 3

Preparation and Characterisation of Biotinylated LIPOCEST Agents Encapsulating [Tm-21](Chelator 21 is Shown in FIG. 8C)

Preparation 1,2-Dipalmitoyl-sn-Glycero-3-Phosphocholine (DPPC) and 1,2-Distearoyl-sn-Glycero-3-Phosphoethanolamine-N-[Biotinyl(Polyethylene Glycol)2000](Ammonium Salt) (DSPE-PEG2000Biotin) were dissolved in a chloroform/methanol 3:1 mixture. The molar ratio of the components (DPPC/DSPE-PEG2000-Biotin) was 95:5 and the total amount of the components was 20 mg.

The solution was slowly evaporated in order to obtain a thin lipidic film which was further dried under vacuum for 2 hours.

The film was hydrated with 1 mL of a solution of [Tm-21] 0.04 M. The suspension was vortexed at 55° C. and then extruded (55° C., 4000 kPa) 5 times through polycarbonate filters (diameter 200 nm).

The resulting biotinylated liposomes were dialysed in order to remove the not-encapsulated metal complex (two dialysis cycles of 4 hours each against an isotonic buffer at pH 7).

Characterisation

The mean size of this LIPOCEST preparation was 160 nm (PDI=0.1) FIG. 15 reports the $^1$H-NMR spectrum (14.1 T, 298 K) of this preparation. The chemical shift difference between intraliposomal and bulk water was 10 ppm.

Example 4

Preparation and Characterisation of Biotinylated LIPOCEST Agents Incorporating Gd-21a and Encapsulating [Gd-21]

Preparation 1,2-Dipalmitoyl-sn-Glycero-3-Phosphocholine (DPPC), 1,2-Distearoyl-sn-Glycero-3-Phosphoethanolamine-N-[Biotinyl(Polyethylene Glycol)2000](Ammonium Salt) (DSPE-PEG2000Biotin), and Gd-21a complex were dissolved in a chloroform/methanol 3:1 mixture. The molar ratio of the components (DPPC/DSPE-PEG2000-Biotin/Gd-21a) was 60:5:35 and the total amount of the components was 20 mg.

The solution was slowly evaporated in order to obtain a thin lipidic film which was further dried under vacuum for 2 hours.

The film was hydrated with 1 mL of a solution of [Gd-21] 0.04 M. The suspension was vortexed at 55° C. and then extruded (55° C., 4000 kPa) 5 times through polycarbonate filters (diameter 200 nm).

The resulting biotinylated liposomes were dialysed in order to remove the not-encapsulated metal complex (two dialysis cycles of 4 hours each against an isotonic buffer at pH 7).

Characterisation

The mean size of this LIPOCEST preparation was 140 nm (PDI=0.1) FIG. 16 reports the $^1$H-NMR spectrum (14.1 T, 298 K) of this preparation. The chemical shift difference between intraliposomal and bulk water was 19.3 ppm.

Example 5

Preparation and Characterisation of Biotinylated LIPOCEST Agents Incorporating Dy-21a and Encapsulating [Tm-20]⁻

Preparation 1,2-Dipalmitoyl-sn-Glycero-3-Phosphocholine (DPPC), 1,2-Distearoyl-sn-Glycero-3-Phosphoethanolamine-N-[Biotinyl(Polyethylene Glycol)2000](Ammonium Salt) (DSPE-PEG2000Biotin), and Dy-21a complex were dissolved in a chloroform/methanol 3:1 mixture. The molar ratio of the components (DPPC/DSPE-PEG2000-Biotin/Gd-21a) was 60:5:35 and the total amount of the components was 20 mg.

The solution was slowly evaporated in order to obtain a thin lipidic film which was further dried under vacuum for 2 hours.

The film was hydrated with 1 mL of a solution of [Tm-20]⁻ 0.02 M. The suspension was vortexed at 55° C. and then extruded (55° C., 4000 kPa) 5 times through polycarbonate filters (diameter 200 nm).

The resulting biotinylated liposomes were dialysed in order to remove the not-encapsulated metal complex (two dialysis cycles of 4 hours each against an isotonic buffer at pH 7).

Characterisation

The mean size of this LIPOCEST preparation was 160 nm (PDI=0.1) FIG. 17 reports the $^1$H-NMR spectrum (14.1 T, 298 K) of this preparation. The chemical shift difference between intraliposomal and bulk water was −36 ppm.

Example 6

Preparation and Characterisation of LIPOCEST Agents Encapsulating [Tm-20]⁻ and Incorporating a Compound of Formula (III) Wherein $R_6$ is the N-Succinyl-Dioctadecylamine Lipid Moiety Preparation 1-Palmitoyl-2-Oleoyl-sn-Glycero-3-Phosphocholine (POPC), Cholesterol, 1,2-Distearoyl-sn-Glycero-3-Phosphoethanolamine-N-[methoxy(Polyethylene glycol)2000] (Ammonium Salt) (DSPE-PEG2000), and the peptidomimetic derivatives according to formula (III) comprising N-Succinyl-dioctadecylamine as lipid moiety, (lipid derivative I of scheme 12) were dissolved in a chloroform/methanol 3:1 mixture. The molar ratio of the components (POPC/Chol/DSPE-PEG2000/targeting lipid) was 55:40:2.5:2.5 and the total amount of the components was 20 mg.

The solution was slowly evaporated in order to obtain a thin lipidic film which was further dried under vacuum for 2 hours.

The film was hydrated with 1 mL of a solution of [Tm-20]⁻ 0.2 M. The suspension was vortexed at 55° C. and then extruded (55° C., 4000 kPa) 5 times through polycarbonate filters (diameter 200 nm).

The resulting liposomes were dialysed in order to remove the not-encapsulated metal complex (two dialysis cycles of 4 hours each against an isotonic buffer at pH 7).
Characterisation The mean size of this LIPOCEST preparation was 200 nm (PDI=0.1)

FIG. 18 reports the $^1$H-NMR spectrum (14.1 T, 298 K) of this preparation. The chemical shift difference between intraliposomal and bulk water was 3 ppm.

Example 7

Visualization of Integrin Receptors by Use of a Peptidomimetic Derivative According to Formula (III) wherein $R_6$ is a Biotin Moiety and a LIPOCEST Agent Preparation and characterisation of and cell targeting of biotinylated LIPOCEST agents incorporating Tm-21a and encapsulating [Tm-20]$^-$.
Preparation 1-Palmitoyl-2-Oleoyl-sn-Glycero-3-Phosphocholine (POPC), Cholesterol, and 1,2-Distearoyl-sn-Glycero-3-Phosphoethanolamine-N-[Biotinyl(Polyethylene Glycol) 2000](Ammonium Salt) (DSPE-PEG2000Biotin), and Tm-21a complex were dissolved in a chloroform/methanol 3:1 mixture. The molar ratio of the components (POPC/Chol/DSPE-PEG2000-Biotin/Tm-21a) was 43:28:4:25 and the total amount of lipids was 20 mg.

The solution was slowly evaporated in order to obtain a thin lipidic film which was further dried under vacuum for 2 hours.

The film was hydrated with 1 mL of a solution of [Tm-20]$^-$ 0.02 M. The suspension was vortexed at 55° C. and then extruded (55° C., 4000 kPa) 5 times through polycarbonate filters (diameter 200 nm).

The resulting biotinylated liposomes were dialysed in order to remove the not-encapsulated metal complex (two dialysis cycles of 4 hours each against an isotonic buffer at pH 7).
Characterisation The mean size of this LIPOCEST preparation was 190 nm (PDI=0.1)

The chemical shift difference between intraliposomal and bulk water was 11.0 ppm (298 K).
Cell Targeting Experiment Ca. 1×10$^6$ HUVEC (Human Umbilical Vein Endothelial Cells; see, as reference, Garlanda C. Parravicini C. Sironi M. De Rossi M. Wainstok de Calmanovici R. Carozzi F. Bussolino F. Calotta F. Mantovani A. Vecchi A., Progressive growth in immunodeficient mice and host cell recruitment by mouse endothelial cells transformed by polyoma middle-sized T antigen: implications for the phatogenesis of opportunistic vascular tumors; 1994, Proc Natl Acad Sci USA, 91, 7291-7295) cells were detached from the cell culture medium by EDTA (0.3 g/L) and washed three times with ice-cold PBS buffer. About 5×10$^5$ cells were suspended in 200 μL of a solution containing the biotinylated targeting peptide of the invention, i.e. a peptidomimetic derivative according to formula (III) wherein $R_6$ is a biotin moiety, (60 μM) and incubated at 4° C. After 15 mins of incubation, the cells were washed two times with ice-cold PBS buffer and suspended in 200 μL of a solution containing streptavidin (2 μM). After 15 mins of incubation at 4° C., the cells were washed two times with ice-cold PBS buffer and suspended in 200 μL of a suspension containing the biotinylated LIPOCEST. Finally, after 15 mins of incubation at 4° C., the cells were washed three times with ice-cold PBS buffer and the cellular pellet was imaged by MRI.

In parallel, the remaining HUVEC cells (ca. 5×10$^5$) were used as control and were only washed three times with ice-cold PBS buffer.

FIG. 19 reports the ST spectra of the two cellular pellets of Example 7, including, the first HUVEC cells treated with the biotinilated LIPOCEST and the second only HUVEC cells as control (7 T, irrad. pulse: rectangular, irrad. power 12 PT, irrad. time 2 s, 293 K). The treated HUVEC cells displays a maximum Saturation Transfer % of ca. 4% upon irradiation at 10 ppm from the resonance of bulk water.

FIG. 20 reports the corresponding CEST-MR images [on-(irradiation at 10 ppm from bulk water), off-(irradiation at −10 ppm from bulk water), and (on-off)] of the phantom made of two capillaries containing the two cellular pellets. Importantly, only the treated HUVEC cells are visible in the on-off difference image when the irradiation is carried out at 10 ppm from the bulk water.
Pharmacokinetic Determination
Protocol Outline
Introduction Biological tests for the evaluation of the affinity of the compounds of the invention towards the αvβ3 and αvβ5 integrins may be performed using known tests also described in the literature [C. C. Kumar, H. Nie, C. P. Rogers, M. Malkowski, E. Maxwell, J. J. Catino, L. Armstrong, *J. Pharmacol. Exp. Ther.* 1997, 283, 843] for example such as the one reported in patent application EP 1 077 218.

In the present case, the following protocol has been applied.
Materials
Test Articles
Reagents
Compound: Penicillin/Streptomycin (10000 μg/mL)
Supplier: Euroclone®, Wetherby, West York, UK
Compound: L-Glutamine (200 mM)
Supplier: Biochrom KG, Berlin, Germany
Compound: Foetal Calf Serum (FCS)
Supplier: HyClone®, Logan, Utah, U.S.A.
Compound: Dulbecco's Modified Eagle's Medium (DMEM)
Supplier: SIGMA Chemicals, St. Louis, Mo., U.S.A.
Compound: Non-essential amino acids
Supplier: SIGMA Chemical Co, Sigma-Aldrich. Chem. GMBH Berlin, Germany
Compound: Sodium pyruvate
Supplier: SIGMA Chemical Co, Sigma-Aldrich. Chem. GMBH Berlin, Germany
Compound: Dulbecco's Phosphate Buffered Saline (PBS-)
Supplier: SIGMA Chemical Co, Sigma-Aldrich. Chem. GMBH Berlin, Germany
Compound: Trypsin-EDTA
Supplier: SIGMA Chemical Co, Sigma-Aldrich. Chem. GMBH Berlin, Germany
Compound: 0.9% Sodium Chloride solution
Supplier: S.A.L.F. SpA Laboratorio Farmaceutico, Bergamo, Italy
Compound: Endothelial Cell Basal Medium-2 (EBM-2)
Supplier: Cambrex Bio Science Walkersville Inc., Walkersville, Md., U.S.A.

Compound: EGM-2 MV Single Quots
Supplier: Cambrex Bio Science Walkersville, Inc. Walkersville, Md., U.S.A.
Mouse anti-human integrin αvβ3 monoclonal antibody
Supplier: Chemicon International Inc., 28835 Single Oak Drive, Tamecula Calif.
Goat anti-mouse IgG fluorescein conjugated antibody
Supplier: Chemicon International Inc., 28835 Single Oak Drive, Tamecula Calif.
Vitronectin from Human Plasma
Supplier: SIGMA Chemical Co, Sigma-Aldrich. Chem. GMBH Berlin, Germany
Cycle(Arg-Gly-Asp-D-Phen-Val) peptide
Supplier: Bachem AG, 4416 Bubendorf, Switzerland
Human Integrin αvβ3 purified protein
Supplier: Chemicon International Inc., 28835 Single Oak Drive, Tamecula Calif.
NeutrAvidin horseradish peroxidase conjugated
Supplier: Pierce Biotechnology Inc., Rockford, Ill. 61105

Test System

Justification of the choice of the test system: Endothelial cells from different origins and tumor cell lines expressing $\alpha v\beta_3$ or $\alpha v\beta_5$ receptors have been chosen as test system since they are suitable to test the specific binding of cyclic peptides to $\alpha v\beta_3$ integrin receptor in vitro.

Biological Samples

H5V cell lines were grown in 90% DMEM supplemented with 2 mM L-glutamine, 100 µg/mL Penicillin/Streptomycin, 0.1 mM non-essential amino acids, 1.0 mM sodium pyruvate and 10% FCS.

HUVEC cells were grown in Endothelial Cell Basal Medium-2 supplemented with EGM-2 MV Single Quots.

Location of Experimental Phases

Methods

Experimental Procedures

FACS Analysis

Selected cell lines were detached at confluence by treatment with 0.02% EDTA, washed in PBS and maintained in suspension for 1 hour in culture medium. Cells were then incubated with the primary antibody anti-human integrin $\alpha v\beta_3$ for 1 hour at 4° C., washed in PBS and incubated with a specific FITC-labelled secondary antibody at the same conditions. After washing in PBS, cell surface fluorescence were analyzed by flow cytometer fuorescence-activated cell sorting (FACS) scan.

The same procedure is utilized to stain the cells with FITC-labelled integrin antagonists.

Adhesion Assay 96-wells tissue culture plates were coated with either fibronectin or vitronectin (5 µg/mL), overnight at 4° C. Selected cell lines were seeded in each well and allow to adhere for 1 or 3 hours at 37° C. in the presence of various concentration of integrin antagonists or primary antibody anti-human integrin αvβ3 as positive control. Non adherent cells were removed with PBS and the remaining cells were fixed with 3.5% paraformaldehyde for 10 minutes, stained with 0.5% Crystal violet for 10 minutes and washed with water. Stained cells were solubilized and the amount of adherent cells were quantified by measuring the absorbance at 575 nm on a microtiter plate reader. Experiments were done in six replicates and repeated at least twice. Results are expressed as mean+/−SD compound concentration that inhibits 50% of cell adhesion.

Ligand Binding Assay

Purified integrin $\alpha v\beta_3$ and $\alpha v\beta_5$ receptors were diluted to 0.5 or 1 g/mL in coating buffer containing 20 mmol/L Tris-HCl (PH 7.4), 150 mmol/L NaCl, and 1 mmol/L $MnCl_2$ in the presence of 2 mmol/L $CaCl_2$ and 1 mmol/L $MgCl_2$. An aliquot of diluted receptors (100 µL/well) was added to 96-well microtiter plates and incubated overnight at 4° C. Then the plates were washed and the aspecific binding sites were blocked with coating buffer plus 1-2% bovine serum albumin at room temperature for 2 hours. The blocking buffer was removed and the wells were washed 3 times and incubated in quadruplicate with different concentration (0.1-10 µM) of integrin antagonists and 1 µg/mL biotinylated human vitronectin at room temperature for 3 hours as standard competitors. The plates were washed 3 times and the bounded competitor was detected using strepto-avidin-HRP conjugate at 0.01 µg/well (3).

The integrin antagonist concentration producing 50% inhibition of vitronectin binding to purified protein was calculated.

Proliferation Assay

For the proliferation assay, selected cell lines were seeded in 96-well plates in complete medium. After 24 hours the medium were removed and replaced with fresh medium containing scalar concentration of integrin antagonists. The plates were incubated for additional 72 hours before assessing the cell proliferation by MTT or other alternative proliferation assay.

Immunofluorescence

Selected cell lines were detached at confluence by treatment with 0.02% EDTA, washed in PBS and were seeded on a glass coverlip up to confluence. Cells were fixed, then incubated with the FITC-labelled integrin antagonist or with the primary antibody anti-human integrin $\alpha v\beta_3$ for 1 hour, washed in PBS, containing 0.1% BSA, and incubated with the specific FITC-labelled secondary antibody. After washing in PBS, the integrin receptor positive cells were analyzed by fluorescent-microscopy.

Platelet Aggregation Assay

The platelet aggregation response to 11-mer thrombin receptor-activating peptide (25-100 µmol/L) was measured in platelet-rich plasma from guinea pig, human or rabbit. The platelet concentration was adjusted in platelet-poor plasma to $3\times10^8$/mL and platelet aggregation was determined within 1 hour by turbidometric method in a dual-channel aggregometer. Vehicle or different concentrations of peptide was added to platelet-rich plasma 1 minute before starting aggregation. The extent of platelet aggregation was quantified as the maximum change in light transmittance within 4 minutes after the addition of the agonist. The results were expressed as the antagonist concentration that inhibit 50% platelet aggregation.

In Vitro Invasion Assay

The invasion assay was performed in the transwell system. A suspension of selected tumor cell lines ($0.5-1\times10^6$/mL) was added in the upper compartment of the transwell insert coated with different basement proteins in presence of integrin receptor antagonists. The transwells were incubated for 24 hours before to remove the non invading cells and the matrix proteins. The migrating and invading cells on the lower surface of transwell unit were stained and quantified by optical microscope.

In Vitro Vessel Formation Assay

The vessel formation assay was performed according to the "In vitro angiogenesis assay kit" purchased from Chemicon international.

Parties to the joint research agreement are the University of Milan—Center of Excellence, Institute of Science and Molecular Technology—CNR (National Research Council), Colosseum Combinatorial Chemistry Centre for Technology—University of Rome—Tor Vergata, Immune-Biological Research Institute of Siena (Chiron Group), Bracco Imaging S.p.A., Inpeco, and Pharmacia-Italy.

REFERENCES

J. J. Marugan et all. Design, Synthesis and biological evaluation of novel potent and selective $\alpha v\beta_3/\alpha v\beta_5$ integrin dual inhibitors with improved bioavailability. Selection of the molecular care. J. Med. Chem. 2005, 48, pp. 926-934.

L. Belvisi et all. Biological and molecular properties of a new $\alpha v\beta_3/\alpha v\beta_3$ integrin antagonist. Mol Cancer Ther 2005, 4(11), pp. 1670-1680.

R. Haubner et all. Structural and functional aspects of RGD-containing cyclic pentapeptides as highly potent and selective integrin $\alpha v\beta_3$ antagonists. J. Am. Chem. Soc. 1996, 118, pp. 7461-7472.

We claim:
1. A compound of formula (III)

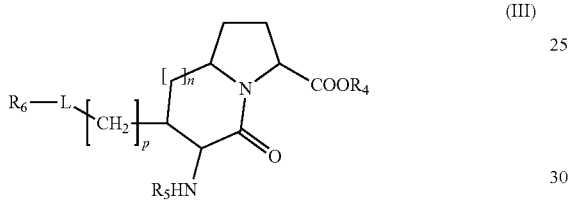

wherein
n is 1,
p is 1,
$OR_4$ and $R_5$ together constitute the sequence Asp-Gly-Arg,
$R_6$ is a radiotherapeutically or diagnostically effective molecule, and
L is —CONH—;
or a salt of the compound of formula (III).

2. The compound of claim 1 wherein $R_6$ is a diagnostically effective molecule comprising an imaging detectable moiety.

3. The compound of claim 2 wherein $R_6$ is selected from the group consisting of: a dye molecule, a fluorescent molecule, a phosphorescent molecule, a molecule absorbing in the UV spectrum, a quantum dot, and a molecule absorbing near or far infrared radiations.

4. The compound of claim 3 wherein $R_6$ is a fluorescent molecule.

5. The compound of claim 3 wherein $R_6$ is a near infrared (NIR) dye.

6. The compound of claim 5 wherein $R_6$ is a cyanine or indocyanine derivative selected from the group consisting of Cy5.5, IRDye800, indocyanine green (ICG) and tetrasulfonic acid substituted ICG.

7. The compound of claim 6 wherein $R_6$ is Cy5.5.

8. A pharmaceutical composition comprising the compound of claim 7 and at least one pharmaceutically acceptable excipient.

9. A pharmaceutical composition comprising the compound of claim 7, wherein said composition is suitable for parenteral administration.

10. A diagnostic or radiotherapeutic agent comprising the compound of formula (III) as defined in claim 1.

11. A pharmaceutical composition comprising the diagnostic or radiotherapeutic agent of claim 10 and pharmaceutically acceptable excipients, carriers and/or diluents.

12. A multimeric construct of formula (IV)

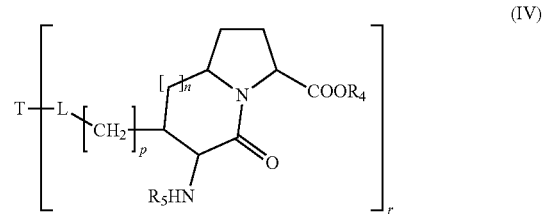

wherein:
n is 1 or 2;
p is an integer between 1 and 5;
$OR_4$ and $R_5$ together constitute the sequence Asp-Gly-Arg;
L is a group (i) —CONH—, (ii) —NHCONH—, (iii) —NHCSNH—,

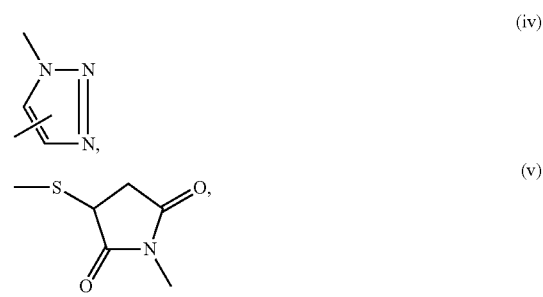

or is a divalent linking moiety comprising two of the groups (i), (ii), (iii), (iv), and/or (v) as terminal groups;
T is an anchoring system containing at least three, optionally protected, equal or different binding sites or functional groups derived from a polyvalent organic residue that is aliphatic with open chain, optionally branched, alicyclic, heterocyclic containing N, O, and/or S, aromatic, or heteroaromatic, or T is an avidin or streptavidin moiety; and
r is an integer from 2 to 10;
or a salt of the multimeric construct of formula (IV).

13. The multimeric construct of claim 12 wherein T is selected from the group consisting of:
(a) N-branched lysine systems,
(b) polycarboxylic derivatives,
(c) polyaminated derivatives, and
(d) amino acids.

14. A multimeric construct of formula (V)

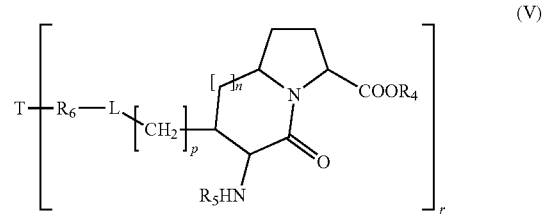

wherein:
n is 1 or 2;
p is an integer between 1 and 5;
$OR_4$ and $R_5$ together constitute the sequence Asp-Gly-Arg;

L is a group (i) —CONH—, (ii) —NHCONH—, (iii) —NHCSNH—,

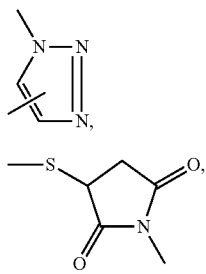
(iv)

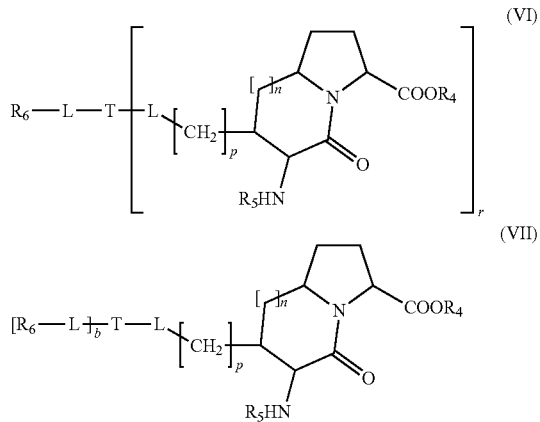
(v)

or is a divalent linking moiety comprising two of the groups (i), (ii), (iii), (iv), and/or (v) as terminal groups;
$R_6$ is a biotin moiety;
T is a streptavidin or an avidin moiety; and
r is 2 or 3;
or a salt of the multimeric construct of formula (V).

15. A macromolecular aggregate comprising a liposome, micelle, microemulsion, vesicle, microsphere, paramagnetic liposome, LIPOCEST agent, or gas containing vesicle having a number of biotin residues on the surface thereof, wherein said biotin residues are coupled with the multimeric construct of formula (V) as defined in claim 14.

16. A multimeric construct of formula (VI) or formula (VII)

(VI)

$$R_6-L-T\left[L\underset{R_5HN}{\overset{[CH_2]_p}{\diagdown}}\underset{}{\overset{[]_n}{\diagup}}\text{COOR}_4\right]_r$$

(VII)

$$[R_6-L]_b-T\underset{R_5HN}{\overset{[CH_2]_p}{\diagdown}}\underset{}{\overset{[]_n}{\diagup}}\text{COOR}_4$$

wherein:
n is 1 or 2;
p is an integer between 1 and 5;
$OR_4$ and $R_5$ together constitute the sequence Asp-Gly-Arg;

L is a group (i) —CONH—, (ii) —NHCONH—, (iii) —NHCSNH—,

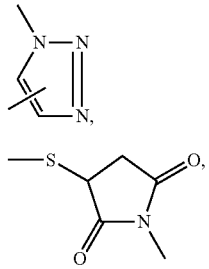
(iv)

(v)

or is a divalent linking moiety comprising two of the groups (i), (ii), (iii), (iv), and/or (v) as terminal groups;
$R_6$ is a biologically active moiety selected from the group consisting of a radiotherapeutically or diagnostically effective molecule, a phospholipid or lipid moiety, and a biotin or an avidin residue;
T is selected from the group consisting of N-branched lysine systems, polycarboxylic derivatives, polyaminated derivatives, and amino acids;
r is an integer from 2 to 10; and
b is an integer from 2 to 5;
or a salt of the multimeric construct of formula (VI) or formula (VII).

17. The multimeric construct of formula (VI) or formula (VII) as defined in claim 16 wherein $R_6$ is a diagnostically or radiotherapeutically effective moiety.

18. A macromolecular system comprising the multimeric construct of formula (VI) or of formula (VII) as defined in claim 16 in which $R_6$ is a phospholipid or lipid moiety incorporated within a paramagnetic liposome, LIPOCEST, or gas-containing vesicle, for use as a diagnostic agent.

19. A diagnostic or radiotherapeutic agent comprising the multimeric construct of formula (VI) or formula (VII) as defined in claim 16 wherein $R_6$ is a diagnostically or radiotherapeutically effective molecule.

20. A pharmaceutical composition comprising the diagnostic or radiotherapeutic agent of claim 19 and pharmaceutically acceptable excipients, carriers and/or diluents.

* * * * *